(12) United States Patent
Bandyopadhyay et al.

(10) Patent No.: US 11,312,709 B2
(45) Date of Patent: Apr. 26, 2022

(54) GHRELIN O-ACYLTRANSFERASE INHIBITORS

(71) Applicant: Glaxosmithkline Intellectual Property Development Limited, Brentford (GB)

(72) Inventors: Anish Bandyopadhyay, Hyderabad (IN); Mui Cheung, King of Prussia, PA (US); Hilary Schenck Eidam, Stevenage (GB); Hemant Joshi, Hyderabad (IN); Dai-Shi Su, Collegeville, PA (US)

(73) Assignee: Glaxosmithkline Intellectual Property Development Limited, Brentford (GB)

( * ) Notice: Subject to any disclaimer, the term of this patent is extended or adjusted under 35 U.S.C. 154(b) by 70 days.

(21) Appl. No.: 16/967,262

(22) PCT Filed: Feb. 5, 2019

(86) PCT No.: PCT/EP2019/052770
§ 371 (c)(1),
(2) Date: Aug. 4, 2020

(87) PCT Pub. No.: WO2019/149959
PCT Pub. Date: Aug. 8, 2019

(65) Prior Publication Data
US 2021/0053955 A1    Feb. 25, 2021

(30) Foreign Application Priority Data

Feb. 5, 2018    (IN) .............................. 201811004277

(51) Int. Cl.
*C07D 409/12*    (2006.01)
*C07D 491/048*    (2006.01)
*A61K 45/06*    (2006.01)

(52) U.S. Cl.
CPC ....... *C07D 409/12* (2013.01); *C07D 491/048* (2013.01); *A61K 45/06* (2013.01)

(58) Field of Classification Search
CPC .......................... C07D 491/048; A61K 45/06
See application file for complete search history.

(56) References Cited

FOREIGN PATENT DOCUMENTS

| | | | |
|---|---|---|---|
| JP | WO 2013/125732 | * | 8/2013 |
| WO | WO 2010/143733 A1 | | 12/2010 |
| WO | WO 2013/125732 A1 | | 8/2013 |
| WO | WO 2013/144097 A1 | | 10/2013 |
| WO | WO 2015/024526 A1 | | 2/2015 |

OTHER PUBLICATIONS

Cummings, D.E. Physiology and Behavior, 89(1):71-84 (2006) (Year: 2006).*
Barnett et al., Science 2010, 330 (6011), 1689-1692 (Year: 2010).*
PCT/EP2019/052770, May 15, 2019, International Search Report and Written Opinion.
PCT/EP2019/052770, Aug. 20, 2020, International Preliminary Report on Patentability.

* cited by examiner

*Primary Examiner* — Dennis Heyer
(74) *Attorney, Agent, or Firm* — Wolf, Greenfield & Sacks, P.C.

(57) ABSTRACT

This invention relates to novel compounds according to Formula (I) which are inhibitors of ghrelin O-acyltransferase (GOAT), to pharmaceutical compositions containing them, to processes for their preparation, and to their use in therapy for the treatment of metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.).

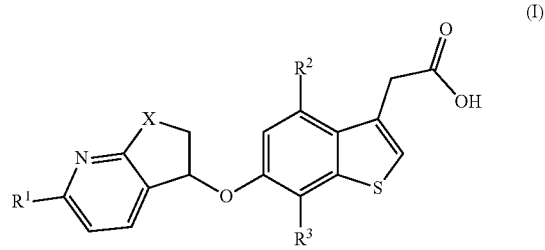

20 Claims, 8 Drawing Sheets

GHRELIN O-ACYLTRANSFERASE INHIBITORS

RELATED APPLICATIONS

The present application is a national stage filing under 35 U.S.C. § 371 of international PCT application, PCT/EP2019/052770, filed Feb. 5, 2019, which claims priority under 35 U.S.C. § 119(a) to Indian patent application, Application Number 201811004277, filed Feb. 5, 2018, the entire contents of each of which are incorporated herein by reference.

FIELD OF THE INVENTION

This invention relates to compounds which inhibit ghrelin O-acyltransferase (GOAT) and thus are useful for reducing appetite and adiposity, as well as improving energy balance and glycemic control.

BACKGROUND OF THE INVENTION

Ghrelin is a 28-amino acid gastric hormone produced primarily in the fundus of the stomach. Two forms of the hormone are found in circulation: unacylated ghrelin and acylated ghrelin. The lone enzyme known to perform this post-translational acylation on serine 3 of ghrelin is ghrelin O-acyltransferase (GOAT). There is no other known function of GOAT. Only acyl ghrelin is capable of interacting with its receptor, growth hormone secretagogue receptor 1 (GHSR1). Binding of acyl ghrelin to GHSR1 in the brain stimulates orexigenic activity and adiposity and reduces energy expenditure. When acyl ghrelin was administered to humans, appetite and food intake were increased (covered in Cummings, *Physiology & Behavior* 2006, 89, 71-84). Binding of acyl ghrelin to GHSR1 in pancreatic islet cells modulates insulin release. Acute administration of acyl ghrelin to humans led to significant reductions in plasma insulin and increased glucose levels (Broglio, *J. Clin. Endocrinol. Metab.* 2001, 86, 5083-5086).

Levels of acylated ghrelin increase in anticipation of a meal and decrease post-prandially, leading acyl ghrelin to dubbed the "hunger hormone." If increased levels of acyl ghrelin stimulate adiposity and adversely impact glycemic control, which could contribute to the development of the metabolic syndrome, then decreasing the amount of acyl ghrelin in circulation should do the opposite: reduce appetite and adiposity, improve energy balance, and benefit glycemic control, potentially ameliorating the metabolic syndrome. Inhibition of GOAT decreases acyl ghrelin production. Indeed, as reviewed by Ariyasu and Akamizu (*Endocrine Journal* 2015, 62(11), 953-963) mice with ghrelin, GHSR1, or GOAT knocked out demonstrate decreased food intake on a high fat diet and increased insulin secretion. When wild type mice were administered a peptide-based GOAT inhibitor, they demonstrated reduced weight gain and improved glucose tolerance (Barnett et al., *Science* 2010, 330 (6011), 1689-1692). In addition, it was recently reported that ghrelin deletion is protective against age-associated hepatic steatosis, suggesting a role for GOAT inhibition in the treatment of nonalcoholic steatohepatitis (NASH) (Guillory et al., *Aging Cell* 2017 published ahead of print 10.1111/ace1.12688).

Thus, there is strong evidence to suggest that inhibition of GOAT decreases appetite and adiposity and improves glycemic control. Accordingly, compounds that inhibit GOAT activity would be useful for the treatment of obesity.

SUMMARY OF THE INVENTION

The present invention relates to compounds according to Formula (I) or pharmaceutically acceptable salts thereof.

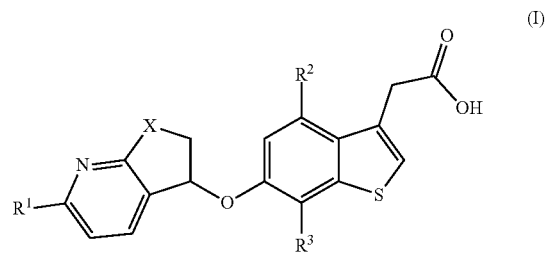

wherein:
$R^1$ is hydrogen, halogen, cyano, $(C_1-C_4)$alkyl, halo$(C_1-C_4)$alkyl, or $—C(=O)NH_2$;
X is $CH_2$ or O;
$R^2$ is halogen; and
$R^3$ is hydrogen or halogen.

Exemplary compounds of Formula (I) include, but are not limited to:

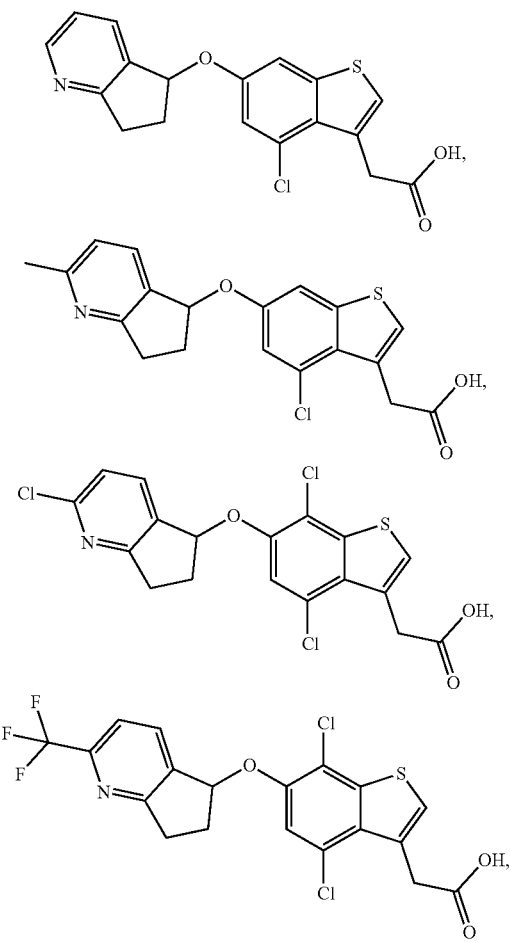

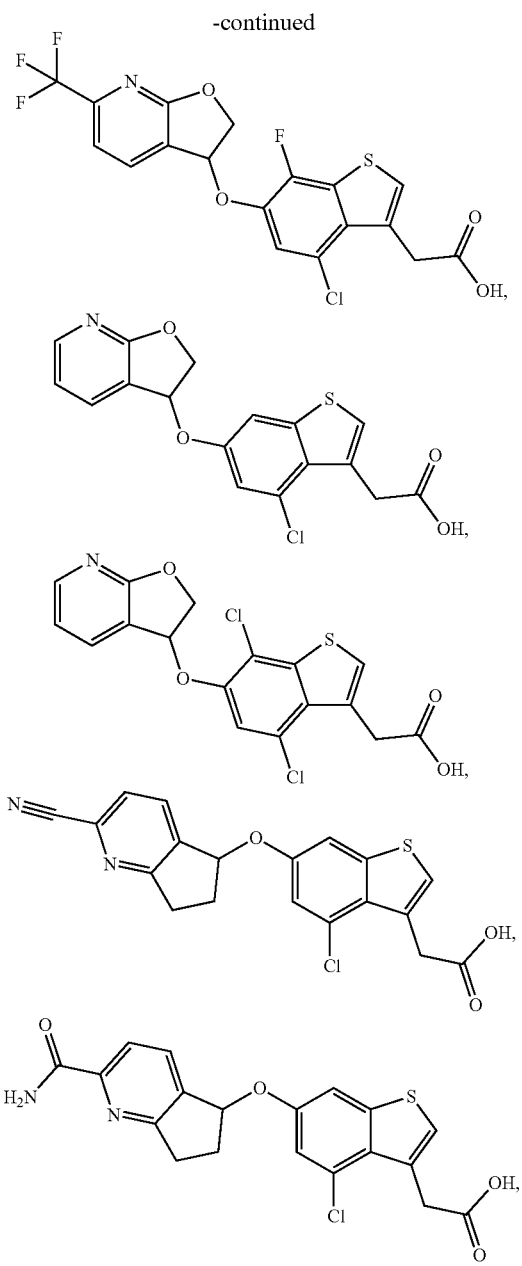

and pharmaceutically acceptable salts thereof.

Another aspect of this invention relates to a method of treating obesity. In particular, this invention relates to a method of treating obesity caused by Prader-Willi syndrome. Prader-Willi syndrome is a well-known genetic cause of obesity and is found in people of both sexes and in all races worldwide, particularly in children. Patients suffering from Prader-Willi syndrome experience hyperphagia and typically have trouble controlling their weight. Many complications of Prader-Willi syndrome are due to obesity.

Another aspect of this invention relates to a method of treating metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.).

Another aspect of the invention relates to pharmaceutical preparations comprising compounds of Formula (I) and pharmaceutically acceptable excipients.

In another aspect, there is provided the use of a compound of Formula (I) or a pharmaceutically acceptable salt or solvate thereof, in the manufacture of a medicament for use in the treatment of a disorder mediated by GOAT, such as obesity. In another aspect, there is provided the use of a compound of Formula (I) or a pharmaceutically acceptable salt or solvate thereof, in the manufacture of a medicament for use in the treatment of a disorder mediated by GOAT, such as metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.).

In another aspect, the invention provides a compound of Formula (I) or a pharmaceutically acceptable salt thereof for use in therapy.

In another aspect, there is provided a compound of Formula (I) or a pharmaceutically acceptable salt thereof for use in the treatment of a disorder mediated by GOAT.

In another aspect, there is provided a compound of Formula (I) or a pharmaceutically acceptable salt thereof for use in the treatment of obesity.

In another aspect, there is provided a compound of Formula (I) or a pharmaceutically acceptable salt thereof for use in the treatment of metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.).

In another aspect, there is provided a compound of Formula (I) or a pharmaceutically acceptable salt thereof for use in the treatment of Prader-Willi syndrome.

In another aspect, provided herein are methods of co-administering the presently invented compounds of Formula (I) with other active ingredients.

In another aspect, there is provided a combination of a compound of Formula (I) or a pharmaceutically acceptable salt thereof and at least one anti-adiposity agent or anti-adiposity therapy for use in the treatment of a disorder mediated by GOAT.

In another aspect, there is provided a combination of a compound of Formula (I) or a pharmaceutically acceptable salt thereof and at least one lifestyle modification (e.g., a reduced-calorie diet and/or exercise), weight loss agent (e.g., orlistat, lorcaserin, liraglutide, phentermine/topimarate, or naltrexone/bupropion), hormone therapy (e.g., testosterone, estrogen, progesterone, or human growth hormone), selective serotonin reuptake inhibitors (SSRIs), or anti-diabetic therapy (e.g., insulin, miglitol, acarbose, metformin, exenatide, pramlintide) for use in the treatment of a disorder mediated by GOAT.

In another aspect, there is provided a combination of a compound of Formula (I) or a pharmaceutically acceptable salt thereof and at least one anti-adiposity agent or anti-adiposity therapy for use in the treatment of obesity. In another aspect, there is provided a combination of a compound of Formula (I) or a pharmaceutically acceptable salt thereof and at least one lifestyle modification (e.g., a reduced-calorie diet and/or exercise), weight loss agent (e.g., orlistat, lorcaserin, liraglutide, phentermine/topimarate, or naltrexone/bupropion), hormone therapy (e.g., testosterone, estrogen, progesterone, or human growth hormone), selective serotonin reuptake inhibitors (SSRIs), and/or anti-diabetic therapy (e.g., insulin, miglitol, acarbose, metformin, exenatide, pramlintide) for use in the treatment of metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.).

In another aspect, the present disclosure provides pharmaceutical compositions or preparations including a compound described herein, and optionally a pharmaceutically acceptable excipient. In certain embodiments, the pharmaceutical compositions described herein include a therapeutically or prophylactically effective amount of a compound described herein. The pharmaceutical composition or preparation may be useful for treating and/or preventing a disease (e.g., metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.) in a subject in need thereof. The pharmaceutical composition or preparation may be useful for inhibiting the activity of GOAT in a subject, biological sample, tissue, or cell.

In another aspect, the present disclosure provides pharmaceutical compositions or preparations including a compound described herein, and optionally a pharmaceutically acceptable excipient. In certain embodiments, the pharmaceutical compositions described herein include a therapeutically or prophylactically effective amount of a compound described herein. The pharmaceutical composition or preparation may be useful for treating metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.) in a subject in need thereof, or inhibiting the activity of GOAT in a biological sample, tissue, or cell.

In another aspect, described herein are methods for treating and/or preventing a disease (e.g., metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.) in a subject, biological sample, tissue, or cell.

Another aspect relates to methods of inhibiting the activity of GOAT using a compound described herein in a biological sample (e.g., cell, or tissue). In another aspect, described herein are methods of inhibiting the activity of GOAT using a compound described herein in a subject.

In another aspect, the present disclosure provides compounds of Formula (I), and pharmaceutically acceptable salts thereof, for use in the treatment of a disease (e.g., metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.) in a subject, biological sample, tissue, or cell.

Another aspect of the present disclosure relates to kits comprising a container with a compound, or pharmaceutical composition or preparation thereof, as described herein. The kits described herein may include a single dose or multiple doses of the compound or pharmaceutical composition or preparation. The kits may be useful in a method of the disclosure. In certain embodiments, the kit further includes instructions for using the compound or pharmaceutical composition or preparation. A kit described herein may also include information (e.g., prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

BRIEF DESCRIPTION OF THE DRAWINGS

FIG. 1 shows an X-ray powder diffraction pattern of the compound of Example 1a.

FIG. 2 shows a differential scanning calorimetry trace of the compound of Example 1a and a thermogravimetric analysis trace of the compound of Example 1a.

DETAILED DESCRIPTION OF THE INVENTION

Figure 1:
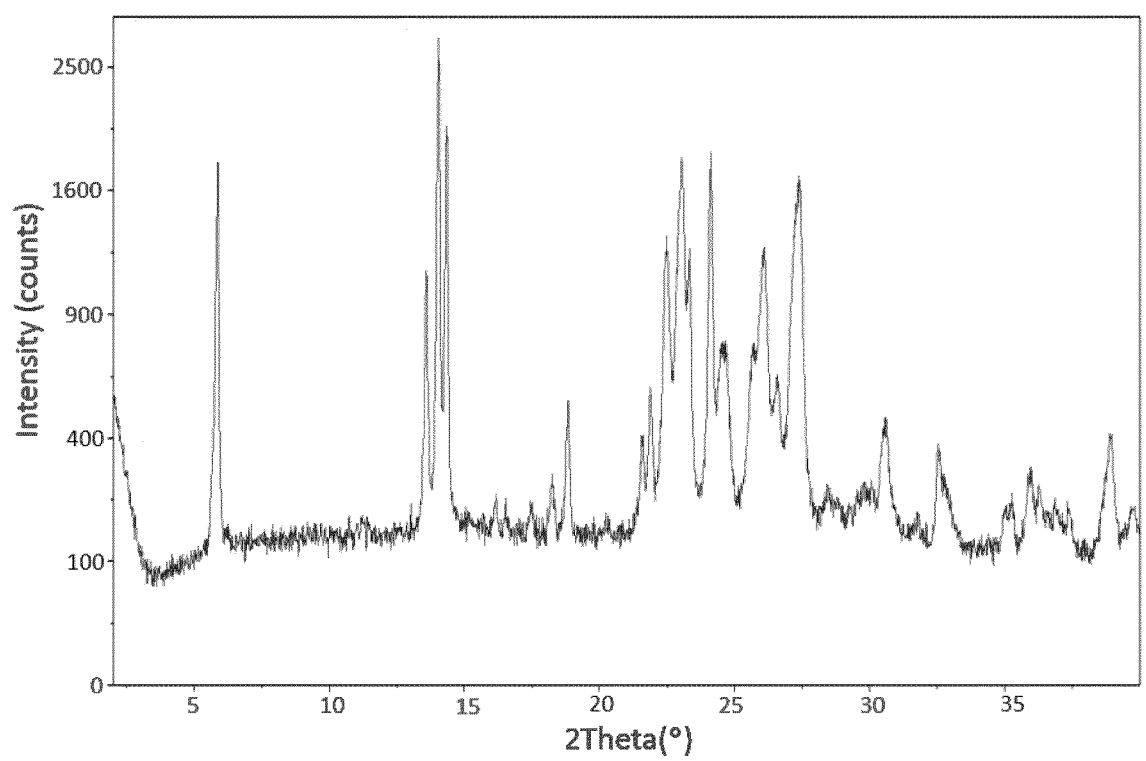

The present invention provides compounds that inhibit GOAT, and pharmaceutical compositions/preparations thereof, for the treatment of a disease in a subject. The present invention further provides methods of using the compounds described herein, e.g., as biological probes to study the inhibition of GOAT or ghrelin activity, and as therapeutics, e.g., in the treatment of diseases associated with GOAT activity. In certain embodiments, the diseases include, but are not limited to, metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.) in a subject, biological sample, tissue or cell.

This invention relates to compounds of the Formula (I) as defined above, or pharmaceutically acceptable salts thereof. Formula (I) contains the substituent $R^1$. In certain embodiments, $R^1$ is H. In certain embodiments, $R^1$ is halogen. In certain embodiments, $R^1$ is Cl. In certain embodiments, $R^1$ is —CN. In certain embodiments, $R^1$ is —($C_1$-$C_4$)alkyl. In certain embodiments, $R^1$ is -Me. In certain embodiments, $R^1$ is -Et. In certain embodiments, $R^1$ is —Pr. In certain embodiments, $R^1$ is -halo($C_1$-$C_4$)alkyl. In certain embodiments, $R^1$ is —$CF_3$. In certain embodiments, $R^1$ is —C(=O)$NH_2$. In certain embodiments, $R^1$ is hydrogen, halogen, cyano, ($C_1$-$C_4$)alkyl, halo($C_1$-$C_4$)alkyl, —C(=O)N($R^a$)$_2$, wherein $R^a$ is hydrogen, substituted or unsubstituted $C_1$-$C_6$ alkyl, or a nitrogen protecting group. In certain embodiments, $R^1$ is —C(=O)N($R^a$)$_2$. In certain embodiments, $R^a$ is hydrogen. In certain embodiments, $R^a$ is substituted or unsubstituted $C_1$-$C_6$ alkyl. In certain embodiments, $R^a$ is -Me. In certain embodiments, $R^a$ is -Et. In certain embodiments, $R^a$ is a nitrogen protecting group.

Formula (I) contains the substituent X. In certain embodiments, X is $CH_2$. In certain embodiments, X is O.

Formula (I) contains the substituent $R^2$. In certain embodiments, $R^2$ is halogen. In certain embodiments, $R^2$ is —Cl.

Formula (I) contains the substituent $R^3$. In certain embodiments, $R^3$ is H. In certain embodiments, $R^3$ is halogen. In certain embodiments, $R^3$ is F. In certain embodiments, $R^3$ is Cl.

In certain embodiments, X is $CH_2$, and $R^1$ is methyl. In certain embodiments, $R^1$ is Me, $R^2$ is Cl, and $R^3$ is H. In certain embodiments, X is $CH_2$, $R^1$ is methyl, $R^2$ is Cl, and $R^3$ is H.

Exemplary compounds of Formula (I) include, but are not limited to:

| Example | Structure |
|---------|-----------|
| 1 | 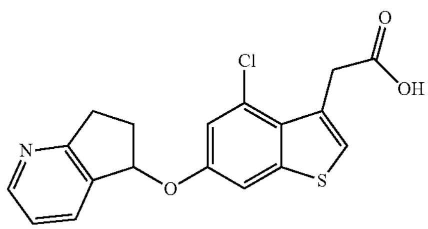 [SMILES: O=C(O)Cc1csc2cc(OC3CCc4ncccc43)cc(Cl)c12] |
| 2 | 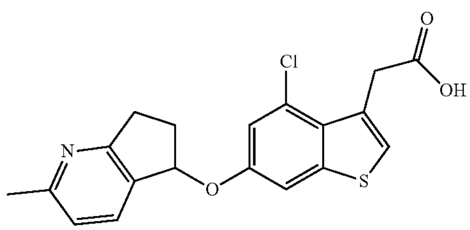 [SMILES: Cc1ccc2c(n1)CCC2Oc1cc(Cl)c2c(CC(=O)O)csc2c1] |
| 3 | 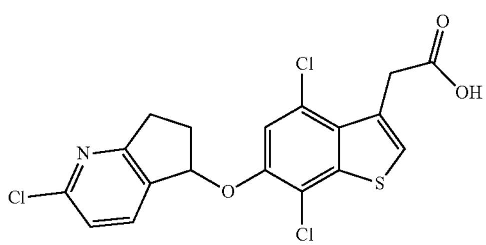 [SMILES: O=C(O)Cc1csc2c(Cl)c(OC3CCc4nc(Cl)ccc43)cc(Cl)c12] |
| 4 | 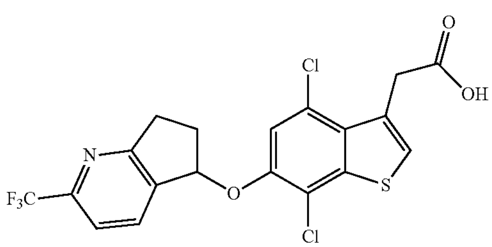 [SMILES: O=C(O)Cc1csc2c(Cl)c(OC3CCc4nc(C(F)(F)F)ccc43)cc(Cl)c12] |
| 5 | 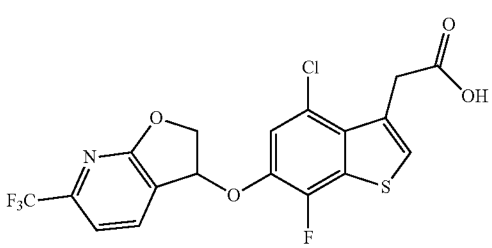 [SMILES: O=C(O)Cc1csc2c(F)c(OC3COc4nc(C(F)(F)F)ccc43)cc(Cl)c12] |
| 6 | |
| 7 | |
| 8 | |
| 9 | | and pharmaceutically acceptable salts thereof.

In one embodiment, this invention relates to compounds of Formula (II) represented by Formula (II):

(II)

wherein:

$R^1$ is hydrogen, halogen, cyano, ($C_1$-$C_4$)alkyl, halo($C_1$-$C_4$)alkyl, or —C(=O)$NH_2$;

X is $CH_2$ or O;

$R^2$ is halogen; and $R^3$ is hydrogen or halogen.

In certain embodiments, this invention relates to compounds of Formula (II), wherein:

$R^1$ is hydrogen, halogen, cyano, $(C_1$-$C_4)$alkyl, halo$(C_1$-$C_4)$alkyl, or —C(=O)N($R^a$)$_2$, wherein $R^a$ is hydrogen, substituted or unsubstituted $C_1$-$C_6$ alkyl, or a nitrogen protecting group;

X is $CH_2$ or O;

$R^2$ is halogen; and $R^3$ is hydrogen or halogen.

Formula (II) contains the substituent $R^1$. In certain embodiments, $R^1$ is H. In certain embodiments, $R^1$ is halogen. In certain embodiments, $R^1$ is Cl. In certain embodiments, $R^1$ is —CN. In certain embodiments, $R^1$ is —($C_1$-$C_4$)alkyl. In certain embodiments, $R^1$ is -Me. In certain embodiments, $R^1$ is -halo($C_1$-$C_4$)alkyl. In certain embodiments, $R^1$ is -$CF_3$. In certain embodiments, $R^1$ is —C(=O)NH$_2$. In certain embodiments, $R^1$ is —C(=O)N($R^a$)$_2$. In certain embodiments, $R^a$ is hydrogen. In certain embodiments, $R^a$ is substituted or unsubstituted $C_1$-$C_6$ alkyl. In certain embodiments, $R^a$ is -Me. In certain embodiments, $R^a$ is -Et. In certain embodiments, $R^a$ is a nitrogen protecting group.

Formula (II) contains the substituent X. In certain embodiments, X is $CH_2$. In certain embodiments, X is O.

Formula (II) contains the substituent $R^2$. In certain embodiments, $R^2$ is halogen. In certain embodiments, $R^2$ is —Cl.

Formula (II) contains the substituent $R^3$. In certain embodiments, $R^3$ is H. In certain embodiments, $R^3$ is halogen. In certain embodiments, $R^3$ is F. In certain embodiments, $R^3$ is Cl.

In certain embodiments, X is $CH_2$ and $R^1$ is methyl. In certain embodiments, $R^1$ is Me, $R^2$ is Cl, and $R^3$ is H. In certain embodiments, X is $CH_2$, $R^1$ is methyl, $R^2$ is Cl and $R^3$ is H.

Exemplary compounds of Formula (II) include, but are not limited to:

| Example | Structure |
| --- | --- |
| 1a | |
| 2a | |
| 3a | |
| 4a | 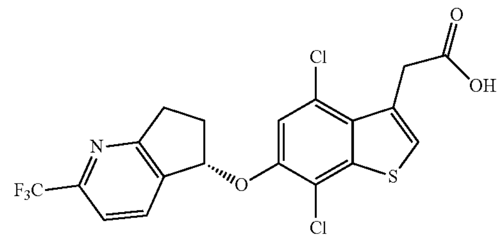 [SMILES: O=C(O)Cc1csc2c(Cl)c(O[C@H]3CCc4nc(C(F)(F)F)ccc43)cc(Cl)c12] |
| 5a | 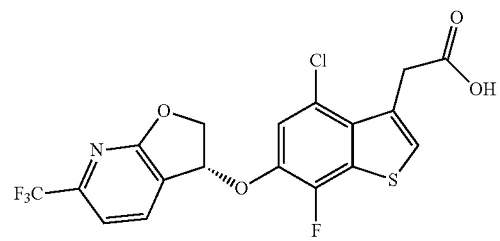 [SMILES: O=C(O)Cc1csc2c(F)c(O[C@H]3COc4nc(C(F)(F)F)ccc43)cc(Cl)c12] |
| 6a | 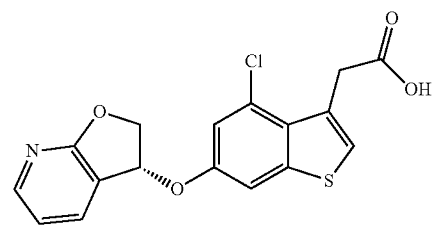 [SMILES: O=C(O)Cc1csc2cc(O[C@H]3COc4ncccc43)cc(Cl)c12] |
| 7a | 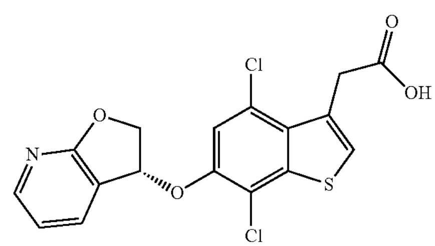 [SMILES: O=C(O)Cc1csc2c(Cl)c(O[C@H]3COc4ncccc43)cc(Cl)c12] |
| 8a | 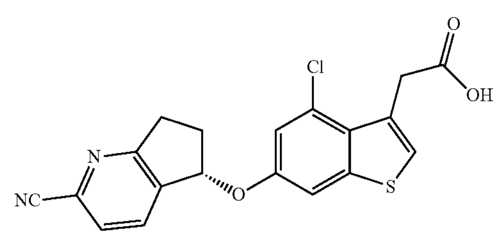 [SMILES: N#Cc1ccc2c(n1)CC[C@@H]2Oc1cc(Cl)c2c(CC(=O)O)csc2c1] |
| 9a | | and pharmaceutically acceptable salts thereof.

In certain embodiments, Formula (II) is of the formula:

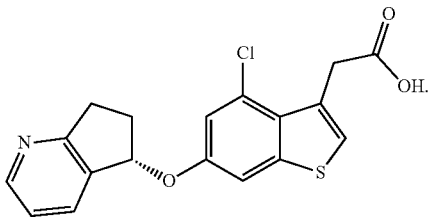 [SMILES: O=C(O)Cc1csc2cc(O[C@H]3CCc4ncccc43)cc(Cl)c12]

In certain embodiments, Formula (II) is of the formula

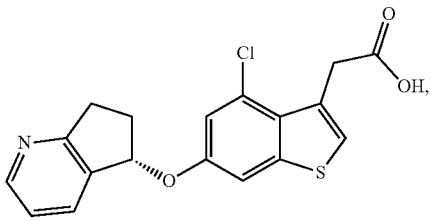 [SMILES: O=C(O)Cc1csc2cc(O[C@H]3CCc4ncccc43)cc(Cl)c12]

or a pharmaceutically acceptable salt thereof.

In another embodiment, this invention relates to compounds of Formula (I) represented by Formula (III):

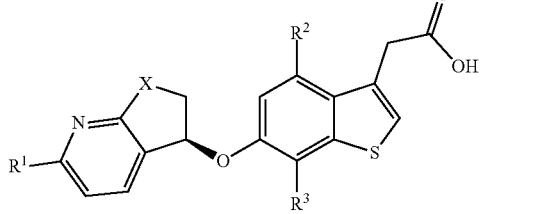

wherein:
$R^1$ is hydrogen, halogen, cyano, ($C_1$-$C_4$)alkyl, halo($C_1$-$C_4$)alkyl, or —C(=O)NH$_2$;
X is CH$_2$ or O;
$R^2$ is halogen; and
$R^3$ is hydrogen or halogen.

In another embodiment, this invention relates to compounds of Formula (III), wherein:
$R^1$ is hydrogen, halogen, cyano, ($C_1$-$C_4$)alkyl, halo($C_1$-$C_4$)alkyl, or —C(=O)N($R^a$)$_2$, wherein $R^a$ is hydrogen, substituted or unsubstituted $C_1$-$C_6$ alkyl, or a nitrogen protecting group;
X is CH$_2$ or O;
$R^2$ is halogen; and
$R^3$ is hydrogen or halogen.

Formula (III) contains the substituent $R^1$. In certain embodiments, $R^1$ is H. In certain embodiments, $R^1$ is halogen. In certain embodiments, $R^1$ is Cl. In certain embodiments, $R^1$ is —CN. In certain embodiments, $R^1$ is —($C_1$-$C_4$)alkyl. In certain embodiments, $R^1$ is -Me. In certain embodiments, $R^1$ is -halo($C_1$-$C_4$)alkyl. In certain embodiments, $R^1$ is —CF$_3$. In certain embodiments, $R^1$ is —C(=O)NH$_2$. In certain embodiments, $R^1$ is —C(=O)N($R^a$)$_2$. In certain embodiments, $R^a$ is hydrogen. In certain embodiments, $R^a$ is substituted or unsubstituted $C_1$-$C_6$ alkyl. In certain embodiments, $R^a$ is -Me. In certain embodiments, $R^a$ is -Et. In certain embodiments, $R^a$ is a nitrogen protecting group.

Formula (III) contains the substituent X. In certain embodiments, X is CH$_2$. In certain embodiments, X is O.

Formula (III) contains the substituent $R^2$. In certain embodiments, $R^2$ is halogen. In certain embodiments, $R^2$ is —Cl.

Formula (III) contains the substituent $R^3$. In certain embodiments, $R^3$ is H. In certain embodiments, $R^3$ is halogen. In certain embodiments, $R^3$ is F. In certain embodiments, $R^3$ is Cl.

In certain embodiments, X is CH$_2$ and $R^1$ is methyl. In certain embodiments, $R^1$ is Me, $R^2$ is Cl, and $R^3$ is H. In certain embodiments, X is CH$_2$, $R^1$ is methyl, $R^2$ is Cl and $R^3$ is H.

Exemplary compounds of Formula (III) include, but are not limited to:

| Example | Structure |
|---|---|
| 1b | 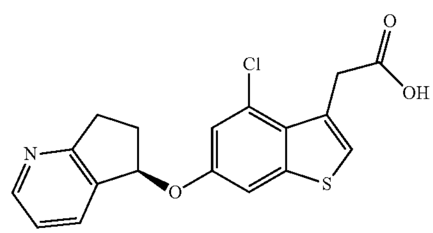 [SMILES: O=C(O)Cc1csc2cc(O[C@@H]3CCc4ncccc43)cc(Cl)c12] |
| 2b | 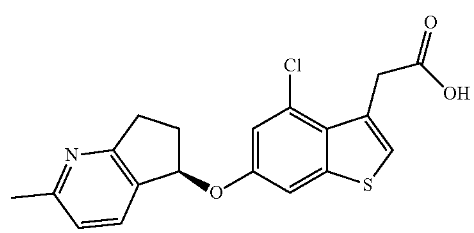 [SMILES: Cc1ccc2c(n1)CC[C@H]2Oc1cc(Cl)c2c(CC(=O)O)csc2c1] |
| 3b | 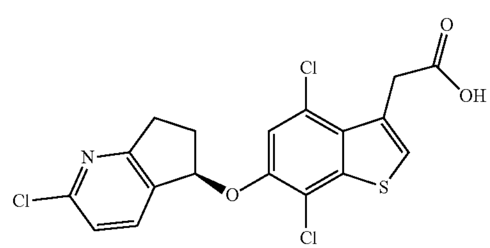 [SMILES: O=C(O)Cc1csc2c(Cl)c(O[C@@H]3CCc4nc(Cl)ccc43)cc(Cl)c12] |
| 4b | 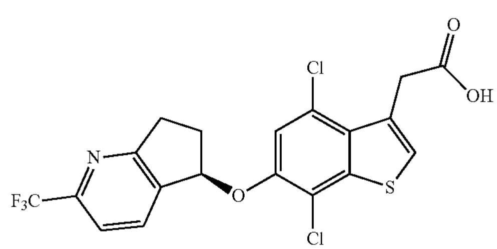 [SMILES: O=C(O)Cc1csc2c(Cl)c(O[C@@H]3CCc4nc(C(F)(F)F)ccc43)cc(Cl)c12] |

| Example | Structure |
|---|---|
| 5b | (structure: 4-chloro-7-fluoro-benzothiophene-3-acetic acid with 2,3-dihydrofuro[2,3-b]pyridine-6-CF3 ether linkage) |
| 6b | (structure: 4-chloro-benzothiophene-3-acetic acid with 2,3-dihydrofuro[2,3-b]pyridine ether linkage) |
| 7b | (structure: 4,7-dichloro-benzothiophene-3-acetic acid with 2,3-dihydrofuro[2,3-b]pyridine ether linkage) |
| 8b | (structure: 4-chloro-benzothiophene-3-acetic acid with 2-cyano-6,7-dihydro-5H-cyclopenta[b]pyridine ether linkage) |
| 9b | (structure: 4-chloro-benzothiophene-3-acetic acid with 2-carbamoyl-6,7-dihydro-5H-cyclopenta[b]pyridine ether linkage) | and pharmaceutically acceptable salts thereof.

Specific compounds of this invention include:

2-(4-chloro-6-((6,7-dihydro-5H-cyclopenta[b]pyridin-5-yl)oxy)benzo[b]thiophen-3-yl)acetic acid;

(R)-2-(4-chloro-6-((6,7-dihydro-5H-cyclopenta[b]pyridin-5-yl)oxy)benzo[b]thiophen-3-yl)acetic acid;

(S)-2-(4-chloro-6-((6,7-dihydro-5H-cyclopenta[b]pyridin-5-yl)oxy)benzo[b]thiophen-3-yl)acetic acid;

2-(4-chloro-6-((2-methyl-6,7-dihydro-5H-cyclopenta[b]pyridin-5-yl)oxy)benzo[b]thiophen-3-yl)acetic acid;

(R)-2-(4-chloro-6-((2-methyl-6,7-dihydro-5H-cyclopenta[b]pyridin-5-yl)oxy)benzo[b]thiophen-3-yl)acetic acid;

(S)-2-(4-chloro-6-((2-methyl-6,7-dihydro-5H-cyclopenta[b]pyridin-5-yl)oxy)benzo[b]thiophen-3-yl)acetic acid;

2-(4,7-dichloro-6-((2-chloro-6,7-dihydro-5H-cyclopenta[b]pyridin-5-yl)oxy)benzo[b]thiophen-3-yl)acetic acid;

(R)-2-(4,7-dichloro-6-((2-chloro-6,7-dihydro-5H-cyclopenta[b]pyridin-5-yl)oxy)benzo[b]thiophen-3-yl)acetic acid;

(S)-2-(4,7-dichloro-6-((2-chloro-6,7-dihydro-5H-cyclopenta[b]pyridin-5-yl)oxy)benzo[b]thiophen-3-yl)acetic acid;

2-(4,7-dichloro-6-((2-(trifluoromethyl)-6,7-dihydro-5H-cyclopenta[b]pyridin-5-yl)oxy)benzo[b]thiophen-3-yl)acetic acid;

(R)-2-(4,7-dichloro-6-((2-(trifluoromethyl)-6,7-dihydro-5H-cyclopenta[b]pyridin-5-yl)oxy)benzo[b]thiophen-3-yl)acetic acid;

(S)-2-(4,7-dichloro-6-((2-(trifluoromethyl)-6,7-dihydro-5H-cyclopenta[b]pyridin-5-yl)oxy)benzo[b]thiophen-3-yl)acetic acid;

2-(4-chloro-7-fluoro-6-((6-(trifluoromethyl)-2,3-dihydrofuro[2,3-b]pyridin-3-yl)oxy)benzo[b]thiophen-3-yl)acetic acid;

(R)-2-(4-chloro-7-fluoro-6-((6-(trifluoromethyl)-2,3-dihydrofuro[2,3-b]pyridin-3-yl)oxy)benzo[b]thiophen-3-yl)acetic acid;

(S)-2-(4-chloro-7-fluoro-6-((6-(trifluoromethyl)-2,3-dihydrofuro[2,3-b]pyridin-3-yl)oxy)benzo[b]thiophen-3-yl)acetic acid;

2-(4-chloro-6-((2,3-dihydrofuro[2,3-b]pyridin-3-yl)oxy)benzo[b]thiophen-3-yl)acetic acid;

(R)-2-(4-chloro-6-((2,3-dihydrofuro[2,3-b]pyridin-3-yl)oxy)benzo[b]thiophen-3-yl)acetic acid;

(S)-2-(4-chloro-6-((2,3-dihydrofuro[2,3-b]pyridin-3-yl)oxy)benzo[b]thiophen-3-yl)acetic acid;

2-(4,7-dichloro-6-((2,3-dihydrofuro[2,3-b]pyridin-3-yl)oxy)benzo[b]thiophen-3-yl)acetic acid;

(R)-2-(4,7-dichloro-6-((2,3-dihydrofuro[2,3-b]pyridin-3-yl)oxy)benzo[b]thiophen-3-yl)acetic acid;

(S)-2-(4,7-dichloro-6-((2,3-dihydrofuro[2,3-b]pyridin-3-yl)oxy)benzo[b]thiophen-3-yl)acetic acid;

2-(4-chloro-6-((2-cyano-6,7-dihydro-5H-cyclopenta[b]pyridin-5-yl)oxy)benzo[b]thiophen-3-yl)acetic acid;

(R)-2-(4-chloro-6-((2-cyano-6,7-dihydro-5H-cyclopenta[b]pyridin-5-yl)oxy)benzo[b]thiophen-3-yl)acetic acid;

(S)-2-(4-chloro-6-((2-cyano-6,7-dihydro-5H-cyclopenta[b]pyridin-5-yl)oxy)benzo[b]thiophen-3-yl)acetic acid;

2-(6-((2-carbamoyl-6,7-dihydro-5H-cyclopenta[b]pyridin-5-yl)oxy)-4-chlorobenzo[b]thiophen-3-yl)acetic acid;

(R)-2-(6-((2-carbamoyl-6,7-dihydro-5H-cyclopenta[b]pyridin-5-yl)oxy)-4-chlorobenzo[b]thiophen-3-yl)acetic acid; and (S)-2-(6-((2-carbamoyl-6,7-dihydro-5H-cyclopenta[b]pyridin-5-yl)oxy)-4-chlorobenzo[b]thiophen-3-yl)acetic acid;

and pharmaceutically acceptable salts thereof.

Typically, but not absolutely, the salts of the present invention are pharmaceutically acceptable salts. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

Other salts, which are not pharmaceutically acceptable, may be useful in the preparation, isolation, or storage of the compounds of this invention, and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) may exist in a crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that the compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The present invention is further directed to crystalline forms of (S)-2-(4-chloro-6-((6,7-dihydro-5H-cyclopenta[b]pyridin-5-yl)oxy)benzo[b]thiophen-3-yl)acetic acid.

In some embodiments, a crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern comprising at least nine diffraction angles, when measured using Cu K$_\alpha$ radiation, selected from a group consisting of about 5.9, 13.6, 14.0, 14.3, 21.9, 22.5, 23.1, 23.3, 24.1, 24.5, 24.7, 25.7, 26.1, 26.6, and 27.4 degrees 2θ. In another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 5.9, 13.6, 14.0, 14.3, 21.9, 22.5, 23.1, 23.3, 24.1, 24.5, 24.7, 25.7, 26.1, 26.6, and 27.4 degrees 2θ. In another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern comprising at least three diffraction angles, when measured using Cu K$_\alpha$ radiation, selected from a group consisting of about 5.9, 13.6, 14.0, 14.3, 21.9, 22.5, 23.1, 23.3, 24.1, 24.5, 24.7, 25.7, 26.1, 26.6, and 27.4 degrees 2θ.

In another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern comprising diffraction angles, when measured using Cu K$_\alpha$ radiation, of about 5.9, 13.6, 14.0, 14.3, 23.3, 24.5, and 27.4 degrees 2θ.

In yet another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern substantially in accordance with FIG. 1.

Figure 2:
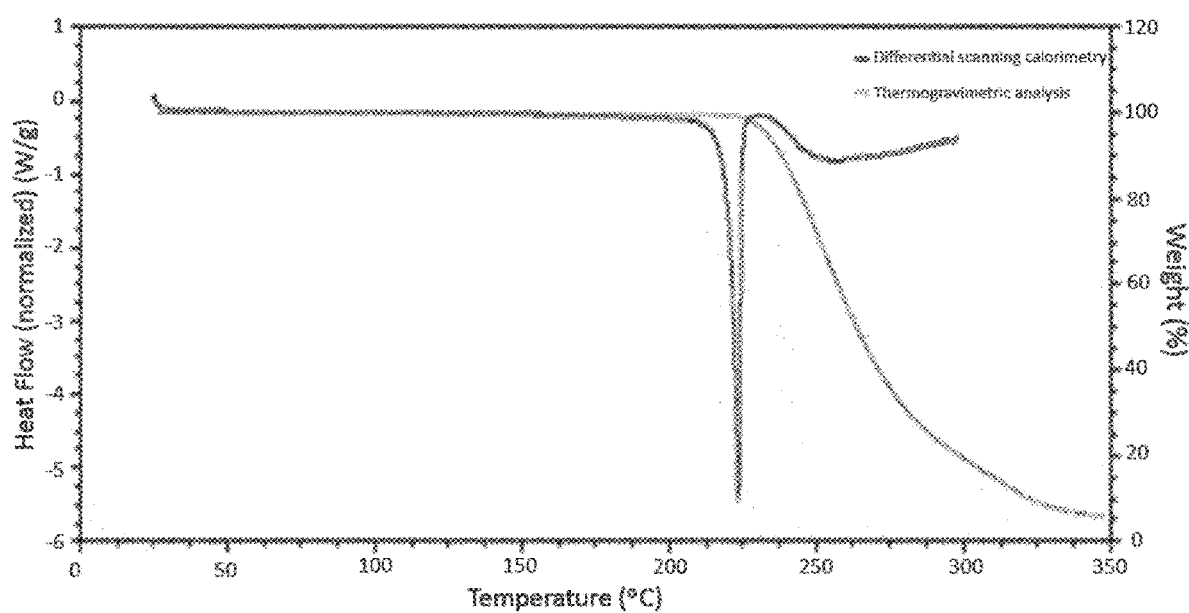

In further embodiments, the crystalline form of (S)-2-(4-chloro-6-((6,7-dihydro-5H-cyclopenta[b]pyridin-5-yl)oxy)benzo[b]thiophen-3-yl)acetic acid is characterized by a differential scanning calorimetry trace substantially in accordance with FIG. 2 and/or a thermogravimetric analysis trace substantially in accordance with FIG. 2.

In still further embodiments, as a person having ordinary skill in the art will understand, (S)-2-(4-chloro-6-((6,7-dihydro-5H-cyclopenta[b]pyridin-5-yl)oxy)benzo[b]thiophen-3-yl)acetic acid is characterized by any combination of the analytical data characterizing the aforementioned embodiments. For example, in one embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern substantially in accordance with FIG. 1 and a differential scanning calorimetry trace substantially in accordance with FIG. 2 and a thermogravimetric analysis trace substantially in accordance with FIG. 2. In another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern substantially in accordance with FIG. 1 and a differential scanning calorimetry trace substantially in accordance with FIG. 2 In another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern substantially in accordance with FIG. 1 and a thermogravimetric analysis trace substantially in accordance with FIG. 2. In another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern comprising diffraction angles, when measured using Cu $K_\alpha$ radiation, of about 5.9, 13.6, 14.0, 14.3, 23.3, 24.5, and 27.4 degrees 2θ, and a differential scanning calorimetry trace substantially in accordance with FIG. 2. In another embodiment, the crystalline form of (S)-2-(4-chloro-6-((6,7-dihydro-5H-cyclopenta[b]pyridin-5-yl)oxy)benzo[b]thiophen-3-yl)acetic acid is characterized by an X-ray powder diffraction (XRPD) pattern comprising diffraction angles, when measured using Cu $K_\alpha$ radiation, of about 5.9, 13.6, 14.0, 14.3, 23.3, 24.5, and 27.4 degrees 2θ, and a thermogravimetric analysis trace substantially in accordance with FIG. 2.

An XRPD pattern will be understood to comprise a diffraction angle (expressed in degrees 2θ) of "about" a value specified herein when the XRPD pattern comprises a diffraction angle within ±0.3 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1 provided herein is an XRPD pattern that would be considered by one skilled in the art to represent a compound possessing the same crystal form as the compound that provided the XRPD pattern of FIG. 1. That is, the XRPD pattern may be identical to that of FIG. 1, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of (S)-2-(4-chloro-6-((6,7-dihydro-5H-cyclopenta[b]pyridin-5-yl)oxy)benzo[b]thiophen-3-yl)acetic acid, with FIG. 1 and, using expertise and knowledge in the art, readily determine whether the XRPD pattern of the sample is substantially in accordance with the XRPD pattern of (S)-2-(4-chloro-6-((6,7-dihydro-5H-cyclopenta[b]pyridin-5-yl)oxy)benzo[b]thiophen-3-yl)acetic acid disclosed herein. If the XRPD pattern is substantially in accordance with FIG. 1, the sample form can be readily and accurately identified as having the same form as the crystalline form of (S)-2-(4-chloro-6-((6,7-dihydro-5H-cyclopenta[b]pyridin-5-yl)oxy) benzo[b]thiophen-3-yl)acetic acid disclosed herein.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labeled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

The invention further provides a pharmaceutical composition (also referred to as a pharmaceutical formulation) comprising a compound of Formula (I) or pharmaceutically acceptable salt thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

In the present invention, tablets and capsules are preferred for delivery of the pharmaceutical composition.

In accordance with another aspect of the invention there is provided a process for the preparation of a pharmaceutical composition comprising mixing (or admixing) a compound of Formula (I) or salt thereof with at least one excipient.

The present invention also provides a method of treatment in a mammal, especially a human. The compounds and compositions of the invention are used to treat GOAT mediated disorders or diseases. Disease states or disorders which can be treated by the methods and compositions provided herein include, but are not limited to, obesity The present invention also provides a method of treatment in a subject (e.g., a mammal, especially a human). Disease states or disorders which can be treated by the methods and compositions or preparations provided herein include, but are not limited to, metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.).

The compositions and methods provided herein are particularly deemed useful for the treatment of GOAT mediated disorders, such as obesity, increased adiposity, poor glycemic control, etc. The compositions and methods provided herein are particularly deemed useful for the treatment of GOAT mediated disorders, such as metabolic disorders (e.g. Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))), psychiatric disorders (e.g., eating disorders (e.g., bulimia nervosa, binge eating disorder, night-time eating syndrome), substance related disorders (e.g., addiction disorders (e.g., alcohol, smoking, overeating, or use of illicit drugs))), as well as disorders related to or complications of metabolic or psychiatric disorders (e.g., cardiovascular diseases (e.g., diabetic heart disease (e.g., diabetic cardiomyopathy), heart failure, or hypertension), ischemia (e.g., myocardial ischemia, cerebral ischemia, ischemic stroke), or BMI-related cancers (e.g., pancreatic cancer, gallbladder cancer, esophageal cancer, colorectal cancer, breast cancer etc.)). More particularly, diseases or disorders that may be treated by the compositions and methods of the invention include Prader-Willi syndrome, excess weight, and/or obesity (e.g., obesity caused by Prader-Willi syndrome). Weight that is higher than what is considered as a healthy weight for a given height is considered overweight or obese. In one embodiment, a compound of the invention is administered to a human having a body mass index (BMI) of at least about 25. In one embodiment, a compound of the invention is administered to a human having a body mass index (BMI) of at least about 26. In one embodiment, a compound of the invention is administered to a human having a body mass index (BMI) of at least about 27. In one embodiment, a compound of the invention is administered to a human having a body mass index (BMI) of at least about 28. In one embodiment, a compound of the invention is administered to a human having a body mass index (BMI) of at least about 29. In one embodiment, a compound of the invention is administered to a human having a body mass index (BMI) of at least about 30. In another embodiment, a compound of the invention is administered to a human having a body mass index (BMI) of at least about 31, at least about 32, at least about 33, at least about 34, at least about 35, at least about 36, at least about 37, at least about 38, at least about 39, or at least about 40. In one embodiment, the obesity is extreme or severe obesity. In a particular embodiment, the obesity is caused by Prader-Willi syndrome.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy, such as bariatric surgery. In one embodiment, combination therapies according to the invention comprise the administration of at least one compound of the invention and lifestyle modification. Lifestyle modification can include, for example, a reduced-calorie diet and/or exercise. In one embodiment, combination therapies according to the invention comprise the administration of at least one compound of the invention and a weight-loss agent, such as orlistat, lorcaserin, liraglutide, phentermine/topiramate, or naltrexone/bupropion. In one embodiment, combination therapies according to the invention comprise the administration of at least one compound of the invention and a hormone therapy (e.g., testosterone, estrogen, progesterone, or human growth hormone), selective serotonin reuptake inhibitors (SSRIs), or anti-diabetic therapy (e.g., insulin, miglitol, acarbose, metformin, exenatide, pramlintide). In yet another embodiment, the invention comprises a therapeutic regimen where the GOAT inhibitors of this disclosure are not in and of themselves active or significantly active, but when combined with another therapy, which may or may not be active as a standalone therapy, the combination provides a useful therapeutic outcome.

By the term "co-administration" and derivatives thereof as used herein refers to either simultaneous administration or any manner of separate sequential administration of a GOAT inhibiting compound, as described herein, and a further active ingredient or ingredients, known to be useful in the treatment of obesity, including orlistat, lorcaserin, liraglutide, phentermine/topiramate, and naltrexone/bupropion, or a hormone therapy (e.g., testosterone, estrogen, progesterone, or human growth hormone), selective serotonin reuptake inhibitors (SSRIs), or anti-diabetic therapy (e.g., insulin, miglitol, acarbose, metformin, exenatide, pramlintide). The term further active ingredient or ingredients, as used herein, includes any compound or therapeutic agent known to or that demonstrates advantageous properties when administered to a patient in need of treatment for obesity. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any weight loss agent may be co-administered in the treatment of obesity in the present invention. Typically, any weight loss agent, hormone therapy, or anti-diabetic therapy may be co-administered in the methods and uses of the present invention. A person of ordinary skill in the art would be able to discern which combinations of agents would be useful based on the particular characteristics of the drugs and the obesity involved. Typical weight loss agents useful in the present invention include, but are not limited to, appetite-suppressing agents and lipase inhibitors.

Examples of a further active ingredient or ingredients for use in combination or co-administered with the present GOAT inhibiting compounds are weight-loss agents. Examples of weight-loss agents include, but are not limited to, orlistat, lorcaserin, liraglutide, phentermine/topiramate, and naltrexone/bupropion.

Orlistat is a lipase inhibitor which prevents some of the fat in foods eaten from being absorbed in the intestines. The unabsorbed fat is removed from the body in the stool.

Lorcaserin (BELVIQ) is a serotonin receptor agonist. Lorcaserin targets the 5HT2C receptor and alters body weight by regulating satiety.

Liraglutide (SAXENDA) is a glucagonlike peptide-1 (GLP-1) receptor agonist. Liraglutide is an anti-diabetic agent that has been approved for weight loss.

Phentermine/Topimarate (QYSMIA) is a combination product. Phentermine is an anorectic and topiramate is an anticonvulsant. Phentermine/Topimarate decreases appetite and causes feelings of fullness to last longer after eating.

Naltrexone/Bupropion (CONTRAVE) is a combination product. Naltrexone is an opiate antagonist and Bupropion is an antidepressant. Naltrexone/Bupropion regulates brain activity to reduce appetite.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formula (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of Formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavoring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of Formula (I) for the treatment of obesity will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of Formula (I) per se. It is envisaged that similar dosages would be appropriate for treatment of the other conditions referred to above.

In certain embodiments, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid. In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid wherein at least 10% by weight of (S)-2-(4-chloro-6-((6,7-dihydro-5H-cyclopenta[b]pyridin-5-yl)oxy)benzo[b]thiophen-3-yl)acetic acid is present as the crystalline form of (S)-2-(4-chloro-6-((6,7-dihydro-5H-cyclopenta[b]pyridin-5-yl)oxy)benzo[b]thiophen-3-yl)acetic acid described herein. In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid wherein at least 20% by weight, or at least 30% by weight, or at least 40% by weight, or at least 50% by weight, or at least 60% by weight, or at least 70% by weight, or at least 80% by weight, or at least 90% by weight of (S)-2-(4-chloro-6-((6,7-dihydro-5H-cyclopenta[b]pyridin-5-yl)oxy)benzo[b]thiophen-3-yl)acetic acid is present as the crystalline form of (S)-2-(4-chloro-6-((6,7-dihydro-5H-cyclopenta[b]pyridin-5-yl)oxy)benzo[b]thiophen-3-yl)acetic acid described herein. In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid wherein at least 95% by weight, or at least 96% by weight, or at least 97% by weight, or at least 98% by weight, or at least 99% by weight, or at least 99.5% by weight, or at least 99.8% by weight, or at least 99.9% by weight of (S)-2-(4-chloro-6-((6,7-dihydro-5H-cyclopenta[b]pyridin-5-yl)oxy)benzo[b]thiophen-3-yl)acetic acid is present as the crystalline form of (S)-2-(4-chloro-6-((6,7-dihydro-5H-cyclopenta[b]pyridin-5-yl)oxy)benzo[b]thiophen-3-yl)acetic acid described herein.

In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid, wherein not more than 90% by weight of the compound is amorphous. In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid, wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the compound is amorphous. In another embodiment, this invention relates to a pharmaceutical composition comprising (S)-2-(4-chloro-6-((6,7-dihydro-5H-cyclopenta[b]pyridin-5-yl)oxy)benzo

[b]thiophen-3-yl)acetic acid, wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the compound is amorphous.

In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid wherein not more than 90% by weight of the (S)-2-(4-chloro-6-((6,7-dihydro-5H-cyclopenta[b]pyridin-5-yl)oxy)benzo[b]thiophen-3-yl)acetic acid is present in a form other than the crystalline form of (S)-2-(4-chloro-6-((6,7-dihydro-5H-cyclopenta[b]pyridin-5-yl)oxy)benzo[b]thiophen-3-yl)acetic acid described herein. In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of (S)-2-(4-chloro-6-((6,7-dihydro-5H-cyclopenta[b]pyridin-5-yl)oxy)benzo[b]thiophen-3-yl)acetic acid is present in a form other than the crystalline form of (S)-2-(4-chloro-6-((6,7-dihydro-5H-cyclopenta[b]pyridin-5-yl)oxy)benzo[b]thiophen-3-yl)acetic acid described herein. In another embodiment, this invention relates to a pharmaceutical composition comprising (S)-2-(4-chloro-6-((6,7-dihydro-5H-cyclopenta[b]pyridin-5-yl)oxy)benzo[b]thiophen-3-yl)acetic acid wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of (S)-2-(4-chloro-6-((6,7-dihydro-5H-cyclopenta[b]pyridin-5-yl)oxy)benzo[b]thiophen-3-yl)acetic acid is present in a form other than the crystalline form of (S)-2-(4-chloro-6-((6,7-dihydro-5H-cyclopenta[b]pyridin-5-yl)oxy)benzo[b]thiophen-3-yl)acetic acid described herein.

Definitions

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "($C_1$-$C_4$)alkyl" refers to an alkyl moiety containing from 1 to 4 carbon atoms. Exemplary alkyls include, but are not limited to, methyl, ethyl, n-propyl, isopropyl, n-butyl, isobutyl, s-butyl, and t-butyl.

The term "halo($C_1$-$C_4$)alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo($C_1$-$C_4$)alkyl" groups useful in the present invention include, but are not limited to, —$CF_3$ (trifluoromethyl), —$CCl_3$ (trichloromethyl), 1,1-difluoroethyl, 2-fluoro-2-methylpropyl, 2,2-difluoropropyl, 2,2,2-trifluoroethyl, and hexafluoroisopropyl.

The terms "halogen" and "halo" represent fluoro, chloro, bromo, or iodo substituents.

As used herein, the term "cyano" refers to the group —CN.

In certain embodiments, the substituent present on the nitrogen atom is an nitrogen protecting group (also referred to herein as an "amino protecting group"). Nitrogen protecting groups include, but are not limited to, —OH, —ORaa, —N(Rcc)2, —C(=O)Raa, —C(=O)N(Rcc)2, —CO2Raa, —SO2Raa, —C(=NRcc)Raa, —C(=NRcc)ORaa, —C(=NRcc)N(Rcc)2, —SO2N(Rcc)2, —SO2Rcc, —SO2ORcc, —SORaa, —C(=S)N(Rcc)2, —C(=O)SRcc, —C(=S)SRcc, $C_1$-10 alkyl (e.g., aralkyl, heteroaralkyl), $C_2$-10 alkenyl, $C_2$-10 alkynyl, heteroC1-10alkyl, heteroC2-10alkenyl, heteroC2-10alkynyl, $C_3$-10 carbocyclyl, 3-14 membered heterocyclyl, $C_6$-14 aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 Rdd groups, and wherein Raa, Rbb, Rcc and Rdd are as described herein. Nitrogen protecting groups are well known in the art and include those described in detail in Protecting Groups in Organic Synthesis, T. W. Greene and P. G. M. Wuts, 3rd edition, John Wiley & Sons, 1999, incorporated herein by reference.

For example, nitrogen protecting groups such as amide groups (e.g., —C(=O)Raa) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)ORaa) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)2Raa) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound. These pharmaceutically acceptable salts may be prepared in situ during the final isolation and purification of the compound, or by separately reacting the purified compound in its free acid or free base form with a suitable base or acid, respectively. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutyrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates. Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl) amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

As used herein, the term "compound(s) of the invention" means a compound of Formula (I) (as defined above) in any form, i.e., any salt or non-salt form (e.g., as a free acid or base form, or as a pharmaceutically acceptable salt thereof)

and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

As used herein, the terms "treatment", "treat," and "treating" refer to reversing, alleviating the specified condition, eliminating or reducing one or more symptoms of the condition, delaying the onset of, slowing or eliminating the progression of the condition, and delaying the reoccurrence of a condition in a previously afflicted or diagnosed patient or subject. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

A "subject" to which administration is contemplated refers to a human (i.e., male or female of any age group, e.g., paediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog). The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "condition," "disease," and "disorder" are used interchangeably.

As used herein, the term "effective amount" means that amount of a drug or pharmaceutical agent that will elicit the biological or medical response of a tissue, system, animal, or human that is being sought, for instance, by a researcher or clinician. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

The term "therapeutically effective amount" of a compound described herein is any amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition as compared to a corresponding subject who has not received such amount, resulting in improved treatment, healing, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition or preparation. Additionally, the active ingredient or salt thereof may be presented as a pharmaceutical composition or preparation. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibition of GOAT in a subject, biological sample, tissue, or cell.

As used herein the term "inhibit" or "inhibition" in the context of proteins, for example, in the context of GOAT, refers to a reduction in the activity of the enzyme. In some embodiments, the term refers to a reduction of the level of activity, e.g., GOAT activity, to a level that is statistically significantly lower than an initial level, which may, for example, be a baseline level of activity. In some embodiments, the term refers to a reduction of the level of enzyme activity, e.g., GOAT activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

Pharmaceutical compositions or preparations described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, Prader-Willi syndrome, metabolic syndrome, insulin resistance, impaired glucose tolerance, prediabetes, diabetes mellitus (e.g., type II diabetes mellitus), dysglycemia (e.g., hyperglycemia), obesity (e.g., obesity caused by Prader-Willi syndrome), increased adiposity, poor glycemic control, hyperphagia, impaired satiety, dyslipidemia (e.g., atherogenic dyslipidemia), hepatic steatosis (e.g., non-alcoholic fatty liver disease (e.g., non-alcoholic steatohepatitis))).

A "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type II diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes. All forms of diabetes increase the risk of long-term complications. These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D.C. (1994). Psychiatric disorders include, but are not limited to, eating disorders (e.g., night eating syndrome), substance-related disorders (e.g., alcohol dependence, amphetamine dependence, *cannabis* dependence, cocaine dependence, hallucinogen dependence, inhalant dependence, nicotine dependence, opioid dependence, phencyclidine dependence, and sedative dependence).

An "obesity-related condition" includes, but is not limited to, Prader-Willi syndrome, obesity, undesired weight gain (e.g., from medication-induced weight gain, from cessation of smoking) and an over-eating disorder (e.g., binge eating, bulimia, compulsive eating, or a lack of appetite control each of which can optionally lead to undesired weight gain or obesity). "Obesity" and "obese" refers to class I obesity, class II obesity, class III obesity, and pre-obesity (e.g., being "over-weight") as defined by the World Health Organization.

Reduction of storage fat is expected to provide various primary and/or secondary benefits in a subject (e.g., in a subject diagnosed with a complication associated with obesity) such as, for example, an increased insulin responsiveness (e.g., in a subject diagnosed with Type II diabetes mellitus); a reduction in elevated blood pressure; a reduction in elevated cholesterol levels; and/or a reduction (or a reduced risk or progression) of ischemia (e.g., ischemic heart disease, cerebral ischemia, or ischemic stroke) arterial vascular disease, angina, myocardial infarction, stroke, migraines, congestive heart failure, deep vein thrombosis, pulmonary embolism, gall stones, gastroesophagael reflux disease, obstructive sleep apnea, obesity hypoventilation syndrome, asthma, gout, poor mobility, back pain, erectile dysfunction, urinary incontinence, liver injury (e.g., fatty liver disease, liver cirrhosis, alcoholic cirrhosis, endotoxin mediated liver injury) or chronic renal failure. Thus, the method of this invention is applicable to obese subjects, diabetic subjects, and alcoholic subjects.

| Abbreviations | Compound Preparation |
|---|---|
| AcOEt | ethyl acetate |
| AcOH | acetic acid |
| ADDP | 1,1'-(azodicarbonyl)dipiperidine |
| Ar | Ar gas |
| aq | aquaeous |
| $BBr_3$ | boron tribromide |
| Boc | tert-butyloxycarbonyl |
| $Bu_4NCl$ | tetrabutylammonium chloride |
| $CDCl_3$ | deuterochloroform |
| CHAPS | 3-[(3-cholamidopropyl)dimethylammonio]-1-propanesulfonate hydrate |
| $CH_3CN$ | acetonitrile |
| $Cs_2CO_3$ | cesium carbonate |
| DCE | 1,2-dichloroethane |
| DCM | dichloromethane |
| DIAD | diisopropyl azodicarboxylate |
| DIPEA | N,N-diisopropylethylamine |
| DM water | demineralized water |
| DMA | dimethylacetamide |
| DME | 1,2-dimethoxyethane |
| DMF | N,N-dimethylformamide |
| DMSO | dimethyl sulfoxide |
| DMPU | N,N'-dimethylpropylene urea |
| EDC | 1-ethyl-3-(3-dimethylaminopropyl)carbodiimide |
| EDTA | ethylenediaminetetraacetic acid |
| ES | electrospray |
| $Et_3N$ | triethylamine |
| $Et_2O$ | diethyl ether |
| EtOAc | ethyl acetate |
| EtOH | ethanol |
| h | hour(s) |
| $H_2$ | hydrogen gas |
| HCl | hydrochloric acid |
| $H_2O$ | water |
| HOAt | 1-hydroxy-7-azabenzotriazole |
| $H_2SO_4$ | sulfuric acid |
| HPLC | high-performance liquid chromatography |
| HTRF | homogeneous time resolved fluorescence |
| KOtBu | potassium tert-butoxide |
| $K_2CO_3$ | potassium carbonate |
| $KMnO_4$ | potassium permanganate |
| LCMS | liquid chromatography mass spectrometry |
| $LiAlH_4$ | lithium aluminum hydride |
| LiOH | lithium hydroxide |
| MeI | methyl iodide |
| MeOH | methanol |
| $MeSO_3H$ | methanesulfonic acid |
| $MgSO_4$ | magnesium sulfate |
| MOPS | 3-(N-morpholino)propanesulfonic acid |
| min | minute(s) |

| Abbreviations | Compound Preparation |
|---|---|
| M | molar |
| MS | mass spectrometry |
| MTBE | methyl tert-butyl ether |
| N | normal |
| $N_2$ | nitrogen gas |
| $NaBH_4$ | sodium borohydride |
| $NaBH(OAc)_3$ | sodium triacetoxyborohydride |
| $Na_2CO_3$ | sodium carbonate |
| NaH | sodium hydride |
| $NaHCO_3$ | sodium bicarbonate |
| NaHMDS | sodium bis(trimethylsilyl)amide |
| NaOH | sodium hydroxide |
| NaOMe | sodium methoxide |
| $Na_2SO_4$ | sodium sulfate |
| $(n-Bu)_3P$ | tri-n-butylphosphine |
| NBS | N-bromosuccinimide |
| $NH_4Cl$ | ammonium chloride |
| $NH_4OAc$ | ammonium acetate |
| $NH_4OH$ | ammonium hydroxide |
| NMM | N-methylmorpholine |
| Pd-C | palladium on carbon |
| $[PdCl(allyl)]_2$ | allylpalladium(II) chloride dimer |
| $Pd(OAc)_2$ | palladium(II) acetate |
| $Pd(PPh_3)_4$ | tetrakis(triphenylphosphine)palladium(0) |
| $Pd_2(dba)_3$ | tris(dibenzylideneacetone)dipalladium(0) |
| PLM | polarized light microscopy |
| Pet ether | petroleum ether |
| $P(o-tol)_3$ | tri(o-tolyl)phosphine |
| $POBr_3$ | phosphorus(V) oxybromide |
| RB | round bottom |
| RT or r.t. | room temperature |
| RuCl[R,R)-Tsdpen](mesitylene) | [N-[(1R,2R)-2-(Amino-κN)-1,2-diphenylethyl]-4-methylbenzenesulfonamidato-κN]chloro[(1,2,3,4,5,6-η)-1,3,5-trimethylbenzene]-ruthenium |
| sat. | saturated |
| SFC | supercritical fluid chromatography |
| $SOCl_2$ | thionyl chloride |
| tBuOH | tert-butanol |
| TBME | tert-butyl methyl ether |
| TEA | triethylamine |
| TFA | trifluoroacetic acid |
| THF | tetrahydrofuran |
| TLC | thin layer chromatography |
| TRF | time resolved fluorescence |
| xantphos | 4,5-bis(diphenylphosphino)-9,9-dimethylxanthene |
| $Zn(CN)_2$ | zinc cyanide |

Generic Synthesis Schemes

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention. Starting materials are commercially available or are made from commercially available starting materials using methods known to those skilled in the art.

Certain compounds of Formula (I) can be prepared according to Scheme-10 or analogous methods. Alkylation of a substituted 6-hydroxybenzo[b]thiophene with an optionally substituted 5-halo-6,7-dihydro-5H-cyclopenta[b]pyridine or an optionally substituted 3-chloro-2,3-dihydrofuro[2,3-b]pyridine is followed by saponification of the intermediate ester to afford compounds of Formula (I).

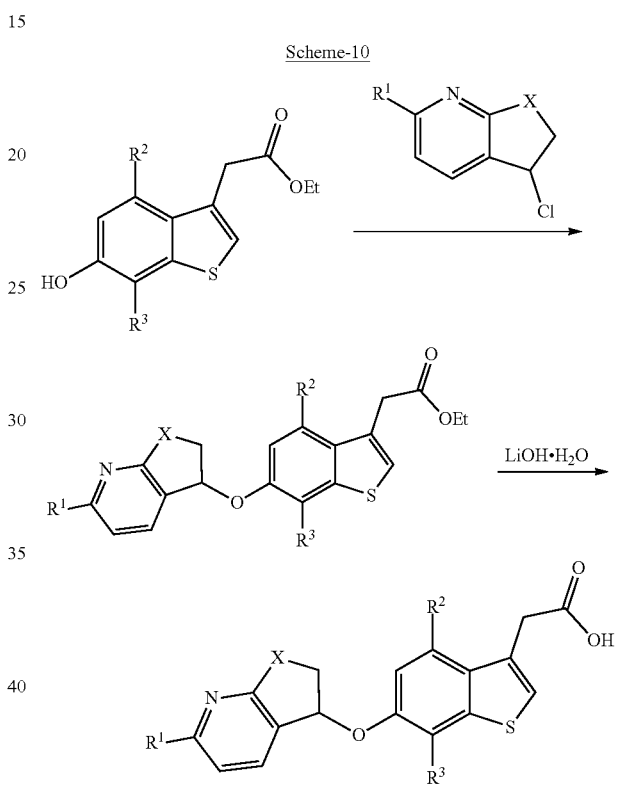

Scheme-10

Certain compounds of Formula (I) can be prepared according to Scheme-11 or analogous methods. A Mitsunobu reaction involving a substituted 6-hydroxybenzo[b]thiophene and an optionally substituted 6,7-dihydro-5H-cyclopenta[b]pyridin-5-ol or an optionally substituted 2,3-dihydrofuro[2,3-b]pyridin-3-ol is followed by saponification of the intermediate ester to afford compounds of Formula (I).

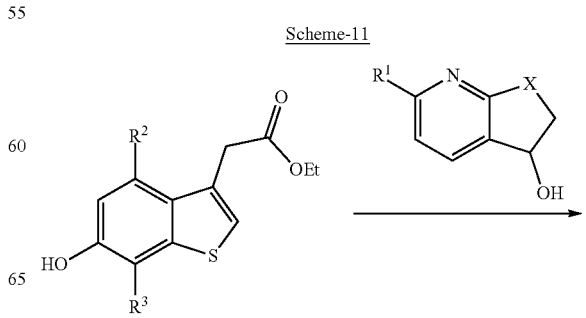

Scheme-11

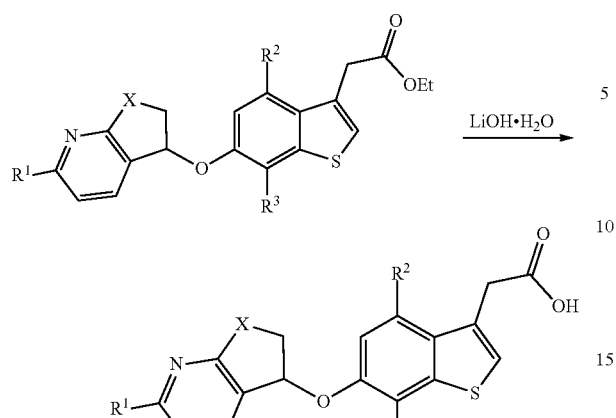

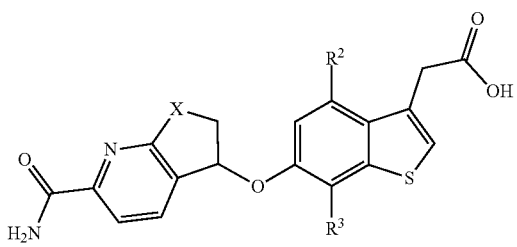

EXPERIMENTALS

Intermediates

Certain compounds of Formula (I) can be prepared according to Scheme-12 or analogous methods. Alkylation of a substituted 6-hydroxybenzo[b]thiophene with 2,5-dihalo-6,7-dihydro-5H-cyclopenta[b]pyridine or 3,6-dihalo-2,3-dihydrofuro[2,3-b]pyridine followed by a palladium-mediated cyanation provides the nitrile. Saponification of the intermediate ester followed by hydrolysis of the nitrile affords compounds of Formula (I).

Scheme-12

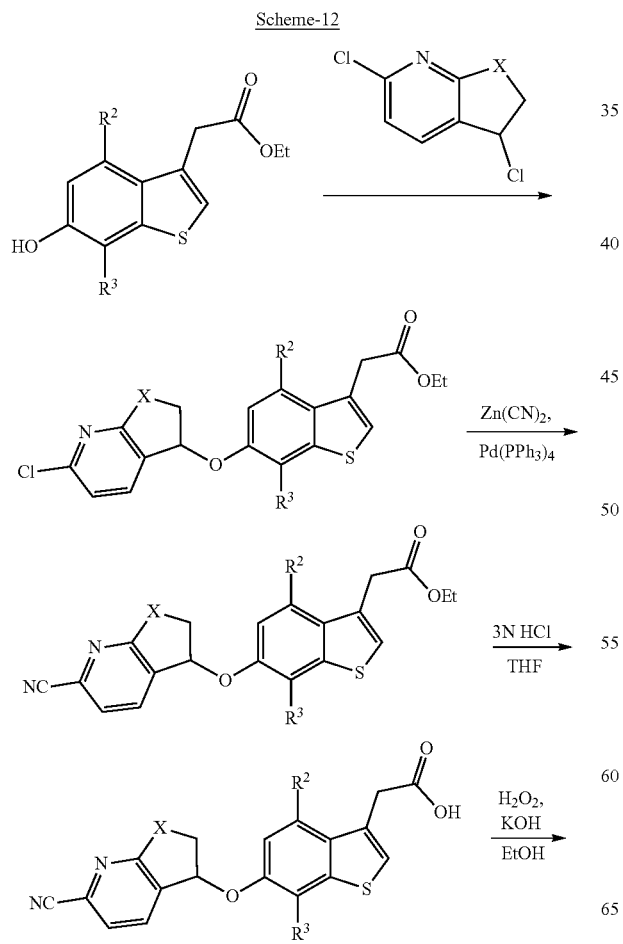

Scheme-1

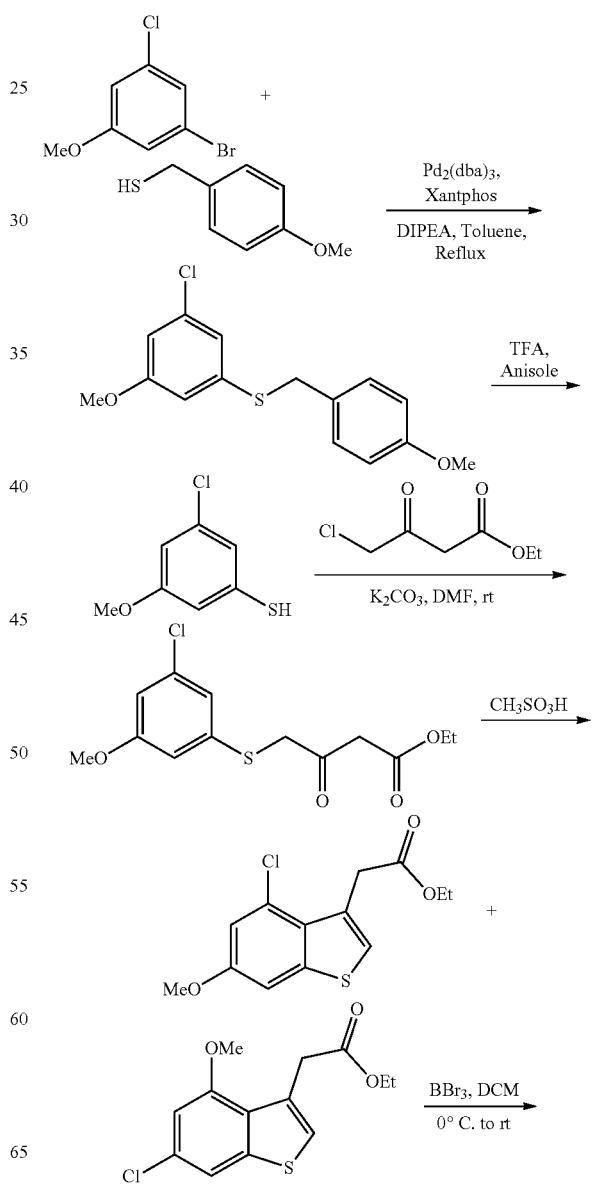

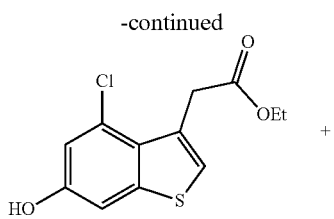

+

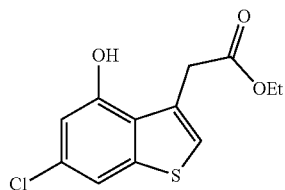

a)
(3-Chloro-5-methoxyphenyl)(4-methoxybenzyl)sulfane

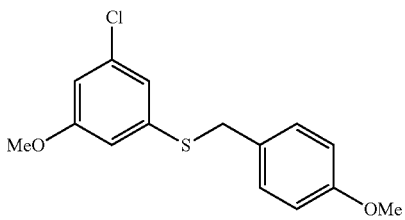 [SMILES: COc1ccc(CSc2cc(Cl)cc(OC)c2)cc1]

To a mixture of DIPEA (369 mL, 2113 mmol), xantphos (20.38 g, 35.2 mmol), 1-bromo-3-chloro-5-methoxybenzene (156 g, 704 mmol), (4-methoxyphenyl)methanethiol (109 g, 704 mmol) in toluene (500 mL) was added $Pd_2(dba)_3$ (32.2 g, 35.2 mmol) at room temperature and reaction mixture was refluxed for 5 h. After cooling, water was added to the mixture and extracted with EtOAc. The organic layer was separated, washed with brine, dried over $Na_2SO_4$ and concentrated in vacuo. The residue was purified by silica gel column chromatography (EtOAc/hexane) to give the title compound (yield 170.0 g) as a pale yellow liquid. $^1$H NMR (400 MHz, $CDCl_3$) δ 7.25-7.22 (m, 2H), 6.87-6.82 (m, 3H), 6.69-6.67 (m, 2H), 4.08 (s, 2H), 3.78 (s, 3H), 3.73 (s, 3H). LCMS (ES) m/z 293 [M+H]$^+$.

b) 3-Chloro-5-methoxybenzenethiol

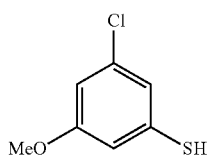

TFA (180 ml, 2336 mmol) was added to the solution of (3-chloro-5-methoxyphenyl)(4-methoxybenzyl)sulfane (180 g, 611 mmol) in anisole (180 mL) at 0° C. The reaction was stirred at 85° C. for 2 h under nitrogen atmosphere. Reaction mixture was quenched with 6N NaOH solution and extracted with EtOAc. The aqueous layer was acidified with 2N HCl and extracted with EtOAc. The EtOAc layer was washed with water and brine, dried over anhydrous $Na_2SO_4$, filtered and the filtrate was evaporated under reduced pressure to get crude residue. The residue was purified by silica gel column chromatography (EtOAc/hexane) to give the title compound (yield 80.0 g) as pale yellow liquid. LCMS (ES) m/z 172.88 [M+H]$^+$.

c) Ethyl 4-((3-chloro-5-methoxyphenyl)thio)-3-oxobutanoate

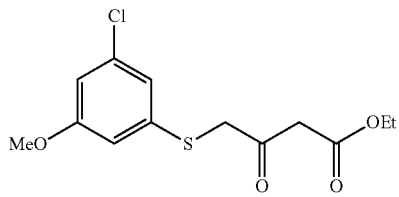 [SMILES: CCOC(=O)CC(=O)CSc1cc(Cl)cc(OC)c1]

To a mixture of 3-chloro-5-methoxybenzenethiol (80 g, 458 mmol) and dry DMF (500 mL) were added $K_2CO_3$ (63.3 g, 458 mmol) and ethyl 4-chloro-3-oxobutanoate (75 g, 458 mmol) at 0° C. The mixture was stirred at room temperature for 3 h. The mixture was diluted with water and extracted with EtOAc. The organic layer was washed successively with water and brine, dried over $MgSO_4$, and concentrated in vacuo to get crude product (100 g). This was used for the next step without any further purification.

d) Ethyl 2-(4-chloro-6-methoxybenzo[b]thiophen-3-yl)acetate and Ethyl 2-(6-chloro-4-methoxybenzo[b]thiophen-3-yl)acetate

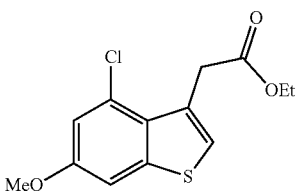

+

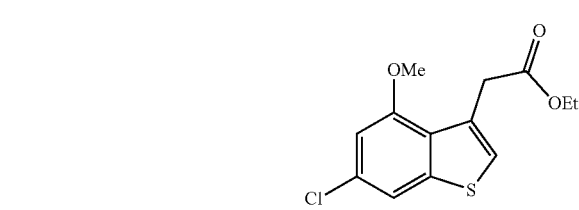

To ethyl 4-((3-chloro-5-methoxyphenyl)thio)-3-oxobutanoate (100 g, 330 mmol) was added methanesulfonic acid (500 mL) at 0° C. The mixture was stirred at 0° C. under nitrogen atmosphere for 15 min. The mixture was poured into water and extracted with EtOAc. The organic layer was washed with brine, dried over $MgSO_4$, and concentrated in vacuo. The residue was purified by silica gel column chromatography (EtOAc/hexane) to give the mixture of isomers (60 g, ratio 2.5:1) as colorless oil and used for the next step. LCMS (ES) m/z 285.16 [M+H]$^+$.

e) Ethyl 2-(4-chloro-6-hydroxybenzo[b]thiophen-3-yl)acetate and ethyl 2-(6-chloro-4-hydroxybenzo[b]thiophen-3-yl)acetate

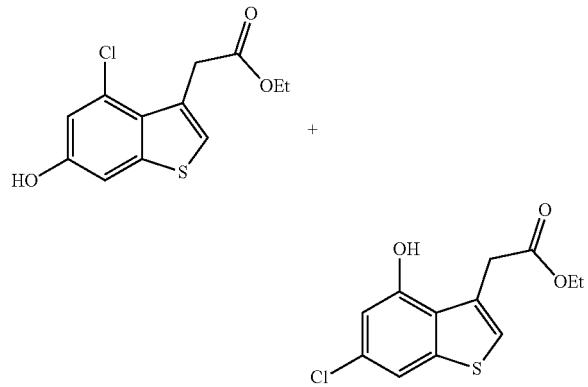

To a solution of ethyl 2-(4-chloro-6-methoxybenzo[b]thiophen-3-yl)acetate (60 g, 211 mmol) in DCM (500 mL) was added BBr₃ (29.9 mL, 316 mmol) at 0° C. The mixture was warmed to room temperature and continued stirring for 6 h at RT. The mixture was quenched with water and NaHCO₃ solution, and extracted with EtOAc. The organic layer was washed with brine, dried over Na₂SO₄, and concentrated in vacuo. The residue was purified by silica gel column chromatography (EtOAc/hexane) to give 27 g of ethyl 2-(4-chloro-6-hydroxybenzo[b]thiophen-3-yl)acetate) as white solid and 5.8 g of ethyl 2-(6-chloro-4-hydroxybenzo[b]thiophen-3-yl)acetate).

Ethyl 2-(4-chloro-6-hydroxybenzo[b]thiophen-3-yl)acetate (Desired Compound): $^1$H NMR (300 MHz, CDCl₃) δ 7.07 (s, 1H), 6.95 (d, J=2.4 Hz, 1H), 6.77 (d, J=2.4 Hz, 1H), 5.72 (s, 1H), 4.24 (q, J=9.2 Hz, 2H), 4.08 (s, 2H), 1.30 (t, J=6.9 Hz, 3H). LCMS (ES) m/z 271.12 (M+H)$^+$.

Ethyl 2-(6-chloro-4-hydroxybenzo[b]thiophen-3-yl)acetate (regioisomer Compound): $^1$H NMR (300 MHz, CDCl₃) δ 7.07 (s, 1H), 7.01 (d, J=0.9 Hz, 1H), 6.81 (d, J=1.2 Hz, 1H), 5.45 (s, 1H), 4.23 (q, J=7.2 Hz, 2H), 4.08 (s, 2H), 1.29 (t, J=7.2 Hz, 3H). LCMS (ES) m/z 270.93 (M+H)$^+$.

Scheme-2

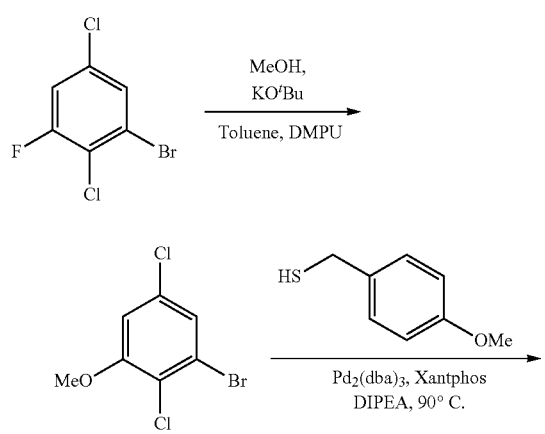

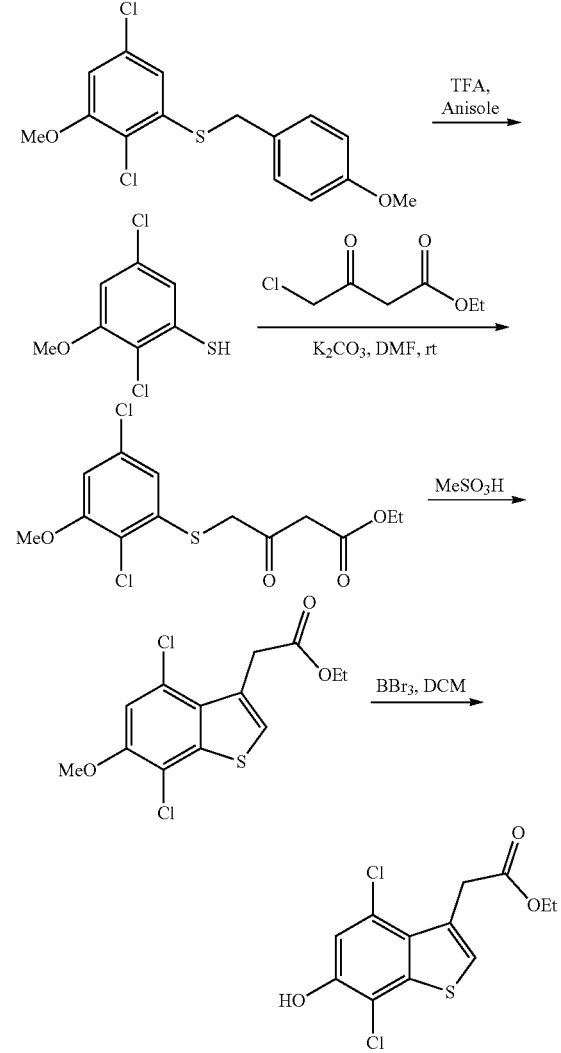

a) 1-Bromo-2,5-dichloro-3-methoxybenzene

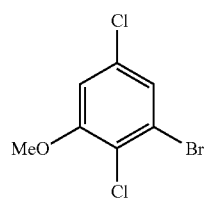 [SMILES: COc1cc(Cl)cc(Br)c1Cl]

To a solution of potassium KO$^t$Bu (20.7 g, 185 mmol)) suspended in toluene (270 mL) and DMPU (90 mL, 746 mmol) was added methanol (30 mL). The mixture was placed in an oil bath at 80° C. under N₂ with a reflux condenser for 25 minutes to obtain a solution. The solution was then allowed to cool to room temperature under N₂, after which 1-bromo-2,5-dichloro-3-fluorobenzene (15 g, 61.5 mmol) was added dropwise to the solution and the resulting suspension was placed in an oil bath at 80° C. under N₂. After 4 h, the reaction mixture was allowed to cool to room temperature and was then diluted with hexanes (200 mL) and water. The layers were separated and the aqueous layer was extracted with hexanes. The combined organic portions were washed with water, dried (MgSO₄), filtered and concentrated to afford crude. The crude was purified by silica gel chromatography using 30% EtOAc/pet ether as an eluent to afford 1-bromo-2,5-dichloro-3-methoxybenzene (13 g, 81% yield) as off white solid. ¹H NMR (300 MHz, CDCl₃) δ 7.26 (d, J=2.8 Hz, 1H), 6.87 (d, J=2.8 Hz, 1H), 3.93 (s, 3H).

b) (2,5-dichloro-3-methoxyphenyl)(4-methoxybenzyl)sulfane

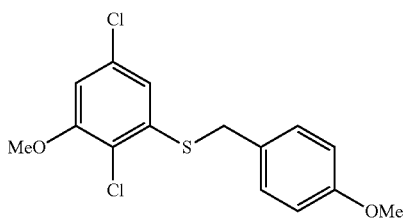 [SMILES: COc1ccc(CSc2cc(Cl)cc(OC)c2Cl)cc1]

To an argon purged solution of 1-bromo-2,5-dichloro-3-methoxybenzene (13 g, 50.8 mmol), (4-methoxyphenyl)methanethiol (9.40 g, 61.0 mmol) and DIPEA (17.74 mL, 102 mmol) in toluene (200 mL), xantphos (2.94 g, 5.08 mmol) and Pd₂(dba)₃ (4.65 g, 5.08 mmol) were added at ambient temperature and heated to 90° C. for 4 h under argon atmosphere. After 4 h the reaction mixture was cooled to RT and passed through a pad of Celite® and the filtrate was diluted with water and extracted with EtOAc. The organic layer was washed with water, brine, dried over Na₂SO₄ and concentrated under reduced pressure to afford crude. The crude was purified by silica gel chromatography using 10% EtOAc/pet ether as an eluent to afford (2,5-dichloro-3-methoxyphenyl)(4-methoxybenzyl)sulfane (13 g, 61% yield) as a yellow solid. ¹H NMR (300 MHz, CDCl₃) δ 7.30-7.25 (m, 2H), 6.87-6.84 (m, 3H), 6.73-6.72 (m, 1H), 4.10 (s, 2H). 3.87 (s, 3H), 3.79 (s, 3H).

c) 2,5-Dichloro-3-methoxybenzenethiol

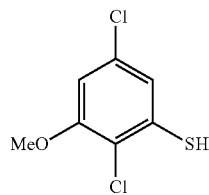 [SMILES: COc1cc(Cl)cc(S)c1Cl]

To a stirred solution of (2,5-dichloro-3-methoxyphenyl)(4-methoxybenzyl)sulfane (13 g, 39.5 mmol) in anisole (70 mL) was added TFA (70 mL, 909 mmol) at ambient temperature and heated to 100° C. for 2 h. After 2 h the reaction mixture was diluted with water and extracted with EtOAc. The organic layer was washed with 2N NaOH solution. The aqueous layer was washed twice with EtOAc, finally acidified with conc. HCl and extracted with EtOAc. The organic layer washed with water and evaporation to afford 2,5-dichloro-3-methoxybenzenethiol (5.5 g, 54.1% yield) as a yellow liquid. ¹H NMR (300 MHz, DMSO-d₆) δ 7.28 (s, 1H), 6.99 (s, 1H), 6.02 (brs, 1H). 3.86 (s, 3H).

d) Ethyl 4-((2,5-dichloro-3-methoxyphenyl)thio)-3-oxobutanoate

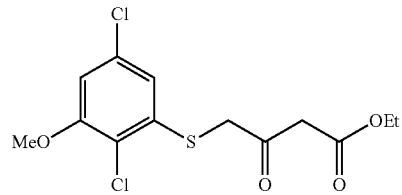 [SMILES: CCOC(=O)CC(=O)CSc1cc(Cl)cc(OC)c1Cl]

To an ice cooled solution of 2,5-dichloro-3-methoxybenzenethiol (5.5 g, 26.3 mmol) and K₂CO₃ (10.91 g, 79 mmol) in DMF (50 mL) was slowly added ethyl 4-chloro-3-oxobutanoate (8.66 g, 52.6 mmol) and the reaction mass was allowed to stir at ambient temperature. After 2 h the reaction mixture was diluted with water and extracted with EtOAc. The organic layer was washed with water, brine, dried over Na₂SO₄ and concentrated under reduced pressure to afford crude which was used as such for next step.

e) Ethyl 2-(4,7-dichloro-6-methoxybenzo[b]thiophen-3-yl)acetate

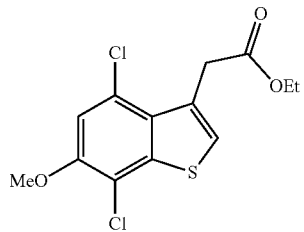 [SMILES: CCOC(=O)Cc1csc2c(Cl)c(OC)cc(Cl)c12]

To the above crude ethyl 4-((2,5-dichloro-3-methoxyphenyl)thio)-3-oxobutanoate (6 g, 17 mmol), methane sulfonic acid (5 mL, 77 mmol) was added and stirred at ambient temperature for 1 h. The reaction mixture was diluted with water and extracted with EtOAc. The organic layer was washed with water, brine, dried over Na₂SO₄ and concentrated under reduced pressure to afford crude. The crude was purified by silica gel chromatography using 30% EtOAc/pet-ether as an eluent to afford ethyl 2-(4,7-dichloro-6-methoxybenzo[b]thiophen-3-yl)acetate (4 g, 47.2% yield) as an off white solid. ¹H NMR (300 MHz, CDCl₃) δ 7.19 (s, 1H), 7.13 (s, 1H), 4.25-4.15 (q, J=4 Hz, 2H), 4.09 (s, 2H), 3.98 (s, 3H), 1.30 (t, J=4.5 Hz, 3H). LCMS (ES) m/z 318.8 (M+H)⁺ f) Ethyl 2-(4,7-dichloro-6-hydroxybenzo[b]thiophen-3-yl)acetate

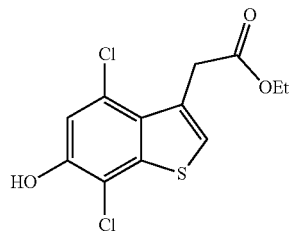 [SMILES: CCOC(=O)Cc1csc2c(Cl)c(O)cc(Cl)c12]

To a stirred solution of ethyl 2-(4,7-dichloro-6-methoxybenzo[b]thiophen-3-yl)acetate (1 g, 3.13 mmol) in DCM (10 mL) was slowly added boron trifluoride methyl sulfide complex (5 mL, 3.13 mmol) at ambient temperature and allowed to stir for 12 h. The reaction mixture was diluted with water and basified with saturated NaHCO₃, extracted with EtOAc. The organic layer was washed with water, brine, dried over Na₂SO₄ and concentrated under reduced pressure to afford crude. The crude was triturated with ethers to afford ethyl 2-(4,7-dichloro-6-hydroxybenzo[b]thiophen-3-yl)acetate (800 mg, 73.6% yield) as off-white solid. ¹H NMR (400 MHz, DMSO-d₆) δ 10.85 (s, 1H), 7.51 (s, 1H), 7.10 (s, 1H), 4.12-4.05 (q, J=4 Hz, 2H), 3.96 (s, 2H), 1.19 (t, J=4.0 Hz, 3H).

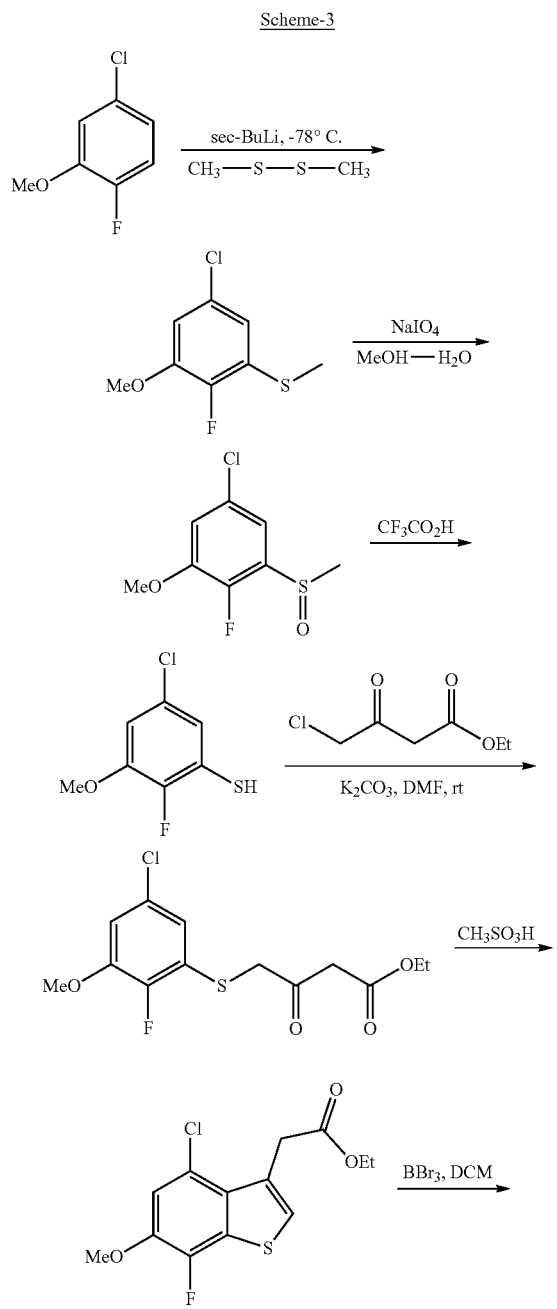

Scheme-3

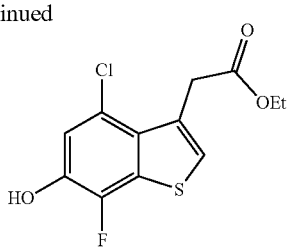

a)
(5-Chloro-2-fluoro-3-methoxyphenyl)(methyl)sulfane

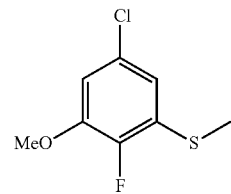

To a stirred solution of 4-chloro-1-fluoro-2-methoxybenzene (8.0 g, 49.8 mmol) in THF (150 mL) was added dropwise (over a period of 20 min) sec-butyllithium (80 mL, 112 mmol) at −78° C. and stirred for 30 min. Dimethyl disulfide (9.74 mL, 110 mmol) was added to the reaction mixture at same temperature. The reaction mixture was stirred at −78° C. under argon atmosphere for 1.5 h. The reaction mixture was quenched with sat NH₄Cl solution and partitioned between water and EtOAc. The EtOAc layer was washed with water and brine, dried over anhydrous Na₂SO₄, filtered and the filtrate was evaporated under reduced pressure to get crude material. The resultant residue was purified by column chromatography (100-200 silica mesh and eluent was 2% EtOAc in pet ether) to afford (5-chloro-2-fluoro-3-methoxyphenyl)(methyl)sulfane (5.0 g, 48.6% yield) as an off-white solid. ¹H NMR (500 MHz, CDCl₃): δ 6.79-6.76 (m, 2H), 3.86 (s, 3H), 2.36 (s, 3H).

b) 5-Chloro-2-fluoro-1-methoxy-3-(methylsulfinyl)benzene

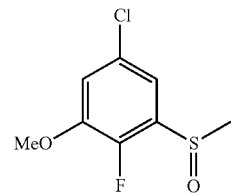

To a stirred solution of (5-chloro-2-fluoro-3-methoxyphenyl)(methyl)sulfane (5.0 g, 24.19 mmol) in methanol (200 mL) and water (40 mL) was added sodium periodate (7.76 g, 36.3 mmol) at 0° C. The reaction mixture was stirred at 26° C. for 16 h. The reaction mixture was evaporated under reduced pressure the residue was partitioned between water and EtOAc. The organic layer was washed with water and brine, dried over anhydrous Na₂SO₄, filtered and the filtrate was evaporated under reduced pressure to get crude material.

The resultant residue was purified by column chromatography (100-200 silica mesh and eluent was 15% EtOAc in pet ether) to afford 5-chloro-2-fluoro-1-methoxy-3-(methylsulfinyl)benzene (4.0 g, 74.3% yield) as an off-white solid. $^1$H NMR (300 MHz, DMSO-d$_6$): δ 7.39-7.36 (m, 1H), 7.06 (dd, J=2.5, 7.5 Hz, 1H), 3.93 (s, 3H), 2.83 (s, 3H). LCMS (ES) m/z 223.16 (M+H)$^+$ c) 5-Chloro-2-fluoro-3-methoxybenzenethiol

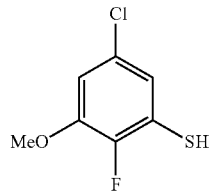 [SMILES: COc1cc(Cl)cc(S)c1F]

To a stirred solution of 5-chloro-2-fluoro-1-methoxy-3-(methylsulfinyl)benzene (1.50 g, 6.74 mmol) in acetonitrile (60 mL) was added trifluoroacetic anhydride (1.9 mL, 13.47 mmol) at 0° C. and stirred at same temperature for 1 h. Then the reaction mixture was stirred at RT for 1 h. The reaction mixture was concentrated. The residue was dissolved in a mixture of methanol (10 mL) and TEA (10.0 mL) at 0° C. and stirred for 10 min and concentrated in vacuum. The mixture was diluted with sat NH$_4$Cl and extracted with EtOAc. The organic layer was washed with 1N NaOH. The aqueous layer was acidified with 1N HCl and extracted with EtOAc. The organic layer washed with brine dried over anhydrous Na$_2$SO$_4$, filtered and the filtrate was evaporated under reduced pressure to get crude material. The resulted residue was purified by column chromatography (100-200 silica mesh, eluent was 10% EtOAc in pet ether) to obtain 5-chloro-2-fluoro-3-methoxybenzenethiol (0.75 g, 57.8% yield) as an off-white solid. $^1$H NMR (400 MHz, DMSO-d$_6$): δ 6.84 (m, 1H), 6.74 (dd, J=2.4, 6.8 Hz, 1H), 3.88 (s, 3H), 3.81 (s, H)

d) Ethyl 4-((5-chloro-2-fluoro-3-methoxyphenyl)thio)-3-oxobutanoate

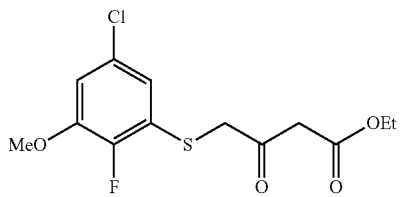 [SMILES: CCOC(=O)CC(=O)CSc1cc(Cl)cc(OC)c1F]

To the stirred suspension of 5-chloro-2-fluoro-3-methoxybenzenethiol (750 mg, 3.89 mmol) and potassium carbonate (538 mg, 3.89 mmol) in DMF (10 mL) was added ethyl 4-chloro-3-oxobutanoate (705 mg, 4.28 mmol) at 0° C. The reaction mixture was stirred at RT for 2 h. The reaction mixture was diluted with water and extracted with EtOAc. The organic layer was separated and dried over anhydrous Na$_2$SO$_4$, filtered and the filtrate was evaporated under reduced pressure to get crude product ethyl 4-((5-chloro-2-fluoro-3-methoxyphenyl)thio)-3-oxobutanoate (750 mg, 60.1% yield) as a brown liquid. $^1$H NMR 400 MHz, CDCl$_3$): δ 6.94-6.92 (m, 1H) 6.86 (dd, J=2.4, 7.2 Hz, 1H), 4.23 (q, 2H), 3.87 (s, 3H), 3.82 (s, 2H), 3.64 (s, 2H), 1.27 (t, J=2.4 Hz, 3H).

e) Ethyl 2-(4-chloro-7-fluoro-6-methoxybenzo[b]thiophen-3-yl)acetate

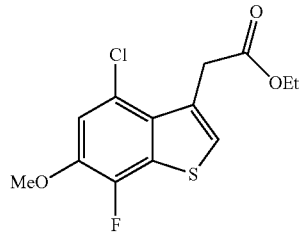 [SMILES: CCOC(=O)Cc1csc2c(F)c(OC)cc(Cl)c12]

To a stirred solution of ethyl 4-((5-chloro-2-fluoro-3-methoxyphenyl)thio)-3-oxobutanoate (750 mg, 2.338 mmol) was added methanesulfonic acid (3.0 ml, 46.2 mmol) at 0° C. and mixture was stirred at RT for 1 h. The reaction mixture was partitioned between EtOAc and water, the separated organic layer was washed with brine solution, dried over anhydrous Na$_2$SO$_4$, filtered and filtrate was evaporated under reduced pressure to get crude material. The resultant residue was purified by column chromatography (100-200 silica mesh and eluent was 15% EtOAc in pet ether) to afford ethyl 2-(4-chloro-7-fluoro-6-methoxybenzo[b]thiophen-3-yl)acetate (450 mg, 58.5% yield) as a pale yellow liquid. $^1$H NMR 500 MHz, CDCl$_3$): δ 7.16 (s, 1H) 7.07 (d, J=7.0 Hz, 1H), 4.17 (q, 2H), 4.07 (s, 2H), 3.95 (s, 3H), 1.26 (t, J=5.6 Hz, 3H). LCMS (ES) m/z 303.25 (M+H)$^+$.

f) Ethyl 2-(4-chloro-7-fluoro-6-hydroxybenzo[b]thiophen-3-yl)acetate

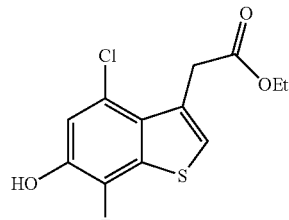

To a solution of ethyl 2-(4-chloro-7-fluoro-6-methoxybenzo[b]thiophen-3-yl)acetate (350 mg, 1.156 mmol) in DCM (10 mL) was added BBr$_3$ (0.164 mL, 1.734 mmol) at −50° C. The reaction mixture was cool to room temperature for 1 h under nitrogen atmosphere. The Reaction mixture was quenched with saturated NaHCO$_3$ solution and partitioned between water and DCM. The DCM layer was washed with water and brine, dried over anhydrous Na$_2$SO$_4$, filtered and the filtrate was evaporated under reduced pressure to get crude material. The resulted residue was purified by column chromatography (100-200 silica mesh, eluent was 10% EtOAc in pet ether) to obtain ethyl 2-(4-chloro-7-fluoro-6-hydroxybenzo[b]thiophen-3-yl)acetate (300 mg, 80% yield) as an off-white solid. $^1$H NMR 500 MHz, CDCl$_3$): δ 7.15 (s, 1H) 7.05 (d, J=7.0 Hz, 1H), 4.2 (q, J=5.6 Hz, 2H), 4.08 (s, 2H), 1.26 (t, J=5.6 Hz, 3H). LCMS (ES) m/z 289.19 (M+H)$^+$.

Scheme-4

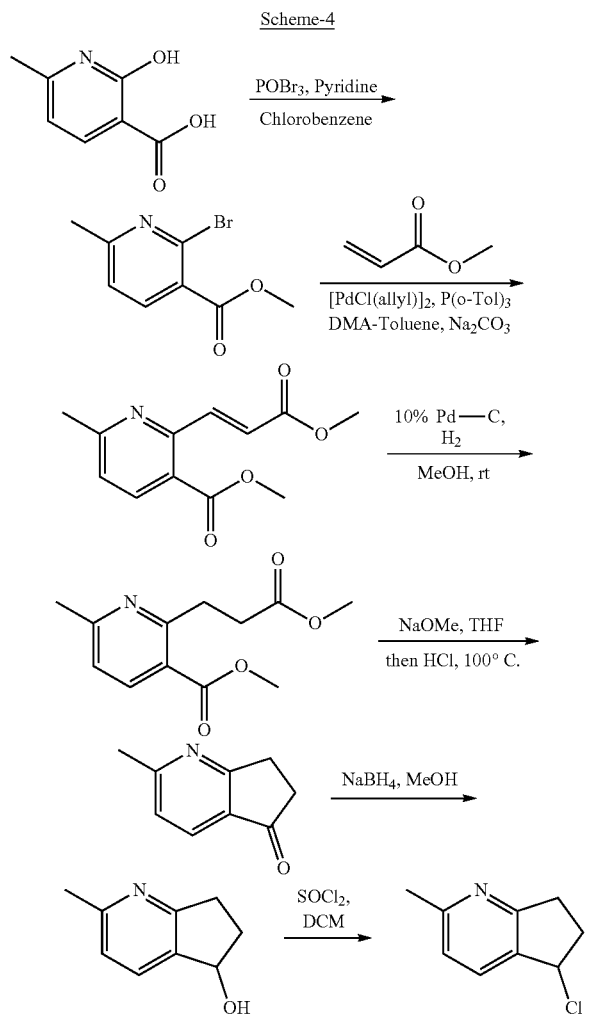

a) Methyl 2-bromo-6-methylnicotinate

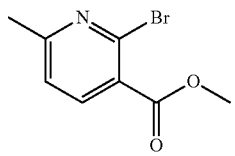

Phosphorus oxybromide (21.53 g, 75 mmol) was added to the stirred solution of 2-hydroxy-6-methylnicotinic acid (5 g, 32.7 mmol), pyridine (0.475 mL, 5.88 mmol) in chlorobenzene (100 mL) at room temperature under nitrogen. The reaction mixture was refluxed for 1 h and concentrated under vacuum before treating with an excess of cold methanol. The solution was stirred for an additional 1 h and again concentrated under vacuum. The residue was dissolved in water and pH was adjusted to ~8.0 by adding K$_2$CO$_3$ before extraction of the product with CH$_2$C$_{12}$. The organic layer was washed with water and brine solution, dried over anhydrous Na$_2$SO$_4$. Filtrate was evaporated completely under reduced pressure to give crude residue. The resulted crude compound was purified by flash column chromatography (100-200 silica mesh, eluent was 30% EtOAc in pet ether) to obtained methyl 2-bromo-6-methylnicotinate (6.1 g, 79% yield) as colorless oil. $^1$H NMR (400 MHz, CDCl$_3$): δ 8.00 (d, J=7.6 Hz, 1H), 7.18 (d, J=8.0 Hz, 1H), 3.94 (s, 3H), 2.59 (s, 3H); LCMS (ES) m/z 230.0 (M+H)$^+$ b) Methyl (E)-2-(3-methoxy-3-oxoprop-1-en-1-yl)-6-methylnicotinate

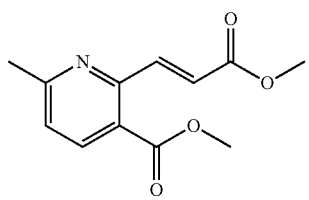

Na$_2$CO$_3$ (8.43 g, 80 mmol) was added to a solution of methyl 2-bromo-6-methylnicotinate (6.1 g, 26.5 mmol) and methyl acrylate (6.08 mL, 67.1 mmol) in mixture of DMA (16.99 mL, 181 mmol) and toluene (55 mL) at room temperature. Then the reaction mixture was degassed for 15 min. Tri-o-tolylphosphine (0.807 g, 2.65 mmol) and allylpalladium chloride dimer (0.4850 g, 1.326 mmol) were added and the reaction mixture was stirred at 115° C. in sealed tube for 5 h. Filtered through pad of Celite®, and the filtrate was concentrated under reduced pressure. The resultant crude compound was purified by flash column chromatography on 100-200 mesh silica gel using 20% EtOAc/pet-ether as an eluent to obtained (E)-methyl 2-(3-methoxy-3-oxoprop-1-en-1-yl)-6-methylnicotinate (3.30 g, 43.0% yield) as a colorless oil. $^1$H NMR (400 MHz, CDCl$_3$): δ 8.53 (dd, J=1.2, 15.2 Hz, 1H), 8.22 (d, J=6.8 Hz, 1H), 7.20-7.11 (m, 2H), 3.94 (s, 3H), 3.82 (s, 3H), 2.60 (s, 3H). LCMS (ES) m/z 236.09 (M+H)$^+$ c) Methyl 2-(3-methoxy-3-oxopropyl)-6-methylnicotinate

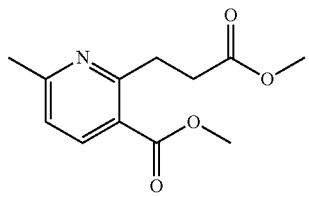

10% Pd—C (300 mg, 2.82 mmol) was added to a solution of (E)-methyl 2-(3-methoxy-3-oxoprop-1-en-1-yl)-6-methylnicotinate (3.30 g, 14.03 mmol) in methanol (120 mL) at 25° C. The reaction mixture was stirred for 3 h at 25° C. under hydrogen atmospheric pressure of 50 psi. The reaction mixture was filtered and filtrate was evaporated under pressure to get methyl 2-(3-methoxy-3-oxopropyl)-6-methylnicotinate (2.8 g, 74.3% yield) as a yellow oil. $^1$H NMR (400 MHz, CDCl$_3$): δ 8.08 (d, J=8.0 Hz, 1H), 7.06 (d, J=7.6 Hz, 1H), 3.90 (s, 3H), 3.67 (s, 3H), 3.50 (t, J=7.6 Hz, 2H), 2.81 (t, J=8.0 Hz, 2H), 2.55 (s, 3H). LCMS (ES) m/z 238.10 (M+H)$^+$ d) 2-Methyl-6,7-dihydro-5H-cyclopenta[b]pyridin-5-one

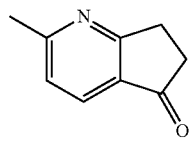

Sodium methoxide (0.956 g, 17.70 mmol) was added to a solution of methyl 2-(3-methoxy-3-oxopropyl)-6-methylnicotinate (2.8 g, 11.80 mmol) in THF (30 mL) under nitrogen atmosphere. The reaction mixture was warmed to reflux during 2 h. The solvent was removed under vacuo and HCl (20 ml, 90 mmol) 4.5 M was added, the mixture was stirred 2 h at reflux. The reaction mixture was dissolved in water and pH was adjusted to ~8.0 by adding $K_2CO_3$ before extraction of the product with $CH_2Cl_2$. The organic layer was washed with water and brine solution, dried over anhydrous $Na_2SO_4$. Filtrate was evaporated completely under reduced pressure to give crude residue. The crude residue was purified by silica gel column chromatography by using EtOAc in hexane as eluent, the product was eluted at 40% EtOAc/Pet-ether to get 2-methyl-6,7-dihydro-5H-cyclopenta[b]pyridin-5-one (1.3 g, 66.1% yield) as a colorless oil. $^1$H NMR (400 MHz, $CDCl_3$): δ 7.91 (d, J=8.4 Hz, 1H), 7.19 (d, J=7.6 Hz, 1H), 3.24 (t, J=6.0 Hz, 2H), 2.78 (t, J=8.0 Hz, 2H), 2.67 (s, 3H). LCMS (ES) m/z 147.98 (M+H)$^+$ e) 2-Methyl-6,7-dihydro-5H-cyclopenta[b]pyridin-5-ol

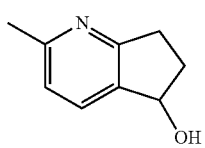

$NaBH_4$ (0.334 g, 8.83 mmol) was added lot wise to the stirred solution of 2-methyl-6,7-dihydro-5H-cyclopenta[b]pyridin-5-one (1.3 g, 8.83 mmol) in methanol (30 ml) at 0° C. and the mixture was stirred at 0° C. for 2 h. The reaction mixture was diluted with water and mixture was concentrated under reduced pressure. The resulted residue was partitioned between EtOAc and water, the separated organic layer was washed with brine solution, dried over anhydrous $Na_2SO_4$, filtered and filtrate was evaporated under reduced pressure. The resulted crude compound was purified by flash column chromatography (100-200 silica mesh, eluent was 70% EtOAc in pet ether) to obtained 2-methyl-6,7-dihydro-5H-cyclopenta[b]pyridin-5-ol (0.900 g, 67.6% yield) as a colorless oil. $^1$H NMR (300 MHz, $CDCl_3$): δ 7.59 (d, J=7.5 Hz, 1H), 7.01 (d, J=7.5 Hz, 1H), 5.25 (s, 1H), 3.18-3.08 (m, 1H), 2.95-2.84 (m, 1H), 2.59 (s, 4H), 2.04-1.94 (m, 2H). LCMS (ES) m/z 150.3 [M+H]$^+$ f) 5-Chloro-2-methyl-6,7-dihydro-5H-cyclopenta[b]pyridine

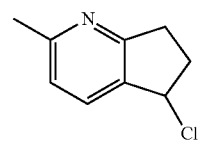

To solution of 2-methyl-6,7-dihydro-5H-cyclopenta[b]pyridin-5-ol (20.66 g, 139 mmol) in DCM (200 mL) was added thionyl chloride (6.74 mL, 92 mmol) at RT and stirred for 20 min, solvents were evaporated under reduced pressure to afford crude product. The crude product was used for the next step without further purification.

Scheme-5

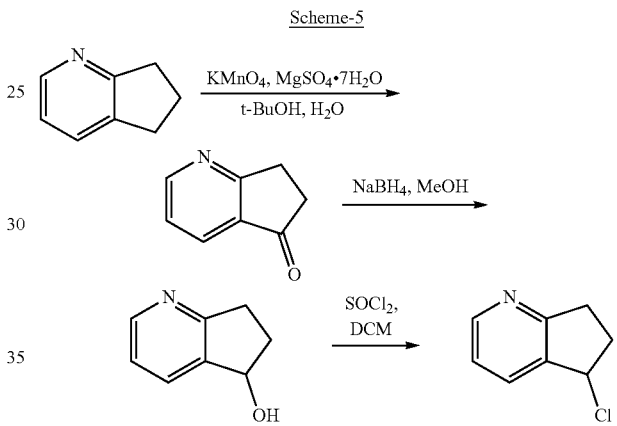

a) 6,7-Dihydro-5H-cyclopenta[b]pyridin-5-one

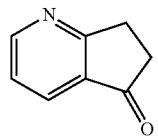

$KMnO_4$ (53.0 g, 336 mmol) dissolved in water (2000 mL) was added to the stirred solution of 6,7-dihydro-5H-cyclopenta[b]pyridine (20 g, 168 mmol) and $MgSO_4 \cdot 7H_2O$ (40.4 g, 336 mmol) in tert-butanol (500 mL) at 25° C. and the reaction mixture was stirred at 30° C. for 3 h. The reaction mixture was filtered through a Celite® bed, partitioned between EtOAc and water, the separated organic layer was washed with brine solution, dried over anhydrous $Na_2SO_4$, filtered and filtrate was concentrated under reduced pressure. The resulted crude compound was purified by flash column chromatography on 100-200 silica gel, using 20-30% EtOAc-Pet ether as an eluent to obtained 6,7-dihydro-5H-cyclopenta[b]pyridin-5-one (10 g, 44.7% yield) as an off white solid. LCMS (ES) m/z 134.01 [M+H]$^+$.

b) 6,7-Dihydro-5H-cyclopenta[b]pyridin-5-ol

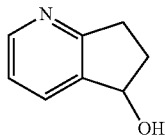

NaBH₄ (25.6 g, 676 mmol) was added portion wise to the stirred solution of 6,7-dihydro-5H-cyclopenta[b]pyridin-5-one (60 g, 451 mmol) in methanol (600 mL) at 0° C. and the reaction mixture was stirred at 25° C. for 1 h under nitrogen atmosphere. The reaction mixture was quenched with water and then solvent was distilled off. The residue was partitioned between EtOAc and water, the separated organic layer was washed with brine solution, dried over anhydrous Na₂SO₄, filtered and filtrate was concentrated under reduced pressure. The resulted crude compound was purified by flash column chromatography on 100-200 silica gel, using EtOAc-Pet ether as an eluent to obtained 6,7-dihydro-5H-cyclopenta[b]pyridin-5-ol (40 g, 62.5% yield) as an off white solid. LCMS (ES) m/z 136.11 [M+H]⁺.

c) 5-Chloro-6,7-dihydro-5H-cyclopenta[b]pyridine

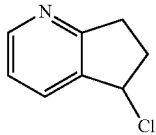

To a solution of 6,7-dihydro-5H-cyclopenta[b]pyridin-5-ol (5 g, 37.0 mmol) in DCM (50 mL) was added thionyl chloride (4.05 mL, 55.5 mmol) at 0° C. and the reaction mixture was stirred at 25° C. for 1 h under nitrogen atmosphere. Reaction mixture was concentrated under reduced pressure to get crude product 5-chloro-6,7-dihydro-5H-cyclopenta[b]pyridine (5.5 g) as a brown gummy liquid. Crude was used for the next step without further purification. LCMS (ES) m/z 154.19 [M+H]⁺.

Scheme-6

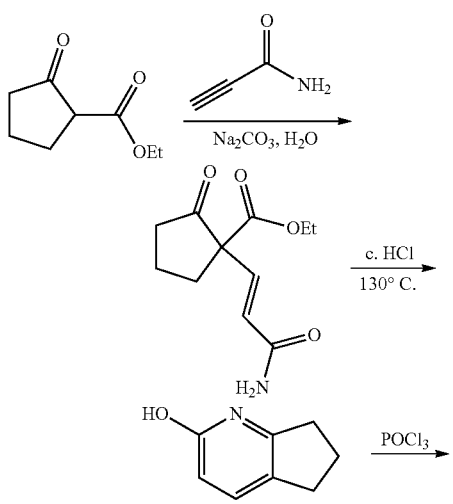

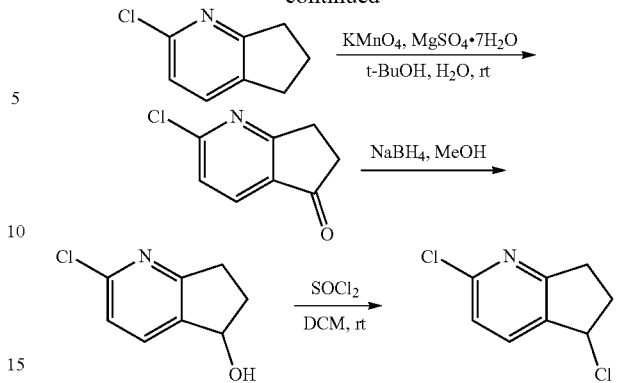

a) Ethyl (E)-1-(3-amino-3-oxoprop-1-en-1-yl)-2-oxocyclopentane-1-carboxylate

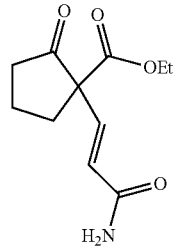 [SMILES: CCOC(=O)C1(/C=C/C(N)=O)CCCC1=O]

Ethyl 2-oxocyclopentanecarboxylate (150 g, 960 mmol) was added to the stirred solution of propiolamide (113 g, 1633 mmol) and Na₂CO₃ (112 g, 1056 mmol) in water (1500 mL) at 0° C. and the mixture was stirred at RT for 6 h. The reaction mixture was diluted with water and extracted with DCM, the organic layer was washed with brine solution, dried over anhydrous Na₂SO₄, filtered and filtrate was evaporated under reduced pressure to get crude product. The resulted crude compound was purified by flash column chromatography (100-200 silica mesh, eluent was 80% EtOAc in pet ether) to obtained (E)-ethyl 1-(3-amino-3-oxoprop-1-en-1-yl)-2-oxocyclopentanecarboxylate (150 g, 68.8% yield) as an off-white solid. ¹H NMR (400 MHz, CDCl₃): δ 6.58 (d, J=10.4 Hz, 1H), 5.97 (dd, J=2.0, 10.0 Hz, 1H), 5.89 (brs, 2H), 4.26 (q, J=4.8 Hz, 2H), 2.50-2.42 (m, 1H), 2.26-2.19 (m, 1H), 2.08-1.88 (m, 3H), 1.76-1.72 (m, 1H), 1.31 (t, J=7.2 Hz, 3H). LCMS (ES) m/z 226.23 [M+H]⁺ b) 6,7-Dihydro-5H-cyclopenta[b]pyridin-2-ol

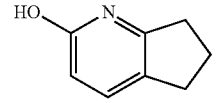

Conc. HCl (209 ml, 6882 mmol) was added to the (E)-ethyl 1-(3-amino-3-oxoprop-1-en-1-yl)-2-oxocyclopentanecarboxylate (155 g, 688 mmol) at room temperature and the mixture was stirred at 130° C. for 5 h. The reaction mixture was concentrated and poured into ice. The pH was adjusted to ~7.0 by dropwise addition of saturated aqueous NaHCO₃ solution, and filtered the precipitated solid. The solid was washed with water to get 6,7-dihydro-5H-cyclopenta[b]pyridin-2-ol (80 g, 86% yield) as an off-white solid. ¹H NMR (400 MHz, DMSO-d₆): δ 7.71 (s, 1H), 6.62 (s, 1H), 2.89-2.85 (m, 2H), 2.75-2.72 (m, 2H), 2.11-2.04 (m, 2H). LCMS (ES) m/z 136.07 [M+H]⁺ c) 2-Chloro-6,7-dihydro-5H-cyclopenta[b]pyridine

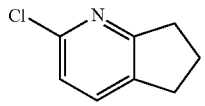

A mixture of 6,7-dihydro-5H-cyclopenta[b]pyridin-2-ol (70 g, 518 mmol), POCl₃ (200.0 ml, 2146 mmol) and DMF (10 mL) was stirred under nitrogen atmosphere at 120° C. for 3 h. After cooling, the mixture was poured into ice water, basified with 8 M NaOH aqueous solution and extracted with AcOEt. The extract was washed with brine, dried over anhydrous Na₂SO₄, and concentrated. The resulted crude compound was purified by flash column chromatography (100-200 silica mesh, eluent was 10% EtOAc in pet ether) to obtained 2-chloro-6,7-dihydro-5H-cyclopenta[b]pyridine (35 g, 43.7% yield) as an off white solid. ¹H NMR (400 MHz, CDCl₃): δ 7.44 (d, J=7.6 Hz, 1H), 7.06 (d, J=8.0 Hz, 1H), 3.01 (t, J=7.2 Hz, 2H), 2.92 (t, J=7.2 Hz, 2H), 2.18-2.10 (m, 2H). LCMS (ES) m/z 154.09 [M+H]⁺ d) 2-Chloro-6,7-dihydro-5H-cyclopenta[b]pyridin-5-one

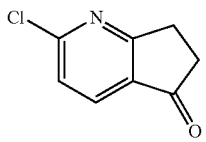 [SMILES: O=C1CCc2nc(Cl)ccc21]

KMnO₄ (72.0 g, 456 mmol) dissolved in water (3.5 L) was added to the stirred solution of 2-chloro-6,7-dihydro-5H-cyclopenta[b]pyridine (35.00 g, 228 mmol) and magnesium sulfate heptahydrate (68.2 g, 456 mmol) in tert-butanol (875 mL) and the reaction mixture was stirred at RT for 2 h under nitrogen atmosphere. The reaction mixture was filtered through a Celite® pad, partitioned between EtOAc and water. The separated organic layer was washed with brine solution, dried over anhydrous Na₂SO₄, filtered and filtrate was concentrated under reduced pressure. The resulted crude compound was purified by flash column chromatography on 100-200 silica gel, using 20-30% EtOAc-Pet ether as an eluent to obtained 2-chloro-6,7-dihydro-5H-cyclopenta[b]pyridin-5-one (25 g, 65.4% yield) as an off white solid. ¹H NMR (400 MHz, CDCl₃): δ 7.97 (d, J=8.4 Hz, 1H), 7.37 (d, J=8.0 Hz, 1H), 3.28-3.25 (m, 2H), 2.82-2.79 (m, 2H); LCMS (ES) m/z 168.08 [M+H]⁺ e) 2-Chloro-6,7-dihydro-5H-cyclopenta[b]pyridin-5-ol

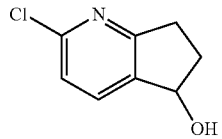 [SMILES: OC1CCc2nc(Cl)ccc21]

Sodium borohydride (108 mg, 2.86 mmol) was added lot wise to the stirred solution of 2-chloro-6,7-dihydro-5H-cyclopenta[b]pyridin-5-one (480 mg, 2.86 mmol) in methanol (100 mL) at 0° C. and the mixture was stirred at 0° C. for 1 h. The reaction mixture was diluted with water and mixture was concentrated under reduced pressure. The resulted residue was partitioned between EtOAc and water, the separated organic layer was washed with brine solution, dried over anhydrous Na₂SO₄, filtered and filtrate was evaporated under reduced pressure. The resulted crude compound was purified by flash column chromatography (100-200 silica mesh, eluent was 30% EtOAc in pet ether) to obtained 2-chloro-6,7-dihydro-5H-cyclopenta[b]pyridin-5-ol (450 mg, 91% yield) as an off-white solid. ¹H NMR (400 MHz, CDCl₃): δ 7.67 (d, J=8.0 Hz, 1H), 7.19 (d, J=8.0 Hz, 1H), 5.28-5.26 (m, 1H), 3.13-3.10 (m, 1H), 2.95-2.92 (m, 1H), 2.05-2.02 (m, 1H) 1.89 (m, 1H). LCMS (ES) m/z 170.16 [M+H]⁺ f) 2,5-Dichloro-6,7-dihydro-5H-cyclopenta[b]pyridine

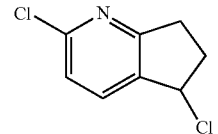 [SMILES: Clc1ccc2c(n1)CCC2Cl]

SOCl₂ (0.232 ml, 3.18 mmol) was added to the stirred solution of 2-chloro-6,7-dihydro-5H-cyclopenta[b]pyridin-5-ol (450.00 mg, 2.65 mmol) in DCM (50 ml) and the mixture was stirred at room temperature for 3 h. The reaction mixture was concentrated under reduced pressure and crude used for the next step. LCMS (ES) m/z 188.15 [M+H]⁺.

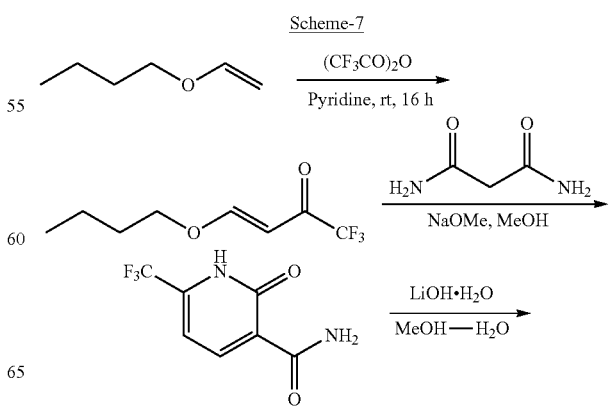

Scheme-7

-continued

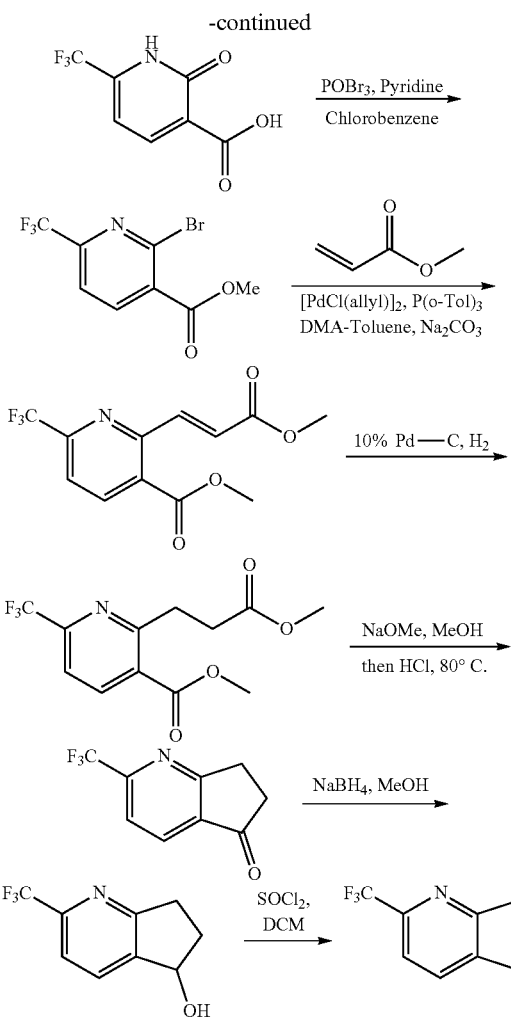

a) Butoxy-1,1,1-trifluorobut-3-en-2-one

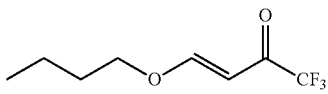

To a stirred solution of t-(vinyloxy)butane (50 g, 499 mmol), pyridine (40.4 mL, 499 mmol) in Chloroform (500 mL) at 0° C. 1,1,1,5,5,5-hexafluoropentane-2,4-dione (104 g, 499 mmol) in chloroform (200 ml) was added and stirred for 16 h After completion of reaction, mixture was poured into cool water. The solution was extracted by DCM and washed with water followed by brine. The organic layer was dried over anhydrous sodium sulphate and solvent was removed under reduced pressure. The crude was purified by flash column chromatography on silica gel (100-200 mesh), eluting with 0-30% gradient of EtOAc in hexane to afford (E)-1-ethoxy-5,5,5-trifluoropent-1-en-3-one (70 g, 73% yield) as a liquid. $^1$H NMR (400 MHz, CDCl$_3$) δ 7.90 (d, J=12 Hz, 1H), 5.86 (d, J=2.4 Hz, 1H), 4.03 (t, J=6.4, 2H), 1.77-1.70 (m, 2H), 1.48-1.39 (m, 2H), 0.95 (t, J=7.6 Hz, 3H).

b) 2-Oxo-6-(trifluoromethyl)-1,2-dihydropyridine-3-carboxamide

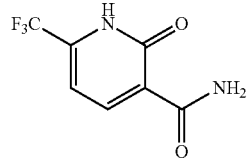

To a stirred solution of malonamide (39.2 g, 384 mmol) in methanol (300 mL) at 0° C. (E)-1-ethoxy-5,5,5-trifluoropent-1-en-3-one (70 g, 384 mmol) in methanol (300 mL) was added and reaction mixture was stirred at reflux temperature for 6 h, After completion of reaction mixture was concentrated, poured into cool water and acidified with dil.HCl (pH 2) to get solid. Solid was filtered and dried to get pure compound 2-oxo-6-(trifluoromethyl)-1,2-dihydropyridine-3-carboxamide (60 g, 73.1% yield) as off white solid. $^1$H NMR (400 MHz, DMSO-d$_6$) δ ppm 13.66 (brs, 1H), 8.46 (brs, 2H), 8.07 (brs, 1H), 7.38 (brs, 1H). LCMS (ES$^+$) m/z 207.11 [M+H]$^+$.

c) 2-Oxo-6-(trifluoromethyl)-1,2-dihydropyridine-3-carboxylic acid

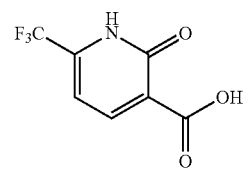

To a stirred solution of 2-oxo-6-(trifluoromethyl)-1,2-dihydropyridine-3-carboxamide (60 g, 291 mmol) in methanol (300 mL), water (100 mL) LiOH (20.91 g, 873 mmol) was added at room temperature and reaction mixture was stirred at reflux temperature for 24 h. After completion of the reaction, mixture was poured into cool water and acidified with 1N HCl. to get solid. Solid was filtered and dried to get pure compound 2-oxo-6-(trifluoromethyl)-1,2-dihydropyridine-3-carboxylic acid (52 g, 86% yield) as off white solid. $^1$H NMR (400 MHz, CDCl$_3$) δ ppm 12.74 (brs, 1H), 8.72 (d, J=6.5 Hz, 1H), 7.10 (d, J=5.5 Hz, 1H). LCMS (ES) m/z 208.08 (M+H)$^+$.

d) Methyl 2-bromo-6-(trifluoromethyl)nicotinate

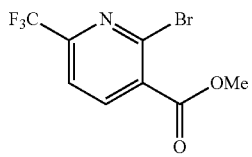 [SMILES: COC(=O)c1ccc(C(F)(F)F)nc1Br]

To the stirred solution of 2-hydroxy-6-(trifluoromethyl) nicotinic acid (23 g, 111 mmol) and pyridine (8.98 mL, 111 mmol) in chlorobenzene (250 mL) phosphorus oxybromide (63.7 g, 222 mmol) was added small portions wise at room temperature and the mixture was stirred at 120° C. for 16 h.

After completion, the reaction mixture was concentrated under vacuum. The residue was cooled 0° C. and added excess cold methanol slowly. The solution stirred additional 1 h and again concentrated under vacuum. The residue dissolved in water and pH adjusted to ~8 using K$_2$CO$_3$ before extraction with EtOAc. The organic layer was separated and dried over anhydrous Na$_2$SO$_4$, filtered and the filtrate was concentrated under reduced pressure to obtain as a brown liquid. The crude was purified by flash column chromatography on silica gel (100-200 mesh), eluting with 0-10% gradient of EtOAc in hexane to afford 4-bromo-1-(tetrahydro-2H-pyran-2-yl)-1H-pyrazole in (400 g, 42.1%) yields. $^1$H NMR (500 MHz, CDCl$_3$) δ 8.20 (d, J=8 Hz, 1H), 7.71 (d, J=8.0 Hz, 1H), 4.01 (s, 3H).

e) Methyl (E)-2-(3-methoxy-3-oxoprop-1-en-1-yl)-6-(trifluoromethyl)nicotinate

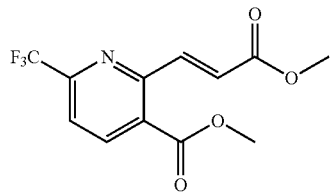 [SMILES: COC(=O)/C=C/c1nc(C(F)(F)F)ccc1C(=O)OC]

To a stirred solution of methyl 2-bromo-6-(trifluoromethyl)nicotinate (21 g, 73.9 mmol), methyl acrylate (16.75 mL, 185 mmol) and sodium carbonate (23.51 g, 222 mmol) in N,N-dimethylacetamide (DMA) (100 mL), toluene (400 mL), allylpalladium chloride dimer (1.353 g, 3.70 mmol), tri-o-tolylphosphine (2.250 g, 7.39 mmol) was added at room temperature in a sealed tube. The resulting reaction mixture was stirred for 16 h at 120° C. After completion, the reaction mixture was filtered through a Celite® bed and was washed with EtOAc thoroughly. The filtrate was concentrated to get crude residue The crude compound was purified by column chromatography (100-200 mesh silica gel) using 10% EtOAc in pet-ether as an eluent to get (E)-methyl 2-(3-methoxy-3-oxoprop-1-en-1-yl)-6-(trifluoromethyl)nicotinate (13 g, 60.8% yield) as yellow solid. $^1$H NMR (400 MHz, DMSO-d$_6$) δ 8.45 (d, J=15.6 Hz, 1H), 8.39 (dd, J=0.4, 8.0 Hz, 1H), 7.71 (d, J=8.4 Hz, 1H), 7.26 (d, J=2.8 Hz, 1H), 4.01 (s, 3H), 3.84 (s, 3H). LCMS (ES) m/z 290.22 [M+H]$^+$.

f) Methyl 2-(3-methoxy-3-oxopropyl)-6-(trifluoromethyl)nicotinate

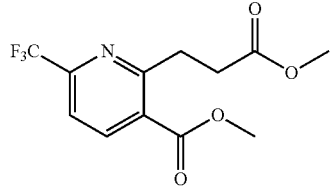 [SMILES: COC(=O)CCc1nc(C(F)(F)F)ccc1C(=O)OC]

To a stirred solution of (E)-methyl 2-(3-methoxy-3-oxoprop-1-en-1-yl)-6-(trifluoromethyl)nicotinate (6.0 g, 20.75 mmol) in ethanol (180 mL), Pd/C (2.65 g) was added at room temperature. The mixture was stirred at room temperature for 1 h under hydrogen balloon pressure, filtered through pad of Celite®, and filtrate was concentrated under vacuo to afford methyl 2-(3-methoxy-3-oxopropyl)-6-(trifluoromethyl)nicotinate (4.5 g, 14.88 mmol, 71.7% yield) as a colorless liquid. $^1$H NMR (400 MHz, CDCl$_3$) δ 8.36 (d, J=8.0 Hz, 1H), 7.60 (d, J=8.0 Hz, 1H), 3.99 (s, 3H), 3.70 (s, 3H), 3.60 (t, J=6.5 Hz, 2H), 2.88 (t, J=7.0 Hz, 2H). LCMS (ES) m/z 292.08 [M+H]$^+$.

g) 2-(Trifluoromethyl)-6,7-dihydro-5H-cyclopenta[b]pyridin-5-one

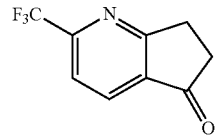 [SMILES: O=C1CCc2nc(C(F)(F)F)ccc21]

To a stirred solution of methyl 2-(3-methoxy-3-oxopropyl)-6-(trifluoromethyl)nicotinate (8 g, 27.5 mmol) in dry methanol (100 mL), sodium methoxide (2.226 g, 41.2 mmol) was added at room temperature and the mixture was stirred for 8 h at 80° C. under argon. The solvent was removed under reduced pressure and the resultant residue was dissolved in HCl (12.50 mL, 411 mmol) and stirred at 80° C. for 8 h. After completion, the reaction mixture was cooled to 0° C. and basified with 3N NaOH solution and partitioned between EtOAc and water. The separated organic layer was washed with brine solution, dried over anhydrous Na$_2$SO$_4$, filtered and filtrate was evaporated under reduced pressure to get the crude residue 2-(trifluoromethyl)-6,7-dihydro-5H-cyclopenta[b]pyridin-5-one (4.0 g, 45.9% yield) as brown colored gum. $^1$H NMR (400 MHz, CDCl$_3$) δ 8.20 (d, J=8.0 Hz, 1H), 7.72 (d, J=8.0 Hz, 1H), 3.39 (t, J=5.0 Hz 2H), 2.88 (t, J=6.0 Hz, 2H); LCMS (ES) m/z 202.27 [M+H]$^+$.

h) 2-(Trifluoromethyl)-6,7-dihydro-5H-cyclopenta[b]pyridin-5-ol

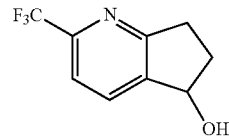

To a stirred solution of 2-(trifluoromethyl)-6,7-dihydro-5H-cyclopenta[b]pyridin-5-one (4.0 g, 19.89 mmol) in methanol (50 mL), sodium borohydride (0.752 g, 19.89 mmol) was added lot wise at 0° C. and the mixture was stirred at room temperature for 2 h. After completion, the reaction mixture was diluted with water and was concentrated under reduced pressure. The resulted residue was partitioned between EtOAc and water. The separated organic layer was washed with brine solution, dried over anhydrous Na$_2$SO$_4$, filtered and filtrate was evaporated under reduced pressure. The crude obtained was purified by column chromatography on silica gel (100-200 mesh) eluted with 20-50% gradient of EtOAc in hexanes to afford 2-(trifluoromethyl)-6,7-dihydro-5H-cyclopenta[b]pyridin-5-ol (3.1 g, 13.84 mmol, 69.6% yield) as an off-white solid. $^1$H NMR (400 MHz, CDCl$_3$) δ 7.86 (d, J=8 Hz, 1H), 7.56 (d, J=7.6

Hz, 1H), 5.36-5.31 (m, 1H), 3.29-3.25 (m, 1H), 3.10-2.90 (m, 1H), 2.7-2.6 (m, 1H), 2.05-1.90 (m, 1H); LCMS (ES) m/z 204.22 [M+H]⁺.

i) 5-Chloro-2-(trifluoromethyl)-6,7-dihydro-5H-cyclopenta[b]pyridine

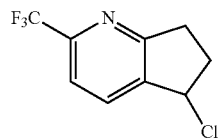 [SMILES: FC(F)(F)c1ccc2c(n1)CCC2Cl]

To a stirred solution of 2-(trifluoromethyl)-6,7-dihydro-5H-cyclopenta[b]pyridin-5-ol (56.3 mg, 0.277 mmol) in DCM (15 mL) was added SOCl₂ (0.020 mL, 0.277 mmol) at 0° C. The reaction mixture was stirred at room temperature for 30 min. and then evaporated under reduced pressure to get residue. The crude compound used directly for the next step.

Scheme-8

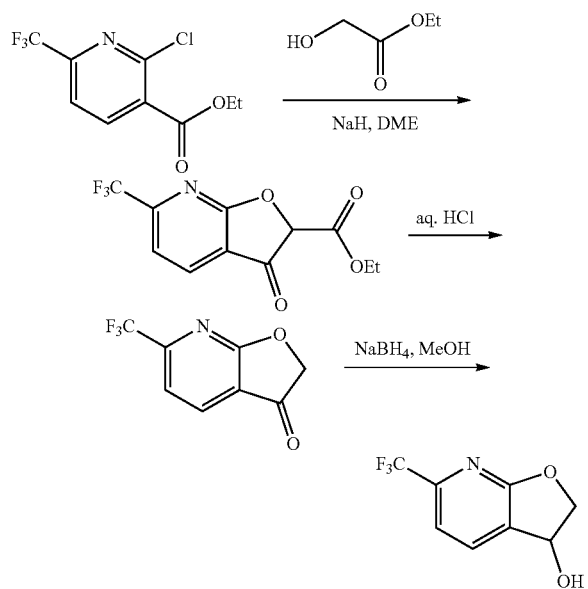

a) Ethyl 3-oxo-6-(trifluoromethyl)-2,3-dihydrofuro[2,3-b]pyridine-2-carboxylate

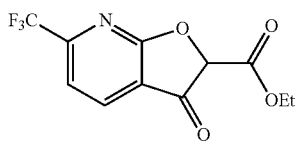

To a solution of ethyl 2-hydroxyacetate (19.50 g, 187 mmol) in 1,2-dimethoxyethane (DME) (200 mL) was added NaH (4.49 g, 187 mmol) at 0° C. and then solution of ethyl 2-chloro-6-(trifluoromethyl)nicotinate (19 g, 74.9 mmol) in 1,2-dimethoxyethane (DME) (200 mL) was added to the reaction mixture at RT. The resulting reaction mixture was stirred at 75° C. for 2 h. The reaction mixture was quenched with saturated sodium bicarbonate, extracted with EtOAc. The organic layer was washed successively with water and brine, dried over MgSO₄, and concentrated in vacuo to get crude. The residue was purified by silica gel column chromatography (EtOAc/Pet ether) to afford the title compound (9.6 g) as yellow solid. LCMS (ES) m/z 276.07 [M+H]⁺.

b) 6-(Trifluoromethyl)furo[2,3-b]pyridin-3(2H)-one

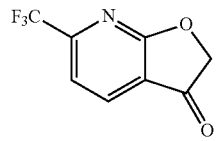 [SMILES: O=C1COc2nc(C(F)(F)F)ccc21]

To a solution of ethyl 3-oxo-6-(trifluoromethyl)-2,3-dihydrofuro[2,3-b]pyridine-2-carboxylate (4 g, 14.54 mmol) in 1,4-dioxane (40 mL) was added HCl (11.04 mL, 363 mmol) at RT. The reaction mixture was heated to 100° C. for 24 h. The reaction mixture was quenched with saturated sodium bicarbonate and extracted with EtOAc. The organic layer was washed successively with water and brine, dried over MgSO₄, and concentrated in vacuo to give the title compound (1.5 g) as yellow solid. The crude compound used for the next step without further purification. LCMS (ES) m/z 203.78 [M+H]⁺.

d) 6-(Trifluoromethyl)-2,3-dihydrofuro[2,3-b]pyridin-3-ol

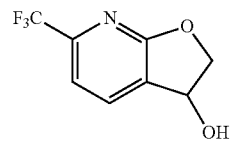

The title compound was prepared as a white solid according to the procedures of Scheme 7, Step h, LCMS (ES) m/z 206.10 [M+H]⁺.

Scheme-9

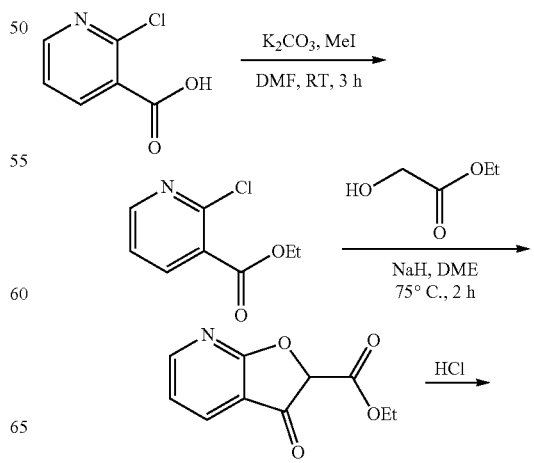

63

-continued

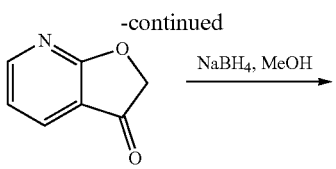

a) Ethyl 2-chloronicotinate

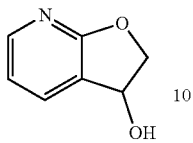

To a stirred solution of 2-chloronicotinic acid (25 g, 159 mmol) in DMF (300 mL) was added MeI (11.91 mL, 190 mmol), $K_2CO_3$ (54.8 g, 397 mmol) at rt. The reaction mixture was stirred at RT for 3 h. The Reaction mixture was diluted with EtOAc (500 mL) washed with water (4×500 mL) and brine (500 mL). Organic layer was dried over anhydrous sodium sulphate filtered and concentrated to afford ethyl 2-chloronicotinate (26 g, yield 95%) as off white solid. $^1$H NMR (400 MHz, $CDCl_3$): δ 8.53-8.51 (m, 1H), 8.18-15 (m, 1H), 7.34-7.31 (m, 1H), 4.0 (s, 3H); LCMS (ES) m/z 171.94 [M+H]±.

b) Ethyl 3-oxo-2,3-dihydrofuro[2,3-b]pyridine-2-carboxylate

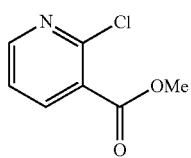 [SMILES: COC(=O)c1cccnc1Cl]

To a stirred suspension of NaH (10.91 g, 455 mmol) in 1,2-dimethoxyethane (1200 mL) was added ethyl 2-hydroxyacetate (39.4 g, 379 mmol) at 0° C. Reaction mixture was stirred at RT for 30 min. After that methyl 2-chloronicotinate (26 g, 152 mmol) in DME (150 mL) was added to the reaction mixture and the resulting mixture was heated at 75° C. for 2 h. Reaction mixture was concentrated. The crude was basified with saturated sodium bicarbonate and washed with EtOAc (1×500 mL). Aqueous layer was acidify with acetic acid, extracted with DCM (2×500 mL), washed with water (500 mL) and brine (500 mL). Organic layer was dried over anhydrous sodium sulphate filtered and concentrated. The crude residue was purified by column chromatography (100-200 mesh silica). Compound Eluted at 12% EtOAc in hexane. The eluents were concentrated at reduced pressure and to affording ethyl 3-oxo-2,3-dihydrofuro[2,3-b]pyridine-2-carboxylate (16 g, yield 35.2%) as off white solid. LCMS (ES) m/z 207.96 [M+1]$^+$.

64 c) Furo[2,3-b]pyridin-3(2H)-one

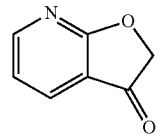

To a stirred solution of ethyl 3-oxo-2,3-dihydrofuro[2,3-b]pyridine-2-carboxylate (12 g, 57.9 mmol) in HCl (9.65 ml, 57.9 mmol) was stirred at 100° C. for 1 h. Reaction mixture was basify with sat sodium bicarbonate diluted with EtOAc (500 mL) washed with water (200 mL) and brine (200 mL). Organic layer was dried anhydrous sodium sulphate filtered and concentrated. Crude was purified by column chromatography (100-200 mesh silica) to afford furo[2,3-b]pyridin-3(2H)-one (8 g, yield 84%) as off white solid. $^1$H NMR (500 MHz, $CDCl_3$): δ 8.59-8.58 (m, 1H), 8.06-8.04 (m, 1H), 7.16-7.14 (m, 1H), 4.75 (s, 2H). LCMS (ES) m/z 136.07 [M+H]$^+$.

d) 2,3-Dihydrofuro[2,3-b]pyridin-3-ol

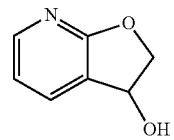

To a stirred solution of furo[2,3-b]pyridin-3(2H)-one (8 g, 59.2 mmol) in methanol (80 mL) was added $NaBH_4$ (2.24 g, 59.2 mmol) at 0° C. Reaction mixture was stirred at RT for 3 h. The reaction mixture was diluted with EtOAc (200 mL) washed with water (200 mL) and brine (200 mL). Organic layer was dried anhydrous sodium sulphate filtered and concentrated. Crude was purified by column chromatography (100-200 mesh silica gel) and the compound eluted at 80% EtOAc in hexane. Eluents were concentrated to affording 2,3-dihydrofuro[2,3-b]pyridin-3-ol (4 g, 47.7%) as off white solid. $^1$H NMR (500 MHz, DMSO-$d_6$) δ 8.06-8.05 (m, 1H), 7.77-7.75 (m, 1H), 6.95-6.92 (m, 1H), 5.77-5.76 (d, J=6 Hz, 1H), 5.30-5.27 (m, 1H), 4.57-4.54 (m, 1H), 4.24-4.21 (m, 1H). LCMS (ES) m/z 138.12 [M+H]$^+$.

Example 1

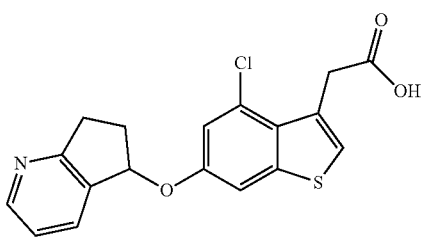 [SMILES: O=C(O)Cc1csc2cc(OC3CCc4ncccc43)cc(Cl)c12]

Preparation of 2-(4-chloro-6-((6,7-dihydro-5H-cyclopenta[b]pyridin-5-yl)oxy)benzo[b]thiophen-3-yl)acetic acid a) Ethyl 2-(4-chloro-6-(6,7-dihydro-5H-cyclopenta[b]pyridin-5-yloxy)benzo[b]thiophen-3-yl)acetate

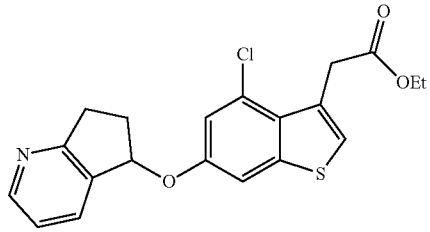 [SMILES: CCOC(=O)Cc1csc2cc(OC3CCc4ncccc43)cc(Cl)c12]

To a stirred solution of ethyl 2-(4-chloro-6-hydroxybenzo[b]thiophen-3-yl)acetate (5 g, 18.47 mmol) and 5-chloro-6,7-dihydro-5H-cyclopenta[b]pyridine (4.26 g, 27.7 mmol) in DMF (50 mL) was added $K_2CO_3$ (12.76 g, 92 mmol) at RT. The reaction mixture was heated to 80° C. for 1 h. The mixture was diluted with water and extracted with EtOAc. The organic layer was washed successively with water and brine, dried over $MgSO_4$, and concentrated in vacuo to get crude. The residue was purified by silica gel column chromatography (EtOAc/hexane) to give the title compound (6.5 g) as brown gummy liquid. LCMS (ES) m/z 388.17 $[M+H]^+$.

b) 2-(4-Chloro-6-((6,7-dihydro-5H-cyclopenta[b]pyridin-5-yl)oxy)benzo[b]thiophen-3-yl)acetic acid

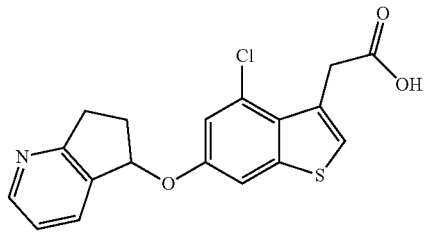

To a stirred solution of ethyl 2-(4-chloro-6-((6,7-dihydro-5H-cyclopenta[b]pyridin-5-yl)oxy)benzo[b]thiophen-3-yl)acetate (40 g, 103 mmol) in THF (200 mL), methanol (200 mL) and water (100 mL) was added lithium hydroxide (monohydrate) (12.35 g, 516 mmol) at RT and the reaction mixture was stirred at 25° C. for 1 h. The reaction mixture was neutralized with dilute HCl carefully and the precipitated compound was filtered and dried under reduced pressure to obtained 2-(4-chloro-6-((6,7-dihydro-5H-cyclopenta[b]pyridin-5-yl)oxy)benzo[b]thiophen-3-yl)acetic acid (32 g, 86% yield) as an off-white solid. $^1$H NMR (500 MHz, DMSO-$d_6$) δ 12.5 (brs, 1H), 8.50 (dd, J=1.2, 4.5 Hz, 1H), 7.78-7.82 (m, 2H), 7.47 (s, 1H), 7.22-7.20 (m, 1H), 7.13 (d, J=2.1 Hz, 1H), 6.00-6.04 (m, 1H), 4.00 (s, 2H), 3.06-3.11 (m, 1H), 2.89-2.99 (m, 1H), 2.62-2.72 (m, 1H), 2.06-2.15 (m, 1H). LCMS (ES) m/z 360.05 $[M+H]^+$. Chiral HPLC: 49.92%: 50.08%

Analytical SFC Condition
Column/dimensions:Chiralpak AD-H (250×4.6)mm, 5μ
% CO2: 60.0%
% Co solvent: 40.0% (100% MeOH)
Total Flow: 3.0 g/min
Back Pressure: 100 bar
Temperature: 30.0° C.
UV: 237 nm
Preparative SFC Condition
Column/dimensions: Chiralpak AD-H (250×21) mm, 5μ
% $CO_2$: 65.0%
% Co solvent: 35.0% (100% Methanol)
Total Flow: 60.0 g/min
Back Pressure: 100.0 bar
UV: 284 nm
Stack time: 8.8 min
Load/Inj: 15.0 mg
Retention time: Peak 1—3.15 min, Peak 2-3.73 min.
Purity: Peak 1—99.73%, Peak 2-98.00%.
Solubility: Methanol+ACN+DCM+THF Chiral Separation of Example 1

Example 1a (First Eluted Enantiomer)

(S)-2-(4-chloro-6-((6,7-dihydro-5H-cyclopenta[b]pyridin-5-yl)oxy)benzo[b]thiophen-3-yl)acetic Acid (11 g, 34.3% yield). LCMS (ES) m/z 360.18 $[M+H]^+$. $^1$H NMR (300 MHz, DMSO-$d_6$): δ 12.4 (brs, 1H), 8.50 (dd, J=1.2, 4.8 Hz, 1H), 7.78-7.83 (m, 2H), 7.49 (s, 1H), 7.23-7.20 (m, 1H), 7.13 (d, J=2.1 Hz, 1H), 6.00-6.04 (m, 1H), 4.01 (s, 2H), 3.06-3.11 (m, 1H), 2.95-2.98 (m, 1H), 2.66-2.68 (m, 1H), 2.09-2.12 (m, 1H). Chiral HPLC: 99.73%. Absolute stereochemistry was determined by vibrational circular dichroism (VCD).

Example 1b (Second Eluted Enantiomer)

(R)-2-(4-chloro-6-((6,7-dihydro-5H-cyclopenta[b]pyridin-5-yl)oxy)benzo[b]thiophen-3-yl)acetic acid (10.3 g, 32.1% yield) as an off white solids. LCMS (ES) m/z 360.15 (M+H)±. $^1$H NMR (300 MHz, DMSO-$d_6$): δ 12.4 (brs, 1H), 8.50 (dd, J=1.2, 4.8 Hz, 1H), 7.78-7.83 (m, 2H), 7.49 (s, 1H), 7.23-7.20 (m, 1H), 7.13 (d, J=2.1 Hz, 1H), 6.00-6.04 (m, 1H), 4.01 (s, 2H), 3.06-3.11 (m, 1H), 2.95-2.98 (m, 1H), 2.66-2.68 (m, 1H), 2.09-2.12 (m, 1H). Chiral HPLC: 98.00%.

Chiral Synthesis of Example 1a, (S)-2-(4-chloro-6-((6,7-dihydro-5H-cyclopenta[b]pyridin-5-yl)oxy)benzo[b]thiophen-3-yl)acetic Acid Scheme-13

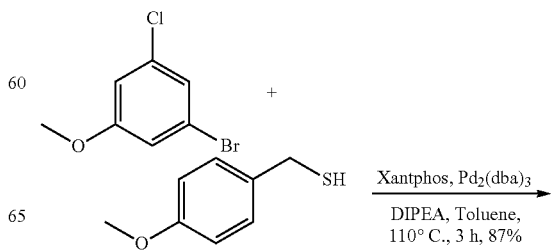

a) (3-Chloro-5-methoxyphenyl)(4-methoxybenzyl)sulfane

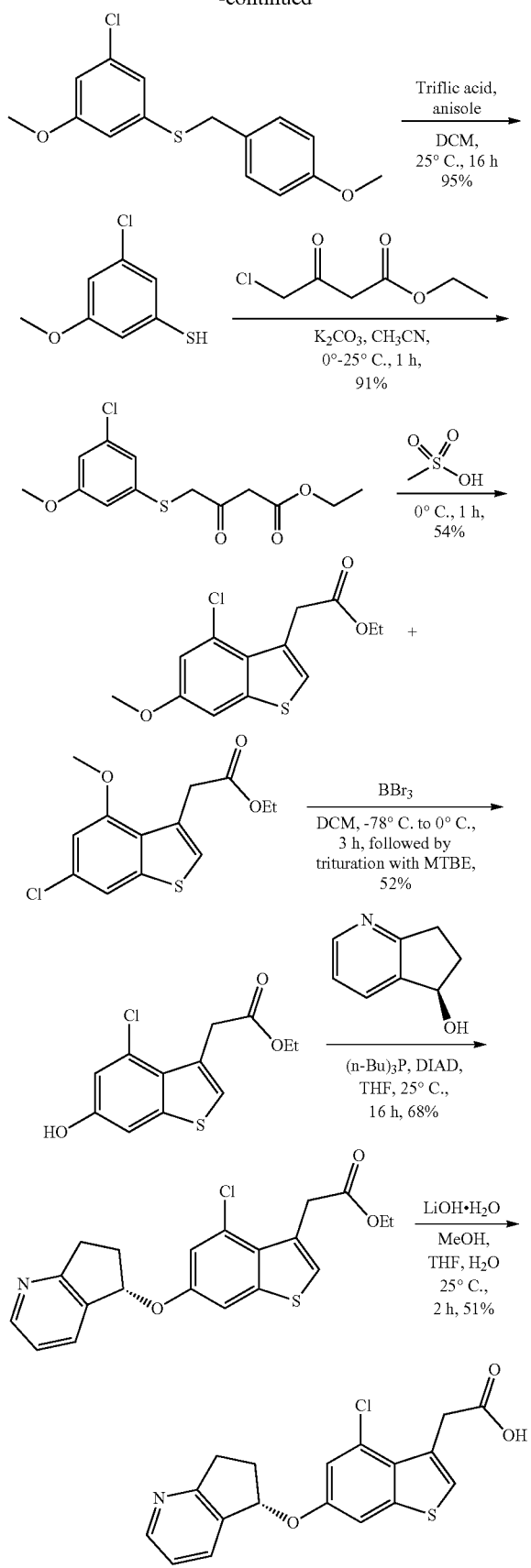

A 250 L reactor was charged with 1-bromo-3-chloro-5-methoxybenzene (7.5 kg, 33864.6 mmol) and (4-methoxyphenyl)methanethiol (5.74 kg, 37217.3 mmol). Toluene (30 L) was charged to the reaction mass. DIPEA (11.83 L, 67701.9 mmol) was added at 25° C. slowly into the above reaction mixture. The reaction mixture was degassed with $N_2$ for 20 min. $Pd_2(dba)_3$ (1.55 kg, 1692.66 mmol) and xantphos (0.980 kg, 1692.66 mmol) were added slowly into above reaction mixture (Note: The reaction mass color changes pale yellow to dark color). The reaction mixture was again degassed with $N_2$ for 15 min. The reaction mass was stirred at 110° C. for 3 h. Completion of the reaction was monitored by TLC (5% EtOAc in pet ether, $R_f$ value of the product is 0.5). After completion of reaction, the reaction mass was cooled to 25° C. and filtered on a Celite® bed. The Celite® bed was washed with EtOAc. DM water was added to the filtrate and stirred at 25-30° C. for 5-10 min. The combined layers were transferred to a 250 L reactor. The Aqueous and EtOAc layers were separated. Sodium chloride solution was added to the EtOAc and stirred at 25-30° C. for 5-10 min. The combined layers were transferred to 250 L reactor. The aqueous and EtOAc layers were separated. The EtOAc layer was dried over anhydrous $Na_2SO_4$ and filtered. $Na_2SO_4$ washed with EtOAc. The EtOAc was transferred to a 250 L reactor and evaporated below 40-45° C. under vacuum. After completion of evaporation, the thick yellow liquid was subjected to drying by rotary evaporation at 40-45° C. for 1.0 h. drying was terminated and the thick yellow liquid was obtained (13.5 kg, crude). A chromatography column was packed with silica gel (20.0 kg, 100-200 mesh). The crude compound dissolved in DCM and loaded into the column. Run the mobile phase with hexane (50 L). Then followed by increasing the polarity from 2-5% EtOAc in hexane (500 L). All pure fractions (by TLC) collected and concentrated under reduced pressure at 40-45° C. (8.7 kg, yield 87.17%). $^1$H NMR (400 MHz, $CDCl_3$) δ 7.25-7.22 (m, 2H), 6.87-6.82 (m, 3H), 6.69-6.67 (m, 2H), 4.08 (s, 2H), 3.78 (s, 3H), 3.73 (s, 3H).

b) 3-Chloro-5-methoxybenzenethiol

A 100 L reactor was charged with a solution of 3-chloro-5-methoxyphenyl(4-methoxybenzyl)sulfane (4.6 kg, 15604.01 mmol) in DCM (46 L). Anisole (15.35 kg, 141945.6 mmol) was added to the reaction mass and cooled to 0° C. Trifluoromethanesulfonic acid (1.38 L, 15604 mmol) was added dropwise to the reaction mass at 0-5° C. for 20 min (Note: The reaction mass color changed from pale yellow to red color). The reaction mass was stirred at 25° C. for 16 h under N$_2$ atmosphere. The reaction was monitored by TLC (5% EtOAc in pet ether, R$_f$ value of the product is 0.6). After completion of reaction, the reaction mass was cooled to 0° C. 2N NaOH solution was added dropwise to the reaction mass at 0-10° C. until the pH of the reaction mass was ~13. The resulting mixture stirred at 25° C. for 30 min and settled for 10 min. The aqueous and organic layers were separated. The aqueous layer was cooled to 0° C. and acidified to pH~2 with 2M HCl. EtOAc was added and resulting mixture stirred at 25° C. for 30 min. EtOAc layer was separated and the aqueous layer again extracted with EtOAc. The combined EtOAc layers were washed with DM water and the organic layer was separated. The organic layer was washed with sodium chloride solution (1.79 kg of NaCl in 17.94 L of water). The EtOAc layer was dried over anhydrous Na$_2$SO$_4$ and filtered. The EtOAc layer was evaporated below 40° C. After completion of evaporation, the thick yellow liquid was subjected to drying by rotary evaporation at 40-45° C. for 1.0 h. Drying was terminated and a pale yellow liquid was obtained (2.6 kg, yield 95%). $^1$H NMR (300 MHz, CDCl$_3$) δ 6.85 (d, J=2.4 Hz, 1H), 6.70 (s, 2H), 3.78 (s, 3H), 3.50 (s, 1H).

c) Ethyl 4-((3-chloro-5-methoxyphenyl)thio)-3-oxobutanoate

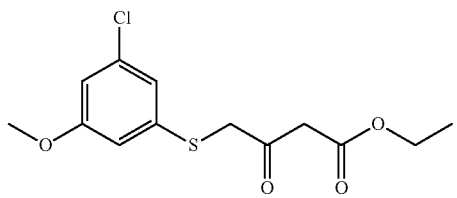 [SMILES: CCOC(=O)CC(=O)CSc1cc(Cl)cc(OC)c1]

A 100 L reactor was charged with a solution of 3-chloro-5-methoxybenzenethiol (2.6 kg, 1489 mmol) in acetonitrile (19.5 L). K$_2$CO$_3$ (3.09 kg, 2235 mmol) was added to the reaction mass at 0° C. under N$_2$ atmosphere and stirred at same temperature for 10 min (Note: After addition of K$_2$CO$_3$, the reaction mass color changed from pale yellow to white color). Ethyl 4-chloroacetoacetate (2.7 kg, 1545 mmol) was added dropwise to the reaction mass at 0-10° C. for 20 min. The reaction mass was stirred at 25° C. for 1 h under N$_2$ atmosphere (Note: After 1 h stirring, the reaction mass color changed from white to brown color). The reaction was monitored by TLC (10% EtOAc in pet ether, R$_f$ value of the product is 0.3). After completion of the reaction, the reaction mass was cooled to 0° C. DM water was added slowly to the reaction mass at 0-10° C. EtOAc was added and the resulting mixture stirred at 25° C. for 10 min. The aqueous and organic layers were separated. The EtOAc layer was washed with 10% sodium chloride solution. The aqueous and organic layers were separated. The EtOAc layer was dried over anhydrous Na$_2$SO$_4$ and filtered. The Na$_2$SO$_4$ was washed with EtOAc. The EtOAc layer was evaporated below 40° C. Drying was terminated and a dark color liquid was obtained (4.1 kg, yield 91%). $^1$H NMR (400 MHz, CDCl$_3$) δ 6.90 (d, J=2.4 Hz, 1H), 6.75 (s, 2H), 4.20-4.18 (m, 2H), 3.82 (s, 2H), 3.78 (s, 3H), 3.61 (s, 2H), 1.26 (m. 3H).

d) Ethyl 2-(4-chloro-6-methoxybenzo[b]thiophen-3-yl)acetate and ethyl 2-(6-chloro-4-methoxybenzo[b]thiophen-3-yl)acetate

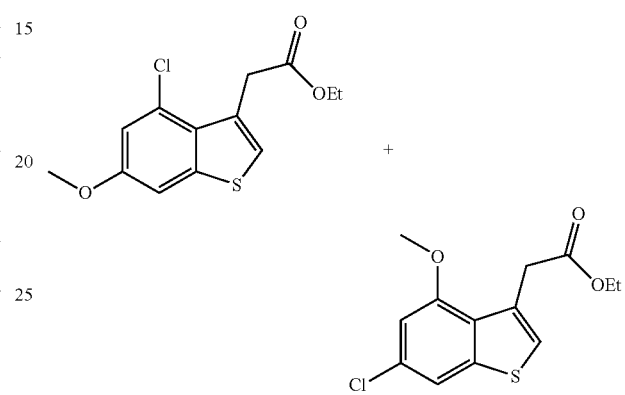

A 20 L 4-neck round bottom flask was charged with methanesulfonic acid (9.52 L) and cooled to 0° C. Ethyl 4-(3-chloro-5-methoxyphenylthio)-3-oxobutanoate (4.0 kg, 13211 mmol) was added at 0° C. slowly dropwise into the above reaction mixture under nitrogen atmosphere for 50 min and stirred at 0° C. for 20 min (Note: The reaction mixture turns a dark black color). The reaction mass was slowly allowed to attain 25° C. The reaction mass was stirred at 25° C. for 1 h. Completion of the reaction was monitored by TLC. (10% EtOAc in pet ether, R$_f$ value of the product is 0.4). After completion of the reaction, the reaction mass was poured into ice cold water. EtOAc was added and the resulting mixture stirred at 25° C. for 10 min. The aqueous and EtOAc layers were separated. The aqueous layer was again extracted with EtOAc. The combined EtOAc layers were washed with DM water and the organic layer was separated. The EtOAc layer was washed with 10% sodium chloride solution. The EtOAc layer was dried over anhydrous Na$_2$SO$_4$ and filtered. The Na$_2$SO$_4$ was washed with EtOAc. The EtOAc was evaporated below 40-45° C. under vacuum. After completion of evaporation, the thick yellow liquid was subjected to drying by rotary evaporation at 40-45° C. for 1.0 h. Drying was terminated and a thick black liquid was obtained (3.5 kg). A chromatography column was packed with silica gel (12 kg, 100-200 mesh). The crude compound was dissolved in DCM and loaded onto the column. The mobile phase was run with hexane (50 L) followed by increasing the polarity from 2-10% EtOAc in hexane (100 L). All pure fractions (by TLC) collected and concentrated under reduced pressure at 40-45° C. to afford a mixture of two regioisomeric compounds (2.0 kg, yield 54% as a mixture, ratio 3:1). LCMS (ES) m/z 285.12 [M+H]$^+$.

e) Ethyl 2-(4-chloro-6-hydroxybenzo[b]thiophen-3-yl)acetate

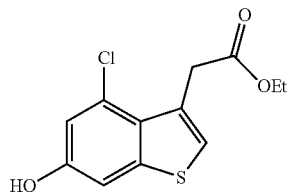 [SMILES: CCOC(=O)Cc1csc2cc(O)cc(Cl)c12]

A 20 L 4-neck round bottom flask was charged with a mixture of ethyl 2-(4-chloro-6-methoxybenzo[b]thiophen-3-yl)acetate and ethyl 2-(6-chloro-4-methoxybenzo[b]thiophen-3-yl)acetate (mixture 1.0 kg, 3511 mmol) in DCM (9 L). The reaction mass was cooled to −78° C. BBr$_3$ (neat, 663.85 mL, 6605.54 mmol) was added at −78° C. slowly dropwise into the above reaction mixture under nitrogen atmosphere for 45 min and stirred at −78° C. for 20 min (Note: The reaction mixture turned brick red and precipitation was observed on the walls of RB flask). The reaction mixture was allowed to attain 0° C. and stirred for 2 h (Note: The reaction mixture turned brick red and precipitation to wine red color liquid observed). Progress of the reaction was monitored by TLC. (10% EtOAc in pet ether, R$_f$ value of the product is 0.3). After completion of the reaction, the reaction mass was poured into ice cold water slowly dropwise. (Note: Exothermic reaction while quenching of reaction). DCM was added to the above reaction mixture and the resulting mixture was stirred at 25° C. for 10 min. The aqueous and DCM layers were separated. The aqueous layer was again extracted with DCM. The combined organic layers were washed with DM water and the organic layer was separated and again washed with DM water. The combined organic layers were washed with sodium chloride solution. The organic layer was dried over anhydrous Na$_2$SO$_4$, filtered, and evaporated below 35-40° C. under vacuum. After completion of evaporation, the orange red color solid was subjected to drying by rotary evaporation at 40-45° C. for 1.0 h. Drying was terminated and an orange red color solid was obtained (800 g, crude) as a mixture of isomers with a ratio of 7:2. The crude solid (mixture of isomers) was taken up in MTBE (2000 mL) and stirred at 25° C. for 30 min then cooled to 0° C. for 20 min. The solid was collected by filtration, washed with cold MTBE (500 mL), and dried by suction to afford ethyl 2-(4-chloro-6-hydroxybenzo[b]thiophen-3-yl)acetate as an off-white solid (500 g, yield 52%). $^1$H NMR (400 MHz, DMSO-d$_6$) δ 9.98 (s, 1H) 7.39 (s, 1H), 7.31 (d, J=2.4 Hz, 1H), 6.87 (d, J=2.4 Hz, 1H), 4.24 (q, J=9.2 Hz, 2H), 4.08 (s, 2H), 1.30 (t, J=6.9 Hz, 3H). LCMS (ES) m/z 271.15 [M+H]$^+$.

f) Ethyl (S)-2-(4-chloro-6-((6,7-dihydro-5H-cyclopenta[b]pyridin-5-yl)oxy)benzo[b]thiophen-3-yl)acetate

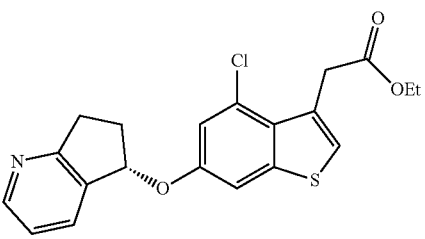

A 5 L 4-neck round bottom flask was charged with a mixture of (R)-6,7-dihydro-5H-cyclopenta[b]pyridin-5-ol (107 g, 791.79 mmol, see Scheme-14 for preparation) in THF (2.14 L). Ethyl 2-(4-chloro-6-hydroxybenzo[b]thiophen-3-yl)acetate (214 g, 791.79 mmol) was added at 25° C. (Note: The reaction mixture turns a brown color). Tri-n-butylphosphine (480 g, 2374.93 mmol) and DIAD (480 g, 2374.93 mmol) were added at 25° C. The reaction mass was stirred at 25° C. for 16 h (Note: Reaction mixture turns a brown color liquid). Completion of the reaction was monitored by TLC. (50% EtOAc in pet ether, R$_f$ value of the product is 0.4). After completion of the reaction, the reaction mass was quenched with ice cold water slowly. EtOAc was added to the above reaction mixture and the resulting mixture stirred at 25° C. for 10 min. The Aqueous and EtOAc layers were separated. The aqueous layer was again extracted with EtOAc. The aqueous and EtOAc layers were separated. The combined organic layers were washed with DM water and the organic layer was separated. The organic layer was washed with sodium chloride solution. The EtOAc layer was dried over anhydrous Na$_2$SO$_4$ and filtered. EtOAc was evaporated below 40-45° C. under vacuum. After completion of evaporation, the black color liquid was subjected to drying by rotary evaporation at 40-45° C. for 1.0 h. Drying was terminated and a brown color gum was obtained (400 g). A chromatography column was packed with silica gel (700 g, 100-200 mesh). The crude compound was dissolved in DCM and adsorbed onto silica gel (300 g) and loaded onto the column. The mobile phase was run with n-hexane (20 L) followed by increasing the polarity from 2-10% EtOAc in hexane (60 L). All pure fractions (by TLC) were collected and concentrated under reduced pressure at 40-45° C. to obtain pure product (210 g, yield 68%). $^1$H NMR (400 MHz, CDCl$_3$) δ 8.60 (d, J=4.8 Hz, 1H), 7.70 (d, J=4.8 Hz, 1H), 7.49 (s, 1H), 7.23-7.28 (m, 2H), 7.13 (d, J=2.1 Hz, 1H), 5.81-5.80 (m, 1H), 4.21-4.20 (q, 2H), 4.01 (s, 2H), 3.30-3.20 (m, 1H), 3.10-3.00 (m, 1H), 2.66-2.68 (m, 1H), 2.12-2.10 (m, 1H), 1.30 (t, J=6.9 Hz, 3H). LCMS (ES) m/z 388.08 [M+H]$^+$.

g) (S)-2-(4-chloro-6-((6,7-dihydro-5H-cyclopenta[b]pyridin-5-yl)oxy)benzo[b]thiophen-3-yl)acetic acid

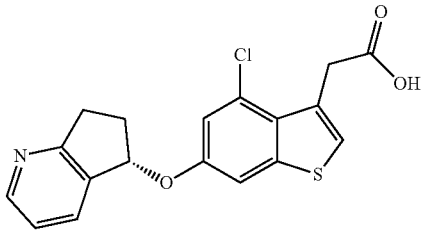 [SMILES: O=C(O)Cc1csc2cc(O[C@H]3CCc4ncccc43)cc(Cl)c12]

A 10 L 4-neck round bottom flask was charged with (S)-ethyl 2-(4-chloro-6-((6,7-dihydro-5H-cyclopenta[b]pyridin-5-yl)oxy)benzo[b]thiophen-3-yl)acetate (400 g, 1031 mmol) in THF (2 L), methanol (2 L), and DM water (1 L) at 25° C. Lithium hydroxide (123 g, 5156 mmol) was added at 25° C. slowly into the above reaction mixture (Note: The reaction mixture turned a brown color). The reaction mass was stirred at 25° C. for 2 h. The reaction was monitored by TLC (80% EtOAc in pet ether, $R_f$ value of the product is 0.2). After completion of the reaction, the reaction mass was poured into ice cold water. The reaction mass was acidified with 10% $NaHSO_4$ pH~6 solution and a white precipitate formed. The solid was collected by filtration, washed with DM water, and dried by suction. The solid was washed with diethyl ether and dried for 2 h. The solid was further dried by rotary evaporation below 45-50° C. under vacuum for 10 h. The solid compound was further triturated with MTBE, filtered, and dried to obtain the desired compound as an off-white solid (190 g, yield 51%). $^1$H NMR (300 MHz, DMSO-$d_6$) δ 12.3-12.4 (br, 1H), 8.50-8.52 (dd, J=1.2, 4.8 Hz, 1H), 7.78-7.83 (m, 2H), 7.49 (s, 1H), 7.23-7.28 (m, 1H), 7.13 (d, J=2.1 Hz, 1H), 6.00-6.04 (m, 1H), 4.01 (s, 2H), 3.06-3.11 (m, 1H), 2.95-2.98 (m, 1H), 2.66-2.68 (m, 1H), 2.09-2.12 (m, 1H). LCMS (ES) m/z 359.98 [M+H]$^+$. Chiral HPLC: 99.70%.

Scheme-14

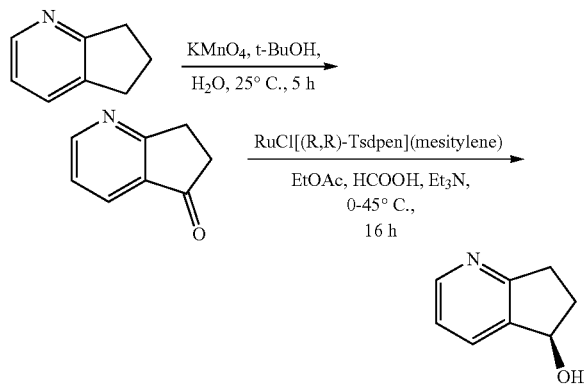

a) 6,7-Dihydro-5H-cyclopenta[b]pyridin-5-one

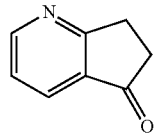

A 50 L glass reactor was charged $KMnO_4$ (1857 g, 11748.0 mmol). Water (35 L) was charged to the reaction mass. The reaction mass was stirred for 30 min (Note: $KMnO_4$ completely soluble in water). Another 100 L reactor was charged 6,7-dihydro-5H-cyclopenta[b]pyridine (700 g, 5874 mmol) in tert-butanol (17.5 L) at 25° C. $MgSO_4$ (1414 g, 11748 mmol) was charged to the above reaction mixture. The reaction mixture was cooled to 20-25° C. with ice water. $KMnO_4$ solution was added dropwise for 2 h (Note: Slight exothermic was observed and temperature maintained below 30° C. with ice water). The reaction mixture was maintained at 30° C. for 3 h. Progress of the reaction was monitored by TLC/LCMS (50% EtOAc in pet ether, $R_f$ value of the product is 0.3). After completion of the reaction, EtOAc was added to the above reaction mixture and the resulting mixture stirred at 25° C. for 10 min. The aqueous and EtOAc layers were separated. The aqueous layer was again extracted with EtOAc. The combined organic layers were washed with DM water and the organic layer was separated. The combined organic layers were washed with sodium chloride solution. The EtOAc layer was dried over anhydrous $Na_2SO_4$ and filtered. EtOAc was evaporated below 40-45° C. under vacuum. After completion of evaporation, the brown color liquid was subjected to drying by rotary evaporation at 40-45° C. for 1.0 h. Drying was terminated and a brown color gum was obtained (600 g). A chromatography column was packed with silica gel (4.0 kg, 100-200 mesh). The crude compound was dissolved in DCM and adsorbed onto silica gel (1.0 kg) and loaded onto the column. The mobile phase was run with n-hexane (25 L) followed by increasing the polarity from 2-10% EtOAc in hexane (100 L). All pure fractions (TLC) were collected and concentrated under reduced pressure at 40-45° C. to give 6,7-dihydro-5H-cyclopenta[b]pyridin-5-one as a brown thick gum (270 g, yield 34%). $^1$H NMR (400 MHz, $CDCl_3$) δ 8.45 (dd, J=1.5, 4.5 Hz, 1H), 8.02 (dd, J=2.0, 8.0 Hz, 1H), 7.46-7.44 (m, 1H), 3.19-3.16 (m, 2H), 2.73-2.71 (m, 2H). LCMS (ES) m/z 134.07 [M+H]$^+$.

b) (R)-6,7-dihydro-5H-cyclopenta[b]pyridin-5-ol

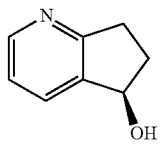

A 5 L 4-neck round bottom flask was charged 6,7-dihydro-5H-cyclopenta[b]pyridine-5-one (100 g, 751.04 mmol) in EtOAc (2 L). TEA (523 mL, 3755.2 mmol) was added at 25° C. slowly into the above reaction mixture. The reaction mass was cooled to 0° C. and formic acid (346 g, 7510.4 mmol) was added dropwise over 30 min (Note: thick white fumes were observed). The above reaction mixture was stirred at 0° C. for 30 min. RuCl[(R,R)-Tsdpen](mesitylene) (9.36 g, 15.02 mmol) was added at 0° C. The reaction mixture was maintained at 45° C. for 16 h. Progress of the reaction was monitored by TLC. (50% EtOAc in pet ether, $R_f$ value of the product is 0.4). After completion of the reaction, the reaction mass was directly evaporated by rotary evaporation below 40-45° C. under vacuum. A chromatography column was packed with silica gel (500 g, 100-200 mesh). The crude compound was directly loaded onto the column. The mobile phase was run with n-hexane (25 L) followed by increasing the polarity from 2-80% EtOAc in hexane (50 L). All pure fractions (by TLC) were collected and concentrated under reduced pressure at 40-45° C. to give a gummy liquid, which was triturated with diethyl ether (2×100 mL) and filtered by suction to afford (R)-6,7-dihydro-5H-cyclopenta[b]pyridin-5-ol as a pale brown solid (80 g, yield 79%). $^1$H NMR (300 MHz, CDCl$_3$) δ 8.45 (dd, J=1.2, 3.6 Hz, 1H), 7.71 (d, J=7.6 Hz, 1H), 7.14 (q, J=4.8 Hz, 1H), 5.29 (d, J=5.6 Hz, 1H), 3.20-3.12 (m, 2H), 2.98-2.89 (m, 1H), 2.62-2.54 (m, 1H), 2.03-1.98 (m, 1H). LCMS (ES) m/z 136.17 [M+H]$^+$.

Crystalline Compound of Example 1a, (S)-2-(4-chloro-6-((6,7-dihydro-5H-cyclopenta[b]pyridin-5-yl)oxy)benzo[b]thiophen-3-yl)acetic Acid The X-ray powder diffraction (XRPD) pattern of this material is shown in FIG. 1 and a summary of the diffraction angles and d-spacings is given in Table I below. The XRPD analysis was conducted on a PANanalytical X'Pert Pro Diffractometer on Si zero-background wafers using X'celerator™ RTMS (Real Time Multi-Strip) detector. The acquisition conditions included: Cu K$_α$ radiation, generator tension: 45 kV, generator current: 40 mA, step size: 0.0167° 2θ. Configuration on the incidental beam side: 10 mm programmable divergence slit, 0.02 rad Soller slits, anti-scatter slit (0.5°), and 10 mm beam mask. Configuration on the diffracted beam side: 10 mm programmable anti-scatter slit assembly (X'celerator module) and 0.02 rad Soller slit.

TABLE I

| Diff. Angle [°2θ] | d-spacing [Å] |
|---|---|
| 5.876 | 15.0412 |
| 13.6014 | 6.51043 |
| 14.0485 | 6.30422 |
| 14.3468 | 6.17377 |
| 21.8816 | 4.06196 |
| 22.461 | 3.95847 |
| 23.0524 | 3.85824 |
| 23.3301 | 3.81294 |
| 24.1261 | 3.6889 |
| 24.5102 | 3.63196 |
| 24.6985 | 3.6047 |
| 25.6652 | 3.47107 |
| 26.0846 | 3.41621 |
| 26.6086 | 3.35011 |
| 27.4121 | 3.25371 |

The differential scanning calorimetry (DSC) thermogram of this material was recorded on a TA Instruments Discovery Differential Scanning calorimeter equipped with an autosampler and a refrigerated cooling system under 40 mL/min N$_2$ purge and is shown in FIG. 2. The experiments were conducted using a heating rate of 10° C./min to final temperature of 350° C. in a lightly crimped aluminum pan.

The thermogravimetric analysis (TGA) thermogram of this material was recorded on a TA Instruments Discovery Thermogravimetric Analyzer and is shown in FIG. 2. The experiments were conducted under N$_2$ purge and a heating rate of 10° C./min to final temperature of 350° C. in an open aluminum pan.

This compound has a simple single melting event in DSC, with onset temperature of 220.8 C, peak temperature of 223.4 C and melting enthalpy of 120 J/g. The determination of melting enthalpy is not reliable due to the immediate thermal decomposition post melting. The compound exhibited negligible weight loss by loss by TGA prior to the decomposition event. A person skilled in the art would recognize that the onset temperature, peak temperature, and enthalpy of the endotherm may vary depending on the experimental conditions.

Example 2

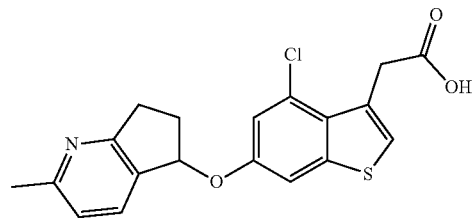 [SMILES: Cc1ccc2c(n1)CCC2Oc1cc(Cl)c2c(CC(=O)O)csc2c1]

Preparation of 2-(4-chloro-6-((2-methyl-6,7-dihydro-5H-cyclopenta[b]pyridin-5-yl)oxy)benzo[b]thiophen-3-yl)acetic Acid a) Ethyl 2-(4-chloro-6-(2-methyl-6,7-dihydro-5H-cyclopenta[b]pyridin-5-yloxy)benzo[b]thiophen-3-yl)acetate

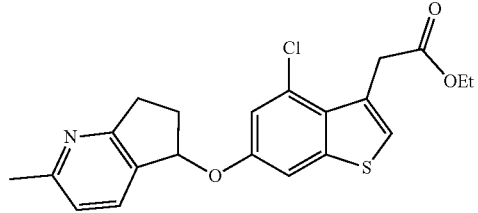 [SMILES: CCOC(=O)Cc1csc2cc(OC3CCc4nc(C)ccc43)cc(Cl)c12]

The crude 5-Chloro-2-methyl-6,7-dihydro-5H-cyclopenta[b]pyridine (25 g) was dissolved in DMF (250 mL) at RT and to this ethyl 2-(4-chloro-6-hydroxybenzo[b]thiophen-3-yl)acetate (25 g, 92 mmol) and K$_2$CO$_3$ (63.8 g, 462 mmol) were added at RT. The reaction mixture was heated to 80° C. for 2 h. The mixture was diluted with water and extracted with EtOAc. The organic layer was washed successively with water and brine, dried over MgSO$_4$ and concentrated in vacuo to get crude. The crude residue was purified by silica gel column chromatography (EtOAc/hexane) to give the title compound (25 g) as an off white solid. LCMS (ES) m/z 402.17 [M+H]$^+$.

b) 2-(4-Chloro-6-((2-methyl-6,7-dihydro-5H-cyclopenta[b]pyridin-5-yl)oxy)benzo[b]thiophen-3-yl)acetic Acid

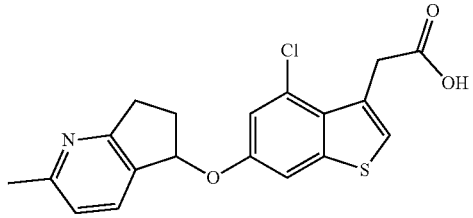 [SMILES: Cc1ccc2c(n1)CCC2Oc1cc(Cl)c2c(CC(=O)O)csc2c1]

The title compound was obtained in a same manner as the procedure in Example 1, Step b by using ethyl 2-(4-chloro-6-(2-methyl-6,7-dihydro-5H-cyclopenta[b]pyridin-5-yloxy)benzo[b]thiophen-3-yl)acetate as an off white solid. $^1$H NMR (300 MHz, DMSO-$d_6$): δ 7.76 (d, J=2.1 Hz, 1H), 7.68 (d, J=8.1 Hz, 1H), 7.47 (s, 1H), 7.11-7.08 (m, 2H), 5.98-5.95 (m, 1H), 4.00 (s, 2H), 3.17-3.01 (m, 1H), 2.93-2.83 (m, 1H), 2.67-2.59 (m, 1H), 2.47 (s, 3H), 2.13-2.04 (m, 1H); LCMS (ES) m/z 374.09 [M+H]$^+$. Chiral HPLC: 49.85%: 50.14%.

Analytical SFC Condition
Column/dimensions: Chiralpak AD-H (250×4.6) mm, 5μ
% CO$_2$: 60.0%
% Co solvent: 40.0% (100% Methanol)
Total Flow: 4.0 g/min
Back Pressure: 100 bar
Temperature: 30.0° C.
UV: 235 nm
Preparative SFC Condition
Column/dimensions: Lux Amylose-1 (250×30) mm, 5μ
% CO$_2$: 55.0%
% Co solvent: 45.0% (100% Methanol)
Total Flow: 90.0 g/min
Back Pressure: 100.0 bar
UV: 235 nm
Stack time: 5.3 min
Load/Inj: 82.0 mg
Retention time: Peak 1—3.02 min, Peak 2—4.93 min.
Purity: Peak 1—99.91%, Peak 2—99.24%.
Solubility: Methanol (660 mL)+12 ml DEA
Instrument details: Make/Model: Thar SFC-200-002

Example 2a (S)-2-(4-chloro-6-((2-methyl-6,7-dihydro-5H-cyclopenta[b]pyridin-5-yl)oxy)benzo[b]thiophen-3-yl)acetic acid (5.1 g, 30.7% yield). $^1$H NMR (300 MHz, DMSO-$d_6$): δ 7.76 (d, J=2.4 Hz, 1H), 7.68 (d, J=7.8 Hz, 1H), 7.47 (s, 1H), 7.11-7.08 (m, 2H), 5.98-5.95 (m, 1H), 4.00 (s, 2H), 3.06-2.89 (m, 2H), 2.64-2.62 (m, 1H), 2.47 (s, 3H), 2.10-2.06 (m, 1H). LCMS (ES) m/z 374.09 [M+H]$^+$. Chiral HPLC: 99.91%.

Example 2b (R)-2-(4-chloro-6-((2-methyl-6,7-dihydro-5H-cyclopenta[b]pyridin-5-yl)oxy)benzo[b]thiophen-3-yl)acetic acid (3.0 g, 18.24% yield). $^1$H NMR (300 MHz, DMSO-$d_6$): δ 7.76 (d, J=2.4 Hz, 1H), 7.68 (d, J=7.8 Hz, 1H), 7.47 (s, 1H), 7.11-7.08 (m, 2H), 5.98-5.95 (m, 1H), 4.00 (s, 2H), 3.06-2.89 (m, 2H), 2.64-2.62 (m, 1H), 2.47 (s, 3H), 2.10-2.06 (m, 1H). LCMS (ES) m/z 374.24 [M+H]$^+$. Chiral HPLC: 99.24%.

Example 3

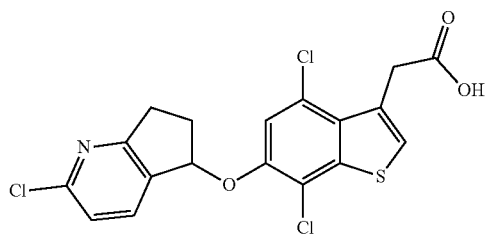 [SMILES: O=C(O)Cc1csc2c(Cl)c(OC3CCc4nc(Cl)ccc43)cc(Cl)c12]

Preparation of 2-(4,7-dichloro-6-((2-chloro-6,7-dihydro-5H-cyclopenta[b]pyridin-5-yl)oxy)benzo[b]thiophen-3-yl)acetic Acid a) Ethyl 2-(4,7-dichloro-6-((2-chloro-6,7-dihydro-5H-cyclopenta[b]pyridin-5-yl)oxy)benzo[b]thiophen-3-yl)acetate

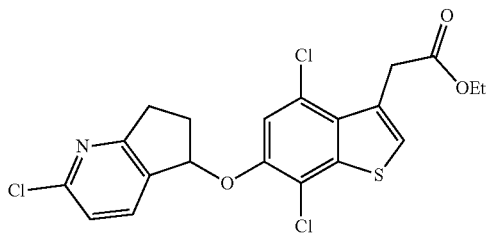 [SMILES: CCOC(=O)Cc1csc2c(Cl)c(OC3CCc4nc(Cl)ccc43)cc(Cl)c12]

To the crude 2,5-dichloro-6,7-dihydro-5H-cyclopenta[b]pyridine (100 mg) dissolved in DMF was added to a stirred solution of ethyl 2-(4,7-dichloro-6-hydroxybenzo[b]thiophen-3-yl)acetate (100 mg, 0.328 mmol) and K$_2$CO$_3$ (181 mg, 1.311 mmol) in DMF (5 mL) at ambient temperature and then heated to 100 for 2 h. After TLC analysis the reaction mixture was diluted with water and extracted with EtOAc. The organic layer was washed with water, brine, dried over Na$_2$SO$_4$ and concentrated under reduced pressure to afford crude. The crude was purified by silica gel chromatography using 30% EtOAc/pet ether as an eluent to afford ethyl 2-(4,7-dichloro-6-((2-chloro-6,7-dihydro-5H-cyclopenta[b]pyridin-5-yl)oxy)benzo[b]thiophen-3-yl)acetate (60 mg, 40.0% yield) as an oily liquid. $^1$H NMR (400 MHz, CDCl$_3$) δ 7.66 (d, J=8.0 Hz, 1H), 7.31-7.18 (m, 3H), 5.78-5.75 (m, 1H), 4.22 (q, J=8 Hz, 2H), 4.09 (s, 2H), 3.35-3.27 (m, 1H), 3.08-3.00 (m, 1H), 2.69-2.64 (m, 1H), 2.42-2.39 (m, 1H), 1.29 (t, J=8 Hz, 3H). LCMS (ES) m/z 456.79 [M+H]$^+$.

b) 2-(4,7-Dichloro-6-((2-chloro-6,7-dihydro-5H-cyclopenta[b]pyridin-5-yl)oxy)benzo[b]thiophen-3-yl)acetic Acid

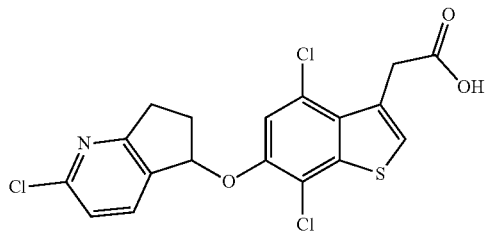 [SMILES: O=C(O)Cc1csc2c(Cl)c(OC3CCc4nc(Cl)ccc43)cc(Cl)c12]

To a stirred solution of ethyl 2-(4,7-dichloro-6-((2-chloro-6,7-dihydro-5H-cyclopenta[b]pyridin-5-yl)oxy)benzo[b]thiophen-3-yl)acetate (60 mg, 0.131 mmol) in methanol (2 mL), THF (2 mL) and water (2 mL), LiOH (6.29 mg, 0.263 mmol) was added at ambient temperature and stirred for 4 h. After TLC analysis the reaction mixture was evaporated to remove solvents and the crude was cooled to 0° C., acidified with saturated citric acid solution ($p^H$~5). Obtained solids were filtered and dried well to afford 2-(4,7-dichloro-6-((2-chloro-6,7-dihydro-5H-cyclopenta[b]pyridin-5-yl)oxy)benzo[b]thiophen-3-yl)acetic acid (46 mg, 81% yield) as an off-white solid. $^1$H NMR (400 MHz, DMSO-$d_6$) δ 12.47 (brs, 1H), 7.83 (d, J=8.0 Hz, 1H), 7.65-7.61 (m, 2H), 7.39 (d, J=8.0 Hz, 1H) 6.10-6.08 (m, 1H), 4.03 (s, 2H), 3.19-3.11 (m, 1H), 2.99-2.92 (m, 1H), 2.71-2.62 (m, 1H), 2.20-2.10 (m, 1H). LCMS (ES) m/z 428 [M+H]$^+$. Chiral HPLC: 48.83%: 51.16%.

Analytical SFC Conditions
Column/dimensions: Chiralpak AD-H (4.6×250 mm), 5μ
% CO$_2$: 60.0%
% Co solvent: 40.0% (100% MeOH)
Total Flow: 4.0 g/min
Back Pressure: 100 bar
Temperature: 30° C.
UV: 235 nm
Preparative SFC Conditions
Column/dimensions: Chiralpak AD-H (30×250 mm), 5μ
% CO$_2$: 50.0%
% Co solvent: 50.0% (100% MeOH)
Total Flow: 90.0 g/min
Back Pressure: 100.0 bar
UV: 235 nm
Stack time: 15.3 min
Load/Inj: 48.3 mg
Retention time: Peak 1—3.59 min, Peak 2—13.34 min.
Purity: Peak 1—99.06%, Peak 2—99.73%.
Solubility: 20 ml MeOH+few drops of methanolic ammonia solution
Instrument details: Make/Model: SFC-200-003

Chiral Separation of Example 3

Example 3a (First Eluted Enantiomer)

$^1$H NMR (400 MHz, DMSO-$d_6$) δ 12.47 (brs, 1H), 7.83 (d, J=8.0 Hz, 1H), 7.65-7.61 (m, 2H), 7.39 (d, J=8.0 Hz, 1H) 6.10-6.08 (m, 1H), 4.03 (s, 2H), 3.19-3.11 (m, 1H), 2.99-2.92 (m, 1H), 2.71-2.62 (m, 1H), 2.20-2.10 (m, 1H). LCMS (ES) m/z 427.9 [M+H]$^+$. Chiral HPLC: 99.06%.

Example 3b (Second Eluted Enantiomer)

$^1$H NMR (400 MHz, DMSO-$d_6$) δ 12.47 (brs, 1H), 7.83 (d, J=8.0 Hz, 1H), 7.65-7.61 (m, 2H), 7.39 (d, J=8.0 Hz, 1H) 6.10-6.08 (m, 1H), 4.03 (s, 2H), 3.19-3.11 (m, 1H), 2.99-2.92 (m, 1H), 2.71-2.62 (m, 1H), 2.20-2.10 (m, 1H). LCMS (ES) m/z 427.99 [M+H]$^+$. Chiral HPLC: 99.77%

Example 4

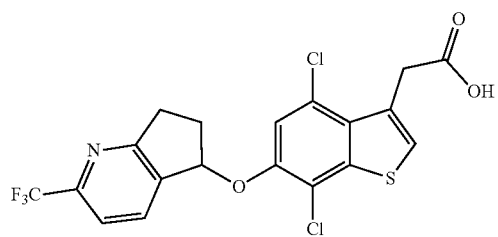 [SMILES: O=C(O)Cc1csc2c(Cl)c(OC3CCc4nc(C(F)(F)F)ccc43)cc(Cl)c12]

Preparation of 2-(4,7-dichloro-6-((2-(trifluoromethyl)-6,7-dihydro-5H-cyclopenta[b]pyridin-5-yl)oxy)benzo[b]thiophen-3-yl)acetic Acid a) Ethyl 2-(4,7-dichloro-6-((2-(trifluoromethyl)-6,7-dihydro-5H-cyclopenta[b]pyridin-5-yl)oxy)benzo[b]thiophen-3-yl)acetate

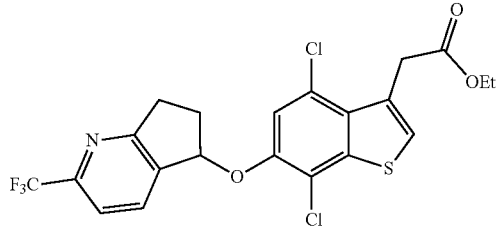 [SMILES: CCOC(=O)Cc1csc2c(Cl)c(OC3CCc4nc(C(F)(F)F)ccc43)cc(Cl)c12]

To the crude 5-Chloro-2-(trifluoromethyl)-6,7-dihydro-5H-cyclopenta[b]pyridine (120 mg) dissolved in DMF was added to a stirred solution of ethyl 2-(4,7-dichloro-6-hydroxybenzo[b]thiophen-3-yl)acetate (100 mg, 0.328 mmol) and K$_2$CO$_3$ (181 mg, 1.311 mmol) in DMF (5 mL) at ambient temperature and then heated to 100° C. for 2 h. After TLC analysis the reaction mixture was diluted with water and extracted with EtOAc. The organic layer was washed with water, brine, dried over Na$_2$SO$_4$ and concentrated under reduced pressure to afford crude. The crude was purified by silica gel chromatography using 30% EtOAc/pet. ether as an eluent to afford ethyl 2-(4,7-dichloro-6-((2-(trifluoromethyl)-6,7-dihydro-5H-cyclopenta[b]pyridin-5-yl)oxy)benzo[b]thiophen-3-yl)acetate (50 mg, 30.9% yield) as an oily liquid. $^1$H NMR (400 MHz, CDCl$_3$) δ 7.88 (d, J=8.0 Hz, 1H), 7.58 (d, J=8 Hz, 1H), 7.26 (s, 1H), 7.20 (s, 1H), 5.82-5.78 (m, 1H), 4.22 (q, J=8 Hz, 2H), 4.10 (s, 2H), 3.42-3.35 (m, 1H), 3.18-3.10 (m, 1H), 2.75-2.69 (m, 1H), 2.46-2.41 (m, 1H), 1.27 (t, J=8 Hz, 3H). LCMS (ES) m/z 490.67 (M+H)$^+$.

b) 2-(4,7-Dichloro-6-((2-(trifluoromethyl)-6,7-dihydro-5H-cyclopenta[b]pyridin-5-yl)oxy)benzo[b]thiophen-3-yl)acetic Acid

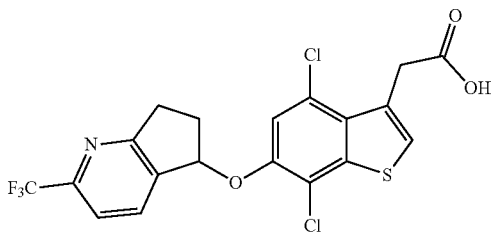 [SMILES: O=C(O)Cc1csc2c(Cl)c(OC3CCc4nc(C(F)(F)F)ccc43)cc(Cl)c12]

To a stirred solution of ethyl 2-(4,7-dichloro-6-((2-(trifluoromethyl)-6,7-dihydro-5H-cyclopenta[b]pyridin-5-yl)oxy)benzo[b]thiophen-3-yl)acetate (50 mg, 0.102 mmol) in methanol (2 mL), THF (2 mL) and water (2 mL), LiOH (4.88 mg, 0.204 mmol) was added at ambient temperature and stirred for 4 h. After TLC analysis the reaction mixture was evaporated to remove solvents and the crude was cooled to 0° C., acidified with saturated citric acid solution (pH~5). Obtained solids were filtered and dried well to afford 2-(4,7-dichloro-6-((2-(trifluoromethyl)-6,7-dihydro-5H-cyclopenta[b]pyridin-5-yl)oxy)benzo[b]thiophen-3-yl)acetic acid (40 mg, 85% yield) as an off-white solid. $^1$H NMR (300 MHz, DMSO-$d_6$) δ 12.48 (brs, 1H), 8.08 (d, J=7.5 Hz, 1H), 7.80 (d, J=7.8 Hz, 1H), 7.70 (s, 1H), 7.63 (s, 1H), 6.21-6.17 (m, 1H), 4.04 (s, 2H), 3.31.3.11 (m, 1H), 3.08-3.01 (m, 1H), 2.79-2.67 (m, 1H), 2.28-2.18 (m, 1H). LCMS (ES) m/z 462.17 [M+H]$^+$. Chiral HPLC 47.52%: 52.47%.

Analytical SFC Condition
Column/dimensions: Chiralpak AD-H (4.6×250 mm), 5µ
% CO$_2$: 60.0%
% Co solvent: 40.0% (100% methanol)
Total Flow: 4.0 g/min
Back Pressure: 100 bar
Temperature: 30° C.
UV: 234 nm
Preparative SFC Condition
Column/dimensions: Chiralpak AD-H (30×250 mm), 5µ
% CO$_2$: 60.0%
% Co solvent: 40.0% (100% methanol)
Total Flow: 90.0 g/min
Back Pressure: 100.0 bar
UV: 234 nm
Stack time: 8.5 min
Load/Inj: 50.0 mg
Retention time: Peak 1—1.82 min, Peak 2—5.75 min.
Purity: Peak 1—99.68%, Peak 2—99.82%.
Solubility: Methanol+ACN
Instrument details: Make/Model: SFC-PIC SOLUTION Chiral Separation of Example 4

Example 4a (First Eluted Enantiomer)

$^1$H NMR (500 MHz, CDCl$_3$): δ 7.88 (d, J=8.0 Hz, 1H), 7.58 (d, J=7.5 Hz, 1H), 7.30 (s, 1H), 7.22 (s, 1H), 5.84-5.82 (m, 1H), 4.17 (s, 2H), 3.41-3.36 (m, 1H), 3.18-3.11 (m, 1H), 2.75-2.69 (m, 1H), 2.46-2.40 (m, 1H). LCMS (ES) m/z 462.14 [M+H]$^+$, HPLC: 99.69%. Chiral HPLC: 99.81%.

Example 4b (Second Eluted Enantiomer)

$^1$H NMR (500 MHz, CDCl$_3$): δ 7.88 (d, J=8.0 Hz, 1H), 7.58 (d, J=7.5 Hz, 1H), 7.30 (s, 1H), 7.22 (s, 1H), 5.83-5.81 (m, 1H), 4.15 (s, 2H), 3.40-3.35 (m, 1H), 3.17-3.11 (m, 1H), 2.73-2.70 (m, 1H), 2.44-2.39 (m, 1H); LCMS (ES) m/z 462.11 [M+H]$^+$, HPLC: 99.94%, Chiral HPLC: 99.82%

Example 5

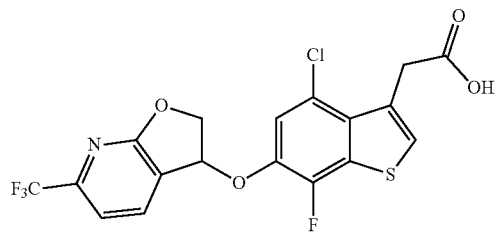 [SMILES: O=C(O)Cc1csc2c(F)c(OC3COc4nc(C(F)(F)F)ccc43)cc(Cl)c12]

Preparation of 2-(4-chloro-7-fluoro-6-((6-(trifluoromethyl)-2,3-dihydrofuro[2,3-b]pyridin-3-yl)oxy)benzo[b]thiophen-3-yl)acetic Acid a) Ethyl 2-(4-chloro-7-fluoro-6-((6-(trifluoromethyl)-2,3-dihydrofuro[2,3-b]pyridin-3-yl)oxy)benzo[b]thiophen-3-yl)acetate

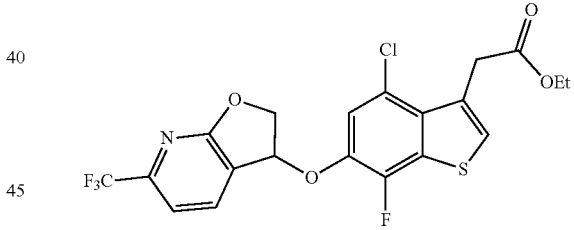

To a stirred solution of ethyl 2-(4-chloro-7-fluoro-6-hydroxybenzo[b]thiophen-3-yl)acetate (0.141 g, 0.487 mmol), 6-(trifluoromethyl)-2,3-dihydrofuro[2,3-b]pyridin-3-ol (0.100 g, 0.487 mmol) and ADDP (0.123 g, 0.487 mmol) in THF (10 mL) was added tri-n-butylphosphine (0.120 mL, 0.487 mmol) at RT. The reaction mixture was stirred at room temperature for 48 h, filtered through Celite® and evaporated under reduced pressure to afford crude product as yellow liquid, which was purified by flash column chromatography on 100-200 silica gel, using 30% EtOAc-Pet ether as an eluent to obtained ethyl 2-(4-chloro-7-fluoro-6-((6-(trifluoromethyl)-2,3-dihydrofuro[2,3-b]pyridin-3-yl)oxy)benzo[b]thiophen-3-yl)acetate (0.090 g, 37.5% yield) as pale yellow liquid. LCMS (ES) m/z 476.05 [M+H]$^+$.

b) 2-(4-Chloro-7-fluoro-6-((6-(trifluoromethyl)-2,3-dihydrofuro[2,3-b]pyridin-3-yl)oxy)benzo[b]thiophen-3-yl)acetic Acid

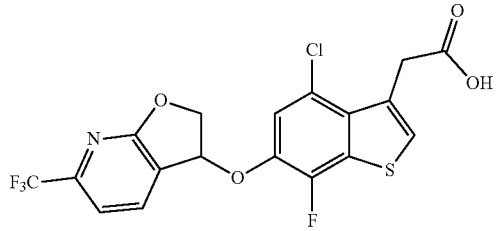 [SMILES: O=C(O)Cc1csc2c(F)c(OC3COc4nc(C(F)(F)F)ccc43)cc(Cl)c12]

The title compound was prepared as a white solid according to the procedures of examples XX as white solid. $^1$H NMR (400 MHz, DMSO-d$_6$): δ 8.09 (d, J=7.6 Hz, 1H), 7.60 (d, J=6.8 Hz, 1H), 7.51 (d, J=8.0 Hz, 1H), 7.46 (s, 1H), 6.31-6.30 (m, 1H), 4.94-4.83 (m, 2H), 3.77 (s, 2H). LCMS (ES) m/z 448.16 [M+H]$^+$. Chiral HPLC: 50.55%: 49.45%.

Analytical SFC Condition

Column/dimensions: Chiralcel OJ-H (4.6×250 mm), 5μ

% CO$_2$: 80.0%

% Co solvent: 20.0% (100% MeOH)

Total Flow: 4.0 g/min

Back Pressure: 100 bar

Temperature: 30° C.

UV: 214 nm

Preparative SFC Condition

Column/dimensions: Chiralcel OJ-H (21×250 mm), 5μ

% CO$_2$: 90.0%

% Co solvent: 10.0% (100% MeOH)

Total Flow: 60.0 g/min

Back Pressure: 100.0 bar

UV: 214 nm

Stack time: 4.3 min

Load/Inj: 2.5 mg

Retention time: Peak 1—2.93 min, Peak 2—4.89 min.

Purity: Peak 1—99.59%, Peak 2—99.30%.

Solubility: MeOH

Instrument details: Make/Model: SFC-80

Chiral Separation of Example 5

Example 5a (First Eluted Enantiomer)

$^1$H NMR (400 MHz, DMSO-d$_6$): δ 8.09 (d, J=7.6 Hz, 1H), 7.60 (d, J=6.8 Hz, 1H), 7.51 (d, J=8.0 Hz, 1H), 7.46 (s, 1H), 6.31-6.30 (m, 1H), 4.94-4.83 (m, 2H), 3.77 (s, 2H). LCMS (ES) m/z 447.82 [M+H]$^+$. Chiral HPLC: 99.59%.

Example 5b (Second Eluted Enantiomer)

$^1$H NMR (400 MHz, DMSO-d$_6$): δ 8.09 (d, J=7.6 Hz, 1H), 7.60 (d, J=6.8 Hz, 1H), 7.51 (d, J=8.0 Hz, 1H), 7.46 (s, 1H), 6.31-6.30 (m, 1H), 4.94-4.83 (m, 2H), 3.77 (s, 2H). LCMS (ES) m/z 448.26 [M+H]$^+$. Chiral HPLC: 99.30%.

Example 6

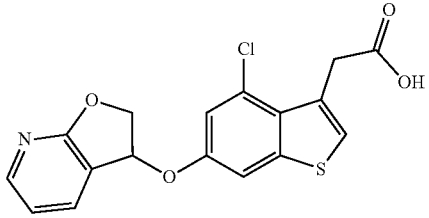 [SMILES: O=C(O)Cc1csc2cc(OC3COc4ncccc43)cc(Cl)c12]

Preparation of 2-(4-chloro-6-((2,3-dihydrofuro[2,3-b]pyridin-3-yl)oxy)benzo[b]thiophen-3-yl)acetic Acid a) Ethyl 2-(4-chloro-6-((2,3-dihydrofuro[2,3-b]pyridin-3-yl)oxy)benzo[b]thiophen-3-yl)acetate

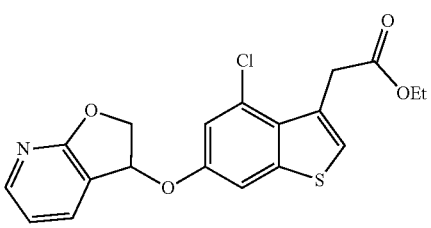 [SMILES: CCOC(=O)Cc1csc2cc(OC3COc4ncccc43)cc(Cl)c12]

The title compound was obtained in a same manner as the procedure in Example 5, Step a by using 2,3-dihydrofuro[2,3-b]pyridin-3-ol and 5-chloro-6,7-dihydro-5H-cyclopenta[b]pyridine, LCMS (ES) m/z 390.34 (M+H)$^+$.

b) 2-(4-Chloro-6-((2,3-dihydrofuro[2,3-b]pyridin-3-yl)oxy)benzo[b]thiophen-3-yl)acetic Acid

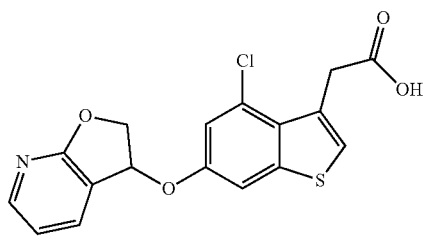 [SMILES: O=C(O)Cc1csc2cc(OC3COc4ncccc43)cc(Cl)c12]

To a solution of ethyl 2-(4-chloro-6-((2,3-dihydrofuro[2,3-b]pyridin-3-yl)oxy)benzo[b]thiophen-3-yl)acetate (1.7 g, 4.36 mmol) in Methanol (16 mL), THF (8 mL) and Water (16 mL) was added LiOH (0.522 g, 21.80 mmol) at rt and stirred for 2 h at same temperature. Reaction mixture was acidified with citric acid solution (nearly pH=6-7), filtered the solid precipitated and dried under vacuum to get 2-(4-chloro-6-((2,3-dihydrofuro[2,3-b]pyridin-3-yl)oxy)benzo[b]thiophen-3-yl)acetic acid (1 g, 2.73 mmol, 62.7% yield) as an white solid. $^1$H NMR (400 MHz, DMSO-d$_6$): δ 12.39 (brs, 1H), 8.19 (dd, J=2.0, 5.2 Hz, 1H), 7.92 (dd, J=1.6, 7.2 Hz, 1H), 7.79 (d, J=2.4 Hz, 1H), 7.51 (s, 1H), 7.15 (d, J=2.8 Hz, 1H), 7.00 (dd, J=4.8, 7.4 Hz, 1H), 6.23-6.21 (m, 1H), 4.85-4.81 (m, 1H), 4.62-4.59 (m, 1H), 4.01 (s, 2H). ESI-MS m/z 362.13 [M+H]⁺. Chiral HPLC: 48.09%: 50.68%.

Analytical SFC Condition

Column/dimensions: Chiralpak AS-H (4.6×250 mm), 5μ
% $CO_2$: 65.0%
% Co solvent: 35.0% (100% methanol)
Total Flow: 3.0 g/min
Back Pressure: 100 bar
Temperature: 30° C.
UV: 235 nm Preparative SFC Condition Column/dimensions: Chiralpak AS-H (30×250 mm), 5μ
% $CO_2$: 65.0%
% Co solvent: 35.0% (100% methanol)
Total Flow: 100.0 g/min
Back Pressure: 100.0 bar
UV: 235 nm
Stack time: 6.5 min
Load/Inj: 18.0 mg
Retention time: Peak 1—3.41 min, Peak 2—4.92 min.
Purity: Peak 1—99.82%, Peak 2—99.50%.
Solubility: Methanol+ACN
Instrument details: Make/Model: SFC-200-004 (PIC-Solution)

Chiral Separation of Example 6

Example 6a (First Eluted Enantiomer)

¹H NMR (400 MHz, DMSO-$d_6$): δ 12.39 (brs, 1H), 8.19 (dd, J=2.0, 5.2 Hz, 1H), 7.92 (dd, J=1.6, 7.2 Hz, 1H), 7.79 (d, J=2.4 Hz, 1H), 7.51 (s, 1H), 7.15 (d, J=2.8 Hz, 1H), 7.00 (dd, J=4.8, 7.4 Hz, 1H), 6.23-6.21 (m, 1H), 4.87-4.80 (m, 1H), 4.64-4.57 (m, 1H), 4.01 (s, 2H). LCMS (ES) m/z 362.13 [M+H]⁺. Chiral HPLC purity: 99.80%.

Example 6b (Second Eluted Enantiomer)

¹H NMR (400 MHz, DMSO-$d_6$): δ 12.39 (brs, 1H), 8.19 (dd, J=2.0, 5.2 Hz, 1H), 7.92 (dd, J=1.6, 7.2 Hz, 1H), 7.79 (d, J=2.4 Hz, 1H), 7.51 (s, 1H), 7.15 (d, J=2.8 Hz, 1H), 7.00 (dd, J=4.8, 7.4 Hz, 1H), 6.23-6.21 (m, 1H), 4.87-4.80 (m, 1H), 4.64-4.57 (m, 1H), 4.01 (s, 2H). LCMS (ES) m/z 362.13 [M+H]⁺. Chiral HPLC purity: 99.50%.

Example 7

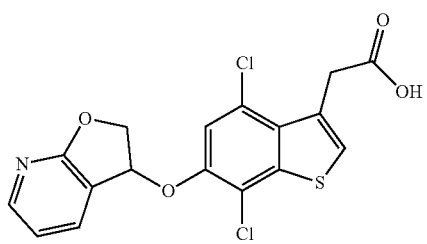 [SMILES: O=C(O)Cc1csc2c(Cl)c(OC3COc4ncccc43)cc(Cl)c12]

Preparation of 2-(4,7-dichloro-6-((2,3-dihydrofuro[2,3-]pyridin-3-yl)oxy)benzo[b]thiophen-3-yl)acetic Acid a) Ethyl 2-(4,7-dichloro-6-((2,3-dihydrofuro[2,3-b]pyridin-3-yl)oxy)benzo[b]thiophen-3-yl)acetate

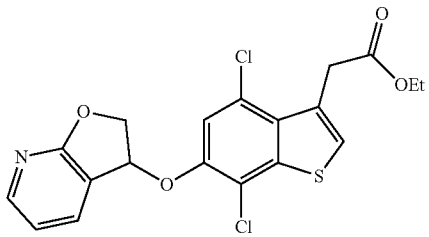 [SMILES: CCOC(=O)Cc1csc2c(Cl)c(OC3COc4ncccc43)cc(Cl)c12]

To a stirred solution of ADDP (827 mg, 3.28 mmol) in dry THF (2 mL), tri-n-butylphosphine (1.079 mL, 4.38 mmol) was slowly added at ambient temperature. After decolorisation was observed, 2,3-dihydrofuro[2,3-b]pyridin-3-ol (300 mg, 2.188 mmol) was added and stirred for 5 min. Finally ethyl 2-(4,7-dichloro-6-hydroxybenzo[b]thiophen-3-yl)acetate (668 mg, 2.188 mmol) was added. The reaction mass was stirred at the same temperature for 24 h. After TLC analysis the reaction mixture was diluted with water and extracted with EtOAc. The organic layer was washed with water, brine, dried over $Na_2SO_4$ and concentrated under reduced pressure to afford crude. The crude was purified by silica gel chromatography using 30% EtOAc/pet ether as an eluent to afford ethyl 2-(4,7-dichloro-6-((2,3-dihydrofuro[2,3-b]pyridin-3-yl)oxy)benzo[b]thiophen-3-yl)acetate (120 mg) as a colorless gummy liquid. LCMS (ES) m/z 424.14 [M+H]⁺ b) 2-(4,7-Dichloro-6-((2,3-dihydrofuro[2,3-b]pyridin-3-yl)oxy)benzo[b]thiophen-3-yl)acetic Acid

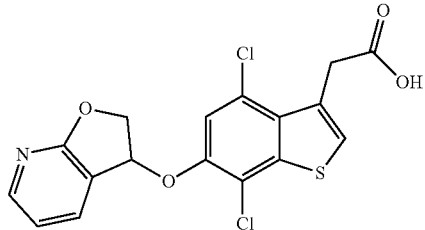 [SMILES: O=C(O)Cc1csc2c(Cl)c(OC3COc4ncccc43)cc(Cl)c12]

To a stirred solution of ethyl 2-(4,7-dichloro-6-((2,3-dihydrofuro[2,3-b]pyridin-3-yl)oxy)benzo[b]thiophen-3-yl)acetate (120 mg, 0.283 mmol) in methanol (1 mL), THF (1 mL) and water (1.000 mL), lithium hydroxide (20.32 mg, 0.848 mmol) was added at ambient temperature and stirred for 4 h. After TLC analysis the reaction mixture was evaporated to remove solvents and the crude was cooled to 0° C. and acidified with saturated citric acid solution (p$^H$~5). Obtained solids were filtered and dried well to afford 2-(4,7-dichloro-6-((2,3-dihydrofuro[2,3-b]pyridin-3-yl)oxy)benzo[b]thiophen-3-yl)acetic acid (72 mg, 63.7% yield) as an off-white solid. ¹H NMR (400 MHz, DMSO-$d_6$) δ 8.21-8.20 (m, 1H), 7.85-7.84 (m, 1H), 7.63 (s, 1H), 7.54 (s, 1H), 7.02-6.99 (m, 1H), 6.31 (d, J=4.5 Hz, 1H), 4.83-4.74

(m, 1H), 4.67-4.64 (m, 1H), 3.92 (s, 2H). LCMS (ES) m/z 396.25 [M+H]⁺. Chiral HPLC: 48.99%: 49.56%.

Analytical SFC Condition

Column/dimensions: Chiralpak AD-H (4.6×250 mm), 5μ

% CO$_2$: 60.0%

% Co solvent: 40.0% (100% MeOH)

Total Flow: 4.0 g/min

Back Pressure: 100 bar

Temperature: 30° C.

UV: 214 nm

Preparative SFC Condition

Column/dimensions: Chiralpak AD-H (30×250 mm), 5μ

% CO$_2$: 60.0%

% Co solvent: 40.0% (100% MeOH)

Total Flow: 90.0 g/min

Back Pressure: 90.0 bar

UV: 214 nm

Stack time: 8.0 min

Load/Inj: 25.0 mg

Retention time: Peak 1-2.73 min, Peak 2—5.34 min.

Purity: Peak 1-99.81%, Peak 2—98.63%

Solubility: MeOH+Acetonitrile

Chiral Separation of Example 7

Example 7a (First Eluted Enantiomer)

$^1$H NMR (400 MHz, DMSO-d$_6$) δ 12.89 (brs, 1H), 8.21-8.20 (m, 1H), 7.85-7.84 (m, 1H), 7.63 (s, 1H), 7.54 (s, 1H), 7.02-6.99 (m, 1H), 6.31 (d, J=4.5 Hz, 1H), 4.83-4.74 (m, 1H), 4.67-4.64 (m, 1H), 3.92 (s, 2H). LCMS (ES) m/z 396.15 [M+H]⁺. Chiral purity: 99.81%.

Example 7b (Second Eluted Enantiomer)

$^1$H NMR (400 MHz, DMSO-d$_6$) δ 12.89 (brs, 1H), 8.21-8.20 (m, 1H), 7.85-7.84 (m, 1H), 7.63 (s, 1H), 7.54 (s, 1H), 7.02-6.99 (m, 1H), 6.31 (d, J=4.5 Hz, 1H), 4.83-4.74 (m, 1H), 4.67-4.64 (m, 1H), 3.92 (s, 2H). LCMS (ES) m/z 396.25 [M+H]⁺. Chiral purity: 98.63%

Examples 8 and 9

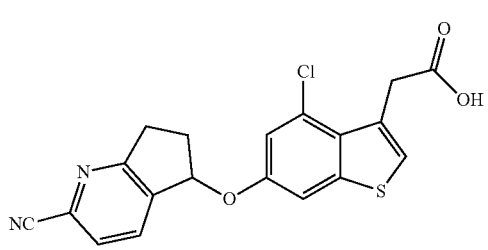 [SMILES: N#Cc1ccc2c(n1)CCC2Oc1cc(Cl)c2c(CC(=O)O)csc2c1]

Preparation of 2-(4-chloro-6-((2-cyano-6,7-dihydro-5H-cyclopenta[b]pyridin-5-yl)oxy)benzo[b]thiophen-3-yl)acetic Acid (Example 8)

a) Ethyl 2-(4-chloro-6-((2-chloro-6,7-dihydro-5H-cyclopenta[b]pyridin-5-yl)oxy)benzo[b]thiophen-3-yl)acetate

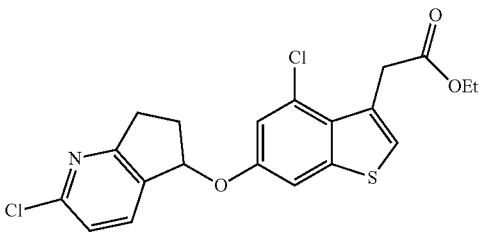 [SMILES: CCOC(=O)Cc1csc2cc(OC3CCc4nc(Cl)ccc43)cc(Cl)c12]

2,5-Dichloro-6,7-dihydro-5H-cyclopenta[b]pyridine (556 mg, 2.95 mmol) was added to the stirred solution of K$_2$CO$_3$ (1225 mg, 8.86 mmol) and ethyl 2-(4-chloro-6-hydroxy-benzo[b]thiophen-3-yl)acetate (800 mg, 2.95 mmol) in DMF (20 mL) at 0° C. and the mixture was stirred at 60° C. for 2 h. The reaction mixture was diluted with water and mixture was concentrated under reduced pressure. The resulted residue was partitioned between EtOAc and water, the separated organic layer was washed with brine solution, dried over anhydrous Na$_2$SO$_4$, filtered and filtrate was evaporated under reduced pressure. The resulted crude compound was purified by flash column chromatography (100-200 silica mesh, eluent was 20% EtOAc in pet ether) to obtained ethyl 2-(4-chloro-6-((2-chloro-6,7-dihydro-5H-cyclopenta[b]pyridin-5-yl)oxy)benzo[b]thiophen-3-yl)acetate (600 mg, 43.0% yield) as a colorless liquid. LCMS (ES) m/z 422.10 [M+H]⁺.

b) Ethyl 2-(4-chloro-6-((2-cyano-6,7-dihydro-5H-cyclopenta[b]pyridin-5-yl)oxy)benzo[b]thiophen-3-yl)acetate

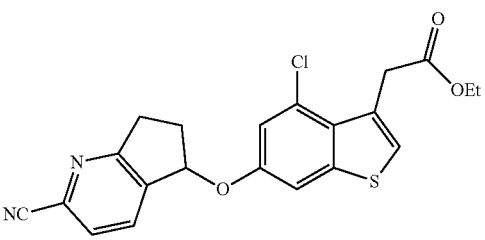 [SMILES: CCOC(=O)Cc1csc2cc(OC3CCc4nc(C#N)ccc43)cc(Cl)c12]

Tetrakis (164 mg, 0.142 mmol) was added to a degassed solution of ethyl 2-(4-chloro-6-((2-chloro-6,7-dihydro-5H-cyclopenta[b]pyridin-5-yl)oxy)benzo[b]thiophen-3-yl)acetate (600 mg, 1.421 mmol) and dicyanozinc (167 mg, 1.421 mmol) in DMF (10 mL). The mixture was further degassed for 10 min and heated to 120° C. for 1 h under microwave condition. The reaction mixture was filtered through a pad of Celite® and filtrate was partitioned between EtOAc and water. The separated organic layer was washed with brine solution, dried over anhydrous Na$_2$SO$_4$, filtered and filtrate was evaporated under reduced pressure to get the crude. The crude was purified by silica gel column chromatography by using EtOAc in hexane as eluent. The product was eluted at 40% EtOAc-Pet ether to get ethyl 2-(4-chloro-6-((2-cyano-6,7-dihydro-5H-cyclopenta[b]pyridin-5-yl)oxy)benzo[b]thiophen-3-yl)acetate (380 mg, 64.4% yield) as an off-white solids. $^1$H NMR (500 MHz, DMSO-d$_6$): δ 8.06 (d, J=8.0 Hz, 1H), 7.91 (d, J=8.0 Hz, 1H), 7.82 (d, J=2.0 Hz, 1H), 7.53 (s, 1H), 7.17 (d, J=2.0 Hz, 1H), 6.10-6.07 (m, 1H), 4.13 (q, J=7.0 Hz 2H), 4.01 (s, 2H), 3.20-3.13 (m, 1H), 3.07-3.03 (m, 1H), 2.77-2.72 (m, 1H), 2.16-2.12 (m, 1H), 1.20 (t, J=7.5 Hz, 3H). LCMS (ES) m/z 413.25 [M+H]$^+$.

c) 2-(4-Chloro-6-((2-cyano-6,7-dihydro-5H-cyclopenta[b]pyridin-5-yl)oxy)benzo[b]thiophen-3-yl) acetic Acid

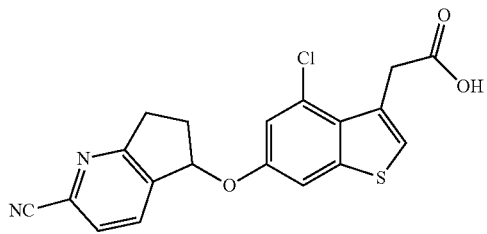 [SMILES: N#Cc1ccc2c(n1)CCC2Oc1cc(Cl)c2c(CC(=O)O)csc2c1]

3N HCl (10 mL, 30.0 mmol) was added to a stirred solution of ethyl 2-(4-chloro-6-((2-cyano-6,7-dihydro-5H-cyclopenta[b]pyridin-5-yl)oxy)benzo[b]thiophen-3-yl)acetate (0.35 g, 0.848 mmol) in THF (50 mL) at 0° C. The reaction mixture was stirred and heated to 70° C. for 8 h. Evaporated the excess of solvents under reduced pressure and water was added to the reaction mixture. The precipitated solid was filtered and dried under vacuum to get crude material. The resulted crude compound was purified by flash column chromatography (100-200 silica mesh, eluent was 3% MeOH-DCM to obtained 2-(4-chloro-6-((2-cyano-6,7-dihydro-5H-cyclopenta[b]pyridin-5-yl)oxy)benzo[b]thiophen-3-yl)acetic acid (0.2000 g, 58.8% yield) as an off-white solid. $^1$H NMR (400 MHz, DMSO-d$_6$): δ 12.36 (brs, 1H), 8.06 (d, J=7.6 Hz, 1H), 7.91 (d, J=7.6 Hz, 1H), 7.81 (d, J=2.0 Hz, 1H), 7.50 (s, 1H), 7.17 (d, J=2.0 Hz, 1H), 6.10-6.07 (m, 1H), 4.01 (s, 2H), 3.20-3.13 (m, 1H), 3.07-3.03 (m, 1H), 2.77-2.72 (m, 1H), 2.16-2.12 (m, 1H). LCMS (ES) m/z 385.10 [M+H]$^+$.

d) 2-(6-((2-carbamoyl-6,7-dihydro-5H-cyclopenta[b]pyridin-5-yl)oxy)-4-chlorobenzo[b]thiophen-3-yl) acetic Acid: (Example 9)

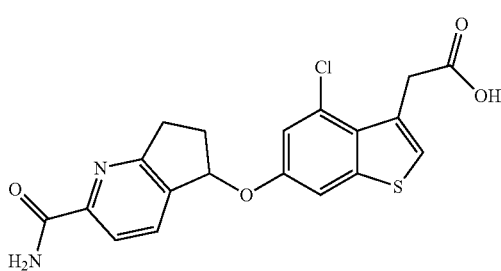 [SMILES: NC(=O)c1ccc2c(n1)CCC2Oc1cc(Cl)c2c(CC(=O)O)csc2c1]

H$_2$O$_2$ (0.064 mL, 2.079 mmol) was added to a stirred solution of 2-(4-chloro-6-((2-cyano-6,7-dihydro-5H-cyclopenta[b]pyridin-5-yl)oxy)benzo[b]thiophen-3-yl)acetic acid (400 mg, 1.039 mmol) in KOH (117 mg, 2.079 mmol) and ethanol (50 mL) at 0° C. The reaction mixture was stirred at RT for 1 h. The reaction mixture was concentrated under reduced pressure to get crude. Water (10 mL) was added and adjusted acidic pH by using 2N citric acid solution and then filtered the precipitated solid. The solid was washed with n-pentane to get 2-(6-((2-carbamoyl-6,7-dihydro-5H-cyclopenta[b]pyridin-5-yl)oxy)-4-chlorobenzo[b]thiophen-3-yl) acetic acid (200 mg, 47.7% yield) as an off-white solid. $^1$H NMR (500 MHz, DMSO-d$_6$): δ 12.35 (brs, 1H), 8.06 (s, 1H), 7.97 (d, J=8.0 Hz, 1H), 7.92 (d, J=8.0 Hz, 1H), 7.81 (d, J=2.0 Hz, 1H), 7.64 (s, 1H), 7.49 (s, 1H), 7.16 (d, J=2.0 Hz, 1H), 6.08-6.06 (m, 1H), 4.01 (s, 2H), 3.20-3.14 (m, 1H), 3.05-3.00 (m, 1H), 2.76-2.72 (m, 1H), 2.17-2.13 (m, 1H). LCMS (ES) m/z 402.82 [M+H]$^+$. Chiral HPLC: 49.44%: 50.55%.

Analytical SFC Condition
Column/dimensions: Chiralpak-IG (4.6×250 mm), 5µ
% CO$_2$: 50.0%
% Co solvent: 50.0% (100% MeOH)
Total Flow: 4.0 g/min
Back Pressure: 100 bar
Temperature: 30° C.
UV: 214 nm
Preparative SFC Condition
Column/dimensions: Chiralpak-IG (30×250 mm), 5µ
% CO$_2$: 50.0%
% Co solvent: 50.0% (100% MeOH)
Total Flow: 90.0 g/min
Back Pressure: 90.0 bar
UV: 214 nm
Stack time: 15.5 min
Load/Inj: 15.0 mg
Retention time: Peak 1-11.41 min, Peak 2—14.44 min.
Purity: Peak 1-99.61%, Peak 2—99.07%.
Solubility: Few drops of H$_2$O+THF+MeOH
Instrument details: Make/Model: SFC-200-003

Chiral Separation of Examples 9

Examples 9a (First Eluted Enantiomer)

$^1$H NMR (500 MHz, DMSO-d$_6$): δ 12.35 (brs, 1H), 8.06 (s, 1H), 7.97 (d, J=8.0 Hz, 1H), 7.92 (d, J=8.0 Hz, 1H), 7.81 (d, J=2.0 Hz, 1H), 7.64 (s, 1H), 7.49 (s, 1H), 7.16 (d, J=2.0 Hz, 1H), 6.08-6.06 (m, 1H), 4.01 (s, 2H), 3.20-3.14 (m, 1H), 3.05-3.00 (m, 1H), 2.76-2.72 (m, 1H), 2.17-2.13 (m, 1H). LCMS (ES) m/z 403.22 [M+H]$^+$. Chiral HPLC: 99.61%.

Examples 9b (Second Eluted Enantiomer)

$^1$H NMR (500 MHz, DMSO-d$_6$): δ 12.35 (brs, 1H), 8.06 (s, 1H), 7.97 (d, J=8.0 Hz, 1H), 7.92 (d, J=8.0 Hz, 1H), 7.81 (d, J=2.0 Hz, 1H), 7.64 (s, 1H), 7.49 (s, 1H), 7.16 (d, J=2.0 Hz, 1H), 6.08-6.06 (m, 1H), 4.01 (s, 2H), 3.20-3.14 (m, 1H), 3.05-3.00 (m, 1H), 2.76-2.72 (m, 1H), 2.17-2.13 (m, 1H). LCMS (ES) m/z 403.28 [M+H]$^+$. Chiral HPLC: 99.07%

Assay Protocol

Compounds contained herein were evaluated for their ability to inhibit the activity of GOAT. GOAT activity was assessed using a time-resolved fluorescence energy transfer (TR-FRET) assay in a 384-well format. His-tag human GOAT enzyme was in the form of a cell membrane preparation from sf9 cells infected with hGOAT-V5-His baculovirus. Varying concentrations of test compound with final DMSO concentration kept to 0.5% were added to membrane solution. Human GOAT membrane activity was established in a buffer having final concentration 0.25 mg/mL in 50 mM MOPS, pH7.5; 50 mM KCl; 0.1 mg/mL BSA; 50 μM CHAPS; and 2 mM EDTA. Substrate solution consisting of biotinylated ghrelin peptide (final concentration 100 nM), octanoyl coA (final concentration 2 μM) and palmitoyl CoA (final concentration 50 μM) was added to initiate the reaction. Plates were sealed, centrifuged for 1 minute at 2000 rpm, then incubated at 30° C. for 80 minutes with gentle shaking on an Eppendorf mix plate. Reaction termination and detection mix consisting of chicken anti-active ghrelin antibody (final concentration of 10 nM), Europium W1024-labeled streptavidin (final concentration of 4 nM), GOAT anti-chicken Dylight (final concentration of 12.5 nM), and GS[DAP-oc]-FL-amide inhibitor (final concentration of 1 μM) was added before further incubation for 40 minutes at 30° C. The plate was then read on an Envision in HTRF mode with excitation filter UV (TRF) 340 and first emission filter of APC 665 and a second emission filter of Europium 615. HTRF readings were acquired as per instrument defined LANCE-DELFIA protocol with a delay and window times of 50 μs for both; number of sequential windows: 1; time between flashes: 2000 μs between each of 100 flashes and 10 flashes for the second detector. The HTRF ratio was calculated directly by the instrument as the ratio of 665 window/615 window. Percent inhibition was calculated as $100-(100\times(U-NC)/(PC-NC))$ where U was the unknown value HTRF ratio (test compound value), NC was the negative control (100% inhibition value generated from a potent inhibitor), and PC was the positive control (100% activity generated from 0.5% DMSO vehicle). $IC_{50}$ values were generated in GraphPad Prism (Version 4.03) using non-linear regression curve fit and sigmoidal dose response variable slope analysis.

Results

The exemplified compounds were generally tested according to the above or an analogous assay and were found to be inhibitors of GOAT. Specific biological activities tested according to such assays are listed in the following table as follows ($IC_{50}$): A<50 nM, B: <500 nM, C: <5000 nM. As variability in such assays is inevitable, repeating the assay run(s) may result in slightly different $IC_{50}$ values.

| Example | hGOAT $IC_{50}$ (nM) |
| --- | --- |
| 1a | A |
| 1b | C |
| 2a | A |
| 2b | C |
| 3a | B |
| 3b | A |
| 4a | B |
| 4b | A |
| 5a | C |
| 5b | A |
| 6a | A |
| 6b | A |
| 7a | C |
| 7b | A |
| 8 | A |
| 9a | B |
| 9b | A |

Evaluation in Animal Models

The activity of Example 1a was evaluated in vivo in three preclinical species by assessing the level of reduction of acyl ghrelin in circulation after treatment.

Acyl Ghrelin Reduction in Mice

Figure 3:
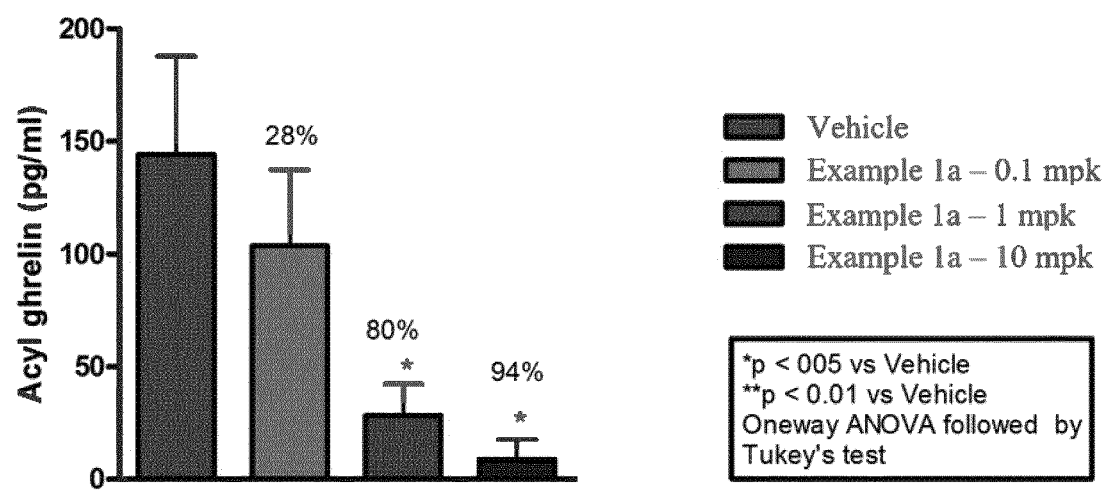
FIG. 3 shows the dose response of Example 1a on fasting induced acyl ghrelin levels.

Normal mice were administered various oral doses of Example 1a on a bid basis for two days (4 doses). Food was withdrawn the evening of the second day after the fourth dose, and then the animals were administered a final dose the morning of the third day. Three hours after this fifth and final dose, blood was collected for ghrelin and acyl ghrelin measurement by ELISA. Dose-dependent decreases in acyl ghrelin and increases in des-acyl ghrelin were observed. As seen in FIG. 3, acyl ghrelin reductions were statistically significant ($p<0.05$) at both 1 and 10 mg/kg Example 1a.

Acyl Ghrelin Reduction in Rats

Figure 4:
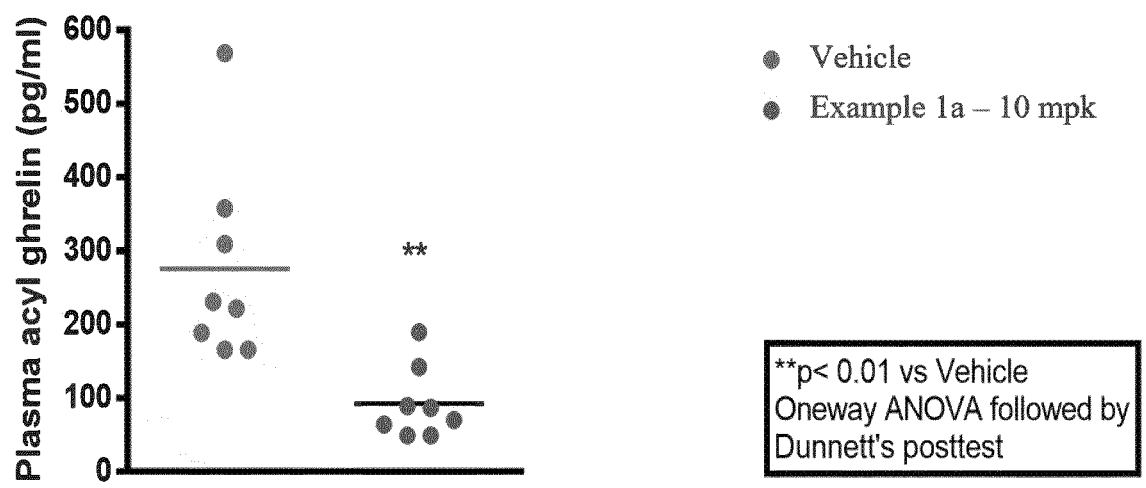
FIG. 4 shows the effect of Example 1a on fasting-induced acyl ghrelin levels in male SD rats.
Figure 5:
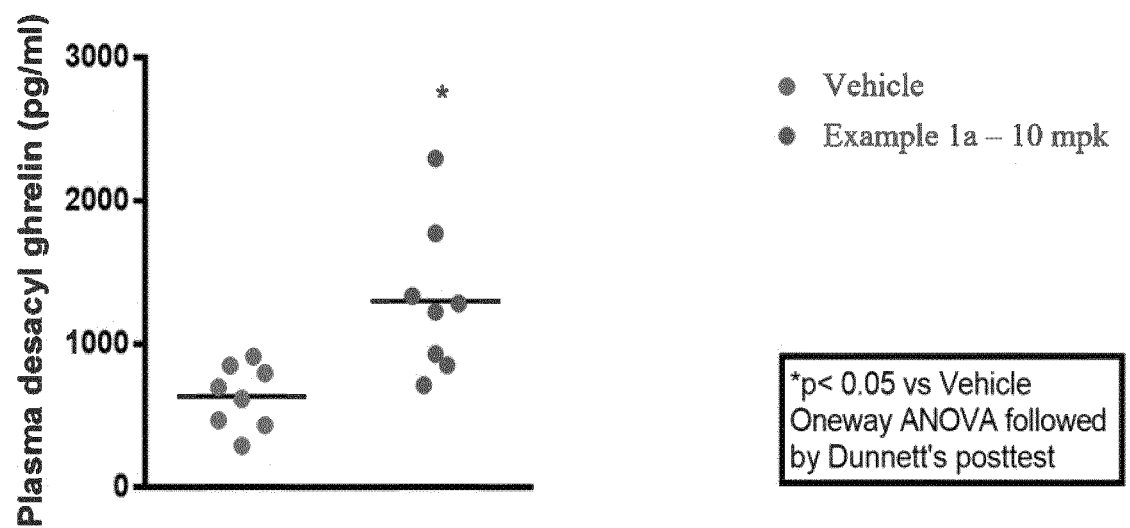
FIG. 5 shows the effect of Example 1a on fasting-induced des-acyl ghrelin levels in male SD rats.

The same experimental design was conducted in rats administered 10 mg/kg of Example 1a. The GOAT inhibitor significantly reduced acyl ghrelin levels (FIG. 4) and increased des-acyl ghrelin levels (FIG. 5) in rats.

Acyl Ghrelin Reduction in Cynomolgus Monkeys

Figure 6:
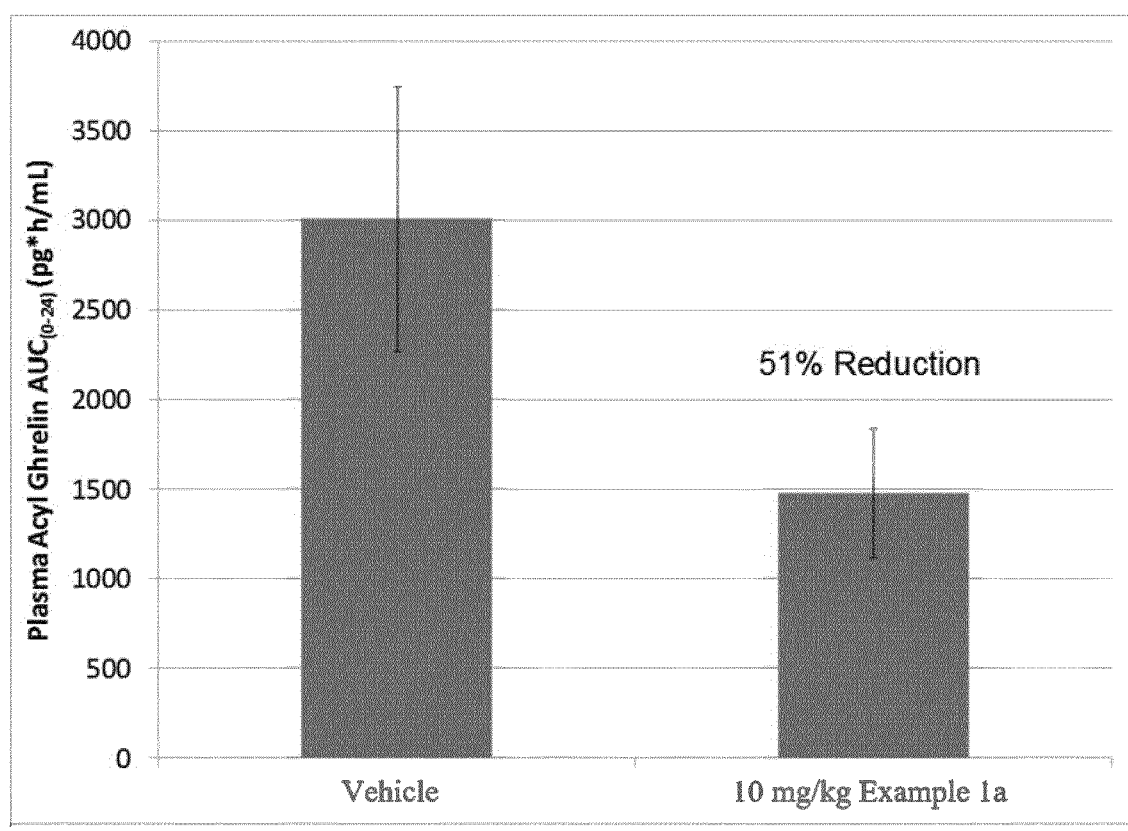
FIG. 6 shows acyl ghrelin reduction after a single 10 mg/kg dose in Cynomolgus monkeys.

A single-dose PK/PD study was conducted in cynomolgus monkeys after a 10 mg/kg dose of Example 1a. On day zero, after an overnight fast, three monkeys were administered an oral dose of vehicle, and blood was collected pre-dose and 1, 3, 8, and 24 hours later. The 24 hour time point served as the pre-dose measurement for day 1 when, after an overnight fast, the monkeys were administered a single oral dose of 10 mg/kg Example 1a. Blood was collected at various time points (15 minutes, 30 minutes, 1 hour, 3 hours, 8 hours, 24 hours, 48 hours, 96 hours, and 168 hours) with overnight fasting throughout the study. Levels of acyl ghrelin were measured using a Millipore metabolic panel that did not include des-acyl ghrelin. Over the first 24 hours, treatment with Example 1a caused a 51% reduction in the acyl ghrelin AUC relative to vehicle treatment (FIG. 6).

Acyl Ghrelin Reduction in Mice on a High Fat, High Carb Diet

Normal mice were acclimated to individual housing for two weeks on normal chow diet (20% calories from protein, 35% from carbohydrate, and 45% from fat). All mice except a control group were then switched to a high fat, high carb (HFHC) diet to cause obesity. Mice on the HFHC diet were administered 3 mg/kg Rimonabant once daily for seven days to cause weight loss except for one group that initiated 10 mg/kg Example 1a immediately. Mice that had been treated with Rimonabant were then administered various treatments in the evening for 21 days: vehicle, 3 mg/kg Rimonabant, or 10 mg/kg Example 1a. Mice were fasted overnight and administered a final treatment in the morning. Three hours later, blood was collected for plasma acyl ghrelin and des-acyl ghrelin determination.

Figure 7:
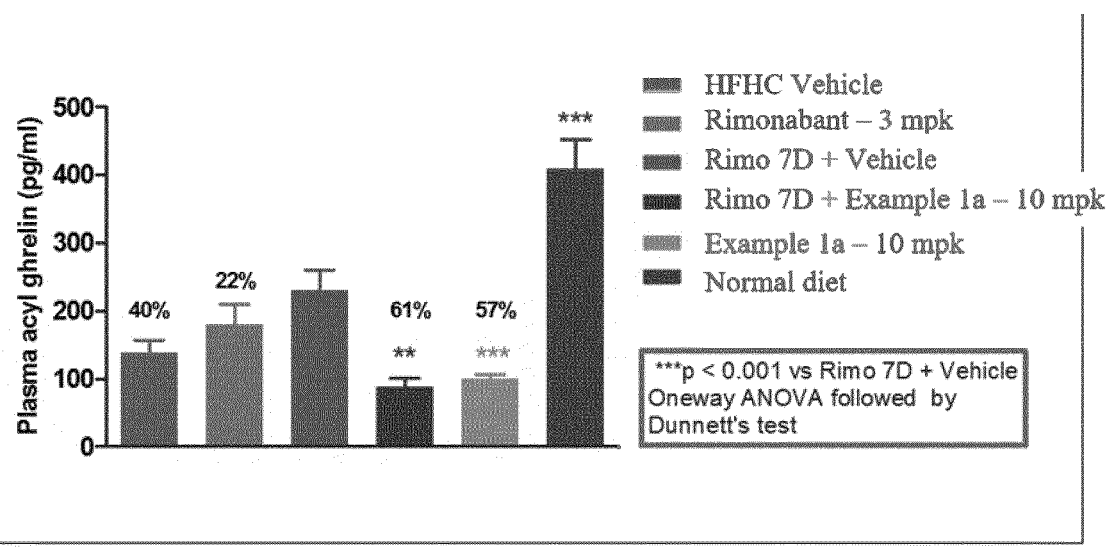
FIG. 7 shows the effect of Example 1a and Rimonabant on plasma acyl ghrelin levels in high fat high carbohydrate fed male C57BL/6 mice.
Figure 8:
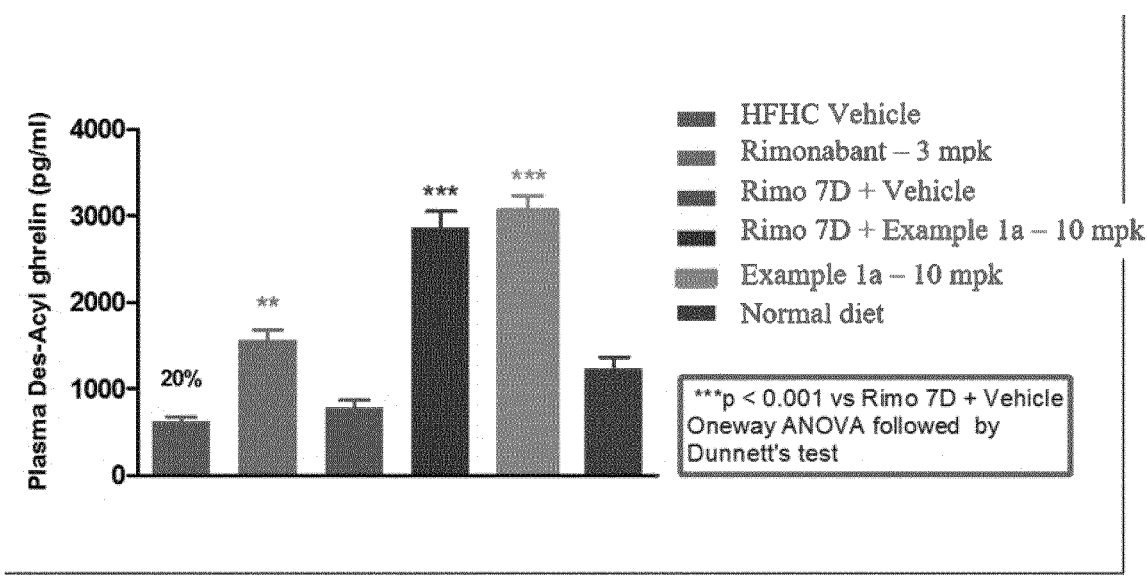
FIG. 8 shows the effect of Example 1a and Rimonabant on plasma des-acyl ghrelin levels in high fat high carbohydrate fed male C57BL/6 mice.

As seen in FIG. 7, by the end of the study, mice fed the HFHC diet, regardless of other treatment, had lower acyl ghrelin levels than mice fed normal chow. Continuous treatment with Example 1a and treatment with Example 1a after Rimonabant produced statistically significant 57% and 61% reductions in acyl ghrelin levels compared to Rimonabant followed by vehicle. Continuous treatment of Example 1a produced a 28% reduction in acyl ghrelin compared to vehicle treatment alone. As seen in FIG. 8, des-acyl ghrelin levels were statistically significantly elevated by both Example 1a treatments relative to the Rimonabant followed by vehicle treatment. Rimonabant treatment alone also led to increased acyl ghrelin levels, but not as much as that seen for treatment with Example 1a with or without Rimonabant pretreatment.

What is claimed is:

1. A compound according to Formula (I) or a pharmaceutically acceptable salt thereof:

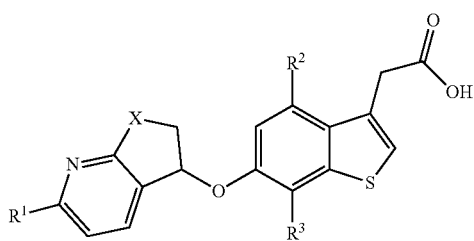

wherein:
$R^1$ is hydrogen, halogen, cyano, $(C_1$-$C_4)$alkyl, halo($C_1$-$C_4$)alkyl, or C(=O)NH$_2$;
X is CH$_2$ or O;
$R^2$ is halogen; and
$R^3$ is hydrogen or halogen.

2. The compound or pharmaceutically acceptable salt thereof according to claim 1, represented by Formula (II):

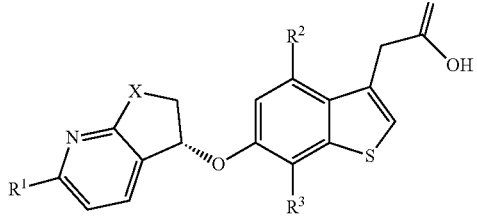

wherein:
$R^1$ is hydrogen, halogen, cyano, $(C_1$-$C_4)$alkyl, halo($C_1$-$C_4$)alkyl, or C(=O)NH$_2$;
X is CH$_2$ or O;
$R^2$ is halogen; and
$R^3$ is hydrogen or halogen.

3. The compound or pharmaceutically acceptable salt thereof according to claim 1, represented by Formula (III):

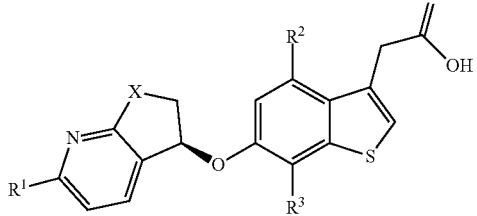

wherein:
$R^1$ is hydrogen, halogen, cyano, $(C_1$-$C_4)$alkyl, halo($C_1$-$C_4$)alkyl, or —C(=O)NH$_2$;
X is CH$_2$ or O;
$R^2$ is halogen; and
$R^3$ is hydrogen or halogen.

4. The compound or pharmaceutically acceptable salt thereof according to claim 1, wherein $R^1$ is hydrogen, chloro, cyano, methyl, —CF$_3$, or —C(=O)NH$_2$.

5. The compound or pharmaceutically acceptable salt thereof according to claim 1, wherein $R^1$ is hydrogen.

6. The compound or pharmaceutically acceptable salt thereof according to claim 1, wherein X is CH$_2$.

7. The compound or pharmaceutically acceptable salt thereof according to claim 1, wherein X is O.

8. The compound or pharmaceutically acceptable salt thereof according to claim 1, wherein $R_2$ is chloro.

9. The compound or pharmaceutically acceptable salt thereof according to claim 1, wherein $R_3$ is hydrogen, chloro, or fluoro.

10. The compound or pharmaceutically acceptable salt thereof according to claim 1, wherein $R_3$ is hydrogen.

11. The compound according to claim 1 which is:
2-(4-chloro-6-((6,7-dihydro-5H-cyclopenta[b]pyridin-5-yl)oxy)benzo[b]thiophen-3-yl)acetic acid;
(R)-2-(4-chloro-6-((6,7-dihydro-5H-cyclopenta[b]pyridin-5-yl)oxy)benzo[b]thiophen-3-yl)acetic acid;
(S)-2-(4-chloro-6-((6,7-dihydro-5H-cyclopenta[b]pyridin-5-yl)oxy)benzo[b]thiophen-3-yl)acetic acid;
2-(4-chloro-6-((2-methyl-6,7-dihydro-5H-cyclopenta[b]pyridin-5-yl)oxy)benzo[b]thiophen-3-yl)acetic acid;
(R)-2-(4-chloro-6-((2-methyl-6,7-dihydro-5H-cyclopenta[b]pyridin-5-yl)oxy)benzo[b]thiophen-3-yl)acetic acid;
(S)-2-(4-chloro-6-((2-methyl-6,7-dihydro-5H-cyclopenta[b]pyridin-5-yl)oxy)benzo[b]thiophen-3-yl)acetic acid;
2-(4,7-dichloro-6-((2-chloro-6,7-dihydro-5H-cyclopenta[b]pyridin-5-yl)oxy)benzo[b]thiophen-3-yl)acetic acid;
(R)-2-(4,7-dichloro-6-((2-chloro-6,7-dihydro-5H-cyclopenta[b]pyridin-5-yl)oxy)benzo[b]thiophen-3-yl)acetic acid;
(S)-2-(4,7-dichloro-6-((2-chloro-6,7-dihydro-5H-cyclopenta[b]pyridin-5-yl)oxy)benzo[b]thiophen-3-yl)acetic acid;
2-(4,7-dichloro-6-((2-(trifluoromethyl)-6,7-dihydro-5H-cyclopenta[b]pyridin-5-yl)oxy)benzo[b]thiophen-3-yl)acetic acid;
(R)-2-(4,7-dichloro-6-((2-(trifluoromethyl)-6,7-dihydro-5H-cyclopenta[b]pyridin-5-yl)oxy)benzo[b]thiophen-3-yl)acetic acid;
(S)-2-(4,7-dichloro-6-((2-(trifluoromethyl)-6,7-dihydro-5H-cyclopenta[b]pyridin-5-yl)oxy)benzo[b]thiophen-3-yl)acetic acid;
2-(4-chloro-7-fluoro-6-((6-(trifluoromethyl)-2,3-dihydrofuro[2,3-b]pyridin-3-yl)oxy)benzo[b]thiophen-3-yl)acetic acid;
(R)-2-(4-chloro-7-fluoro-6-((6-(trifluoromethyl)-2,3-dihydrofuro[2,3-b]pyridin-3-yl)oxy)benzo[b]thiophen-3-yl)acetic acid;
(S)-2-(4-chloro-7-fluoro-6-((6-(trifluoromethyl)-2,3-dihydrofuro[2,3-b]pyridin-3-yl)oxy)benzo[b]thiophen-3-yl)acetic acid;
2-(4-chloro-6-((2,3-dihydrofuro[2,3-b]pyridin-3-yl)oxy)benzo[b]thiophen-3-yl)acetic acid;
(R)-2-(4-chloro-6-((2,3-dihydrofuro[2,3-b]pyridin-3-yl)oxy)benzo[b]thiophen-3-yl)acetic acid;
(S)-2-(4-chloro-6-((2,3-dihydrofuro[2,3-b]pyridin-3-yl)oxy)benzo[b]thiophen-3-yl)acetic acid;

2-(4,7-dichloro-6-((2,3-dihydrofuro[2,3-b]pyridin-3-yl)oxy)benzo[b]thiophen-3-yl)acetic acid;
(R)-2-(4,7-dichloro-6-((2,3-dihydrofuro[2,3-b]pyridin-3-yl)oxy)benzo[b]thiophen-3-yl)acetic acid;
(S)-2-(4,7-dichloro-6-((2,3-dihydrofuro[2,3-b]pyridin-3-yl)oxy)benzo[b]thiophen-3-yl)acetic acid;
2-(4-chloro-6-((2-cyano-6,7-dihydro-5H-cyclopenta[b]pyridin-5-yl)oxy)benzo[b]thiophen-3-yl)acetic acid;
(R)-2-(4-chloro-6-((2-cyano-6,7-dihydro-5H-cyclopenta[b]pyridin-5-yl)oxy)benzo[b]thiophen-3-yl)acetic acid;
(S)-2-(4-chloro-6-((2-cyano-6,7-dihydro-5H-cyclopenta[b]pyridin-5-yl)oxy)benzo[b]thiophen-3-yl)acetic acid;
2-(6-((2-carbamoyl-6,7-dihydro-5H-cyclopenta[b]pyridin-5-yl)oxy)-4-chlorobenzo[b]thiophen-3-yl)acetic acid;
(R)-2-(6-((2-carbamoyl-6,7-dihydro-5H-cyclopenta[b]pyridin-5-yl)oxy)-4-chlorobenzo[b]thiophen-3-yl)acetic acid; or
(S)-2-(6-((2-carbamoyl-6,7-dihydro-5H-cyclopenta[b]pyridin-5-yl)oxy)-4-chlorobenzo[b]thiophen-3-yl)acetic acid;
or a pharmaceutically acceptable salt thereof.

12. The compound according to claim 1 which is:

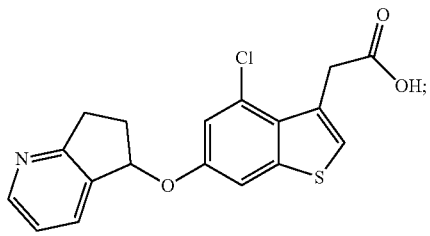

or a pharmaceutically acceptable salt thereof.

13. The compound according to claim 1 which is:

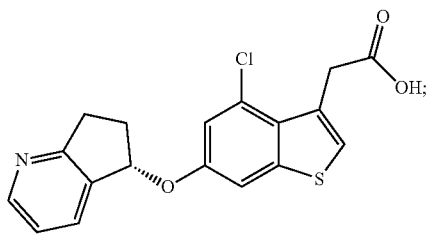 [SMILES: O=C(O)Cc1csc2cc(OC3CCc4ncccc43)cc(Cl)c12]

or a pharmaceutically acceptable salt thereof.

14. The compound according to claim 13 which is:

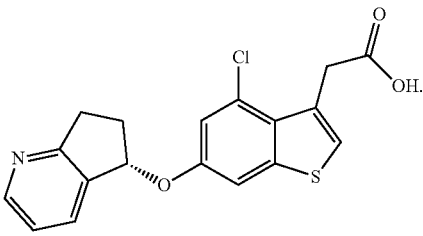

15. A combination of a compound or pharmaceutically acceptable salt thereof according claim 1 and at least one anti-adiposity agent or anti-adiposity therapy.

16. A pharmaceutical composition comprising the compound or pharmaceutically acceptable salt thereof according to claim 1 and a pharmaceutically acceptable excipient.

17. The pharmaceutical composition of claim 16, further comprising an additional pharmaceutical agent.

18. A method of treating Prader-Willi syndrome, metabolic syndrome, insulin resistance, impaired glucose tolerance, prediabetes, diabetes mellitus, type 2 diabetes mellitus, dysglycemia, hyperglycemia, obesity, increased adiposity, poor glycemic control, hyperphagia, impaired satiety, dyslipidemia, atherogenic dyslipidemia, hepatic steatosis, non-alcoholic fatty liver disease, or non-alcoholic steatohepatitis in a subject in need thereof, the method comprising administering to the subject a therapeutically effective amount of a compound of claim 1, or a pharmaceutically acceptable salt thereof.

19. A method of treating obesity in a subject in need thereof, the method comprising administering to the subject a therapeutically effective amount of a compound of claim 1, or a pharmaceutically acceptable salt thereof.

20. A method of treating Prader-Willi syndrome in a subject in need thereof, the method comprising administering to the subject a therapeutically effective amount of a compound of claim 1, or a pharmaceutically acceptable salt thereof.

* * * * *